(12) United States Patent
Lam et al.

(10) Patent No.: US 7,960,569 B2
(45) Date of Patent: Jun. 14, 2011

(54) INDOLE ANTAGONISTS OF P2Y₁ RECEPTOR USEFUL IN THE TREATMENT OF THROMBOTIC CONDITIONS

(75) Inventors: Patrick Y. S. Lam, Chadds Ford, PA (US); Charles G. Clark, Cherry Hill, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 894 days.

(21) Appl. No.: 11/872,816

(22) Filed: Oct. 16, 2007

(65) Prior Publication Data
US 2008/0221197 A1 Sep. 11, 2008

Related U.S. Application Data

(60) Provisional application No. 60/829,681, filed on Oct. 17, 2006.

(51) Int. Cl.
C07D 209/42 (2006.01)
A61K 31/403 (2006.01)
(52) U.S. Cl. .......................... 548/492; 514/419
(58) Field of Classification Search ............ 548/492; 514/419
See application file for complete search history.

(56) References Cited

U.S. PATENT DOCUMENTS

| | | | |
|---|---|---|---|
| 3,118,888 A | 1/1964 | Giraldi et al. |
| 3,162,644 A | 12/1964 | Englisch et al. |
| 4,179,563 A | 12/1979 | Butler |
| 4,186,199 A | 1/1980 | Glamkowski et al. |
| 4,435,391 A | 3/1984 | Sasahara et al. |
| 4,663,453 A | 5/1987 | Glamkowski et al. |
| 4,840,947 A | 6/1989 | Glamkowski et al. |
| 4,886,822 A | 12/1989 | Shibuya et al. |
| 5,500,424 A | 3/1996 | Nagamine et al. |
| 5,547,966 A | 8/1996 | Atwal et al. |
| 5,612,359 A | 3/1997 | Murugesan |
| 5,708,008 A | 1/1998 | Audia et al. |
| 5,886,004 A | 3/1999 | Audia et al. |
| 6,020,357 A | 2/2000 | Pinto et al. |
| 6,043,265 A | 3/2000 | Murugesan et al. |
| 6,143,764 A | 11/2000 | Kubo et al. |
| 6,180,675 B1 | 1/2001 | Widdowson et al. |
| 6,187,797 B1 | 2/2001 | Pruitt et al. |
| 6,329,395 B1 | 12/2001 | Dugar et al. |
| 6,586,453 B2 | 7/2003 | Dhanoa et al. |
| 6,596,746 B1 | 7/2003 | Das et al. |
| 6,656,933 B2 | 12/2003 | Hickey |
| 6,825,355 B2 | 11/2004 | Das et al. |
| 6,863,647 B2 | 3/2005 | Pevarello et al. |
| 2002/0077486 A1 | 6/2002 | Scarborough et al. |
| 2003/0061667 A1 | 4/2003 | Lim et al. |
| 2003/0065176 A1 | 4/2003 | Kang et al. |
| 2003/0153568 A1 | 8/2003 | Cusack et al. |
| 2003/0195232 A1 | 10/2003 | Kawasaki et al. |
| 2003/0207870 A1 | 11/2003 | Dumas et al. |
| 2003/0216396 A1 | 11/2003 | Dumas et al. |
| 2004/0023961 A1 | 2/2004 | Dumas et al. |
| 2004/0038992 A1 | 2/2004 | Bemis et al. |
| 2004/0102636 A1 | 5/2004 | Miller et al. |
| 2004/0209930 A1 | 10/2004 | Carboni et al. |
| 2004/0259875 A1 | 12/2004 | Yura et al. |
| 2005/0009815 A1 | 1/2005 | DeVita et al. |
| 2005/0012254 A1 | 1/2005 | Hsu |
| 2005/0119304 A1 | 6/2005 | Yura et al. |
| 2005/0203146 A1 | 9/2005 | Herpin et al. |
| 2005/0256161 A1 | 11/2005 | Tempest et al. |
| 2005/0261244 A1 | 11/2005 | Tuerdi et al. |
| 2005/0267119 A1 | 12/2005 | Chao et al. |
| 2006/0173002 A1 | 8/2006 | Sutton et al. |
| 2006/0293281 A1 | 12/2006 | Qiao et al. |
| 2006/0293336 A1 | 12/2006 | Sutton et al. |
| 2006/0293522 A1 | 12/2006 | Sutton |

(Continued)

FOREIGN PATENT DOCUMENTS
EP 0 028 489 5/1981

(Continued)

OTHER PUBLICATIONS

Domschke et al. (CAPLUS Abstract of: Chemische Berichte (1960), 93, 2097-2106).*
Kubinyi (3D QSAR in Drug Design: Ligand-Protein Interactions and Molecular Similarity, vol. 2-3, Springer, 1998, 800 pages) TOC and pp. 243-244 provided.*
Pfefferkorn et al. (Bioorg. Med. Chem. Lett., 18 (2008) 3338-3343).*
CAPLUS Abstract of: Vincente et al. (Organometallics (2005), 24(21), 5044-5057).*
Abbracchio, M.P. et al., "Characterization of the UDP-glucose receptor (re-named here the P2Y₁₄ receptor) adds diversity to the P2Y receptor family", Trends in Pharmacological Sciences, vol. 24, No. 2, pp. 52-55 (2003).

(Continued)

*Primary Examiner* — Robert Havlin
(74) *Attorney, Agent, or Firm* — Jing G. Sun

(57) ABSTRACT

The present invention provides indole compounds of Formula (I) or (II):

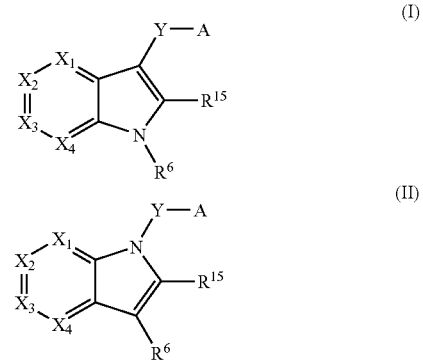

or a stereoisomer, tautomer, pharmaceutically acceptable salt or solvate form thereof, wherein the variables ring A, $X_1$, $X_2$, $X_3$, $X_4$, $R^6$, and $R^{15}$ are as defined herein. These compounds are selective inhibitors of the human P2Y₁ receptor which can be used as medicaments.

4 Claims, No Drawings

U.S. PATENT DOCUMENTS

| | | | |
|---|---|---|---|
| 2007/0004677 | A1 | 1/2007 | Chao et al. |

FOREIGN PATENT DOCUMENTS

| | | |
|---|---|---|
| EP | 0 129 692 | 1/1985 |
| EP | 0 265 734 | 5/1988 |
| EP | 0 286 979 | 10/1988 |
| EP | 0 638 557 | 2/1995 |
| EP | 1 120 409 | 8/2001 |
| EP | 1 123 918 | 8/2001 |
| EP | 1 402 888 | 3/2004 |
| EP | 1 661 879 | 5/2006 |
| EP | 1 712 242 | 10/2006 |
| FR | 1 342 550 | 12/1962 |
| JP | 56-167649 | 12/1981 |
| JP | 62-280847 | 12/1987 |
| JP | 3-39740 | 2/1991 |
| JP | 4-319958 | 11/1992 |
| JP | 7-101153 | 4/1995 |
| JP | 2001-89412 | 4/2001 |
| WO | WO 96/17825 | 6/1996 |
| WO | WO 97/29743 | 8/1997 |
| WO | WO 98/18430 | 5/1998 |
| WO | WO 98/37035 | 8/1998 |
| WO | WO 98/57951 | 12/1998 |
| WO | WO 99/31086 | 6/1999 |
| WO | WO 99/32463 | 7/1999 |
| WO | WO 00/01389 | 1/2000 |
| WO | WO 00/59506 | 10/2000 |
| WO | WO 00/76495 | 12/2000 |
| WO | WO 00/76970 | 12/2000 |
| WO | WO 01/23358 | 4/2001 |
| WO | WO 01/40231 | 6/2001 |
| WO | WO 01/47919 | 7/2001 |
| WO | WO 01/51490 | 7/2001 |
| WO | WO 01/55146 | 8/2001 |
| WO | WO 01/57008 | 8/2001 |
| WO | WO 01/72751 | 10/2001 |
| WO | WO 02/44145 | 6/2002 |
| WO | WO 02/064211 | 8/2002 |
| WO | WO 02/088090 | 11/2002 |
| WO | WO 02/090352 | 11/2002 |
| WO | WO 03/007955 | 1/2003 |
| WO | WO 03/013517 | 2/2003 |
| WO | WO 03/014064 | 2/2003 |
| WO | WO 03/026652 | 4/2003 |
| WO | WO 03/045920 | 6/2003 |
| WO | WO 03/055484 | 7/2003 |
| WO | WO 03/055848 | 7/2003 |
| WO | WO 03/080553 | 10/2003 |
| WO | WO 2004/002481 | 1/2004 |
| WO | WO 2004/012733 | 2/2004 |
| WO | WO 2004/022529 | 3/2004 |
| WO | WO 2004/046090 | 6/2004 |
| WO | WO 2004/060907 | 7/2004 |
| WO | WO 2004/085433 | 10/2004 |
| WO | WO 2004/110374 | 12/2004 |
| WO | WO 2005/037763 | 4/2005 |
| WO | WO 2005/042488 | 5/2005 |
| WO | WO 2005/063293 | 7/2005 |
| WO | WO 2005/070920 | 8/2005 |
| WO | WO2005/113537 | 12/2005 |
| WO | WO 2006/091963 | 8/2006 |

OTHER PUBLICATIONS

Abbracchio, M.P. et al., "Purinoceptors: Are There Families of P2X and P2Y Purinoceptors?", Pharmac. Ther., vol. 64, pp. 445-475 (1994).

Atwal, K.S. et al., "Cardioselective Antiischemic ATP-Sensitive Potassium Channel Openers. 4. Structure-Activity Studies on Benzopyranylcyanoguanidines: Replacement of the Benzopyran Portion", Journal of Medicinal Chemistry, vol. 39, No. 1, pp. 304-313 (1996).

Bareich, D.C. et al., "Simultaneous In Vitro Assay of the First Four Enzymes in the Fungal Aspartate Pathway Identifies a New Class of Aspartate Kinase Inhibitor", Chemistry & Biology, vol. 10, pp. 967-973 (2003).

Baurand, A. et al., "The $P2Y_1$ Receptor as a Target for New Antithrombotic Drugs: A Review of the $P2Y_1$ Antagonist MRS-2179", Cardiovascular Drug Reviews, vol. 21, No. 1, pp. 67-76 (2003).

Beaver, D.J. et al., "The Preparation and Bacteriostatic Activity of Substituted Ureas", J. Am. Chem. Soc., vol. 79, pp. 1236-1245 (1957).

Bensemann, I. et al., "Creation of hydrogen bonded 1D networks by co-crystallization of N,N'-bis(2-pyridyl)aryldiamines with dicarboxylic acids", Org. Biomol. Chem., vol. 1, pp. 1425-1434 (2003).

Boeynaems, J.-M. et al., "Overview of P2Y Receptors as Therapeutic Targets", Drug Development Research, vol. 52, pp. 187-189 (2001).

Bundgaard, H., Chapter 5: "Design and Application of Prodrugs", A Textbook of Drug Design and Development, Harwood Academic Publishers, publ., Krogsgaard-Larsen, P. et al., eds., pp. 113-191 (1991).

Bundgaard, H., "Prodrugs as a means to improve the delivery of peptide drugs", Advanced Drug Delivery Reviews, vol. 8, pp. 1-38 (1992).

Burnstock, G. et al., "P2 Purinergic Receptors: Modulation of Cell Function and Therapeutic Potential", The Journal of Pharmacology and Experimental Therapeutics, vol. 295, No. 3, pp. 862-869 (2000).

Chan, D.M.T. et al., Chapter 5: "Recent Advances in Copper-promoted C-Heteroatom Bond Cross-coupling Reactions with Boronic Acids and Derivatives", Boronic Acids: Preparation and Applications in Organic Synthesis and Medicine, Wiley-VCH Verlag GmbH & Co., publ., Hall, D.G., ed., pp. 205-240 (2005).

Chou, T.-C. et al., "Quantitative Analysis of Dose-Effect Relationships: The Combined Effects of Multiple Drugs or Enzyme Inhibitors", Adv. Enzyme Regul., vol. 22, pp. 27-55 (1984).

Cobern, D. et al., "Some New p-Chlorophenoxycarbanilides and Their Bacteriostatic Activities", J. Med. Chem., vol. 11, pp. 163-164 (1968).

Daniel, J.L. et al., "Molecular Basis for ADP-induced Platelet Activation", The Journal of Biological Chemistry, vol. 273, No. 4, pp. 2024-2029 (1998).

Duncan, Jr., R.L. et al., "Synthesis of Indolo- and Benzimidazoquinazolines and Benzodiazepines", Journal of Heterocyclic Chemistry, vol. 10, pp. 65-70 (1973).

Fabre, J.-E. et al., "Decreased platelet aggregation, increased bleeding time and resistance to thromboembolism in $P2Y_1$-deficient mice", Nature Medicine, vol. 5, No. 10, pp. 1199-1202 (1999).

Gachet, C. et al., "The platelet P2 receptors in arterial thrombosis", Blood Cells, Molecules, and Diseases, vol. 36, pp. 223-227 (2006).

Gallou, I. et al., "Practical Synthesis of Unsymmetrical Ureas from Isopropenyl Carbamates", J. Org. Chem., vol. 70, No. 17, pp. 6960-6963 (2005).

Glamkowski, E.J. et al., "Synthesis of 1,2-Dihydroindolo[1,7-ab][1,5]benzodiazepines and Related Structures (1). A New Heterocyclic Ring System", J. Heterocyclic Chem., vol. 16, pp. 865-869 (1979).

Glamkowski, E.J. et al., "Tetracyclic Benzodiazepines. 3. Synthesis of the 2,3-Dihydro-1H-quino[1,8-ab][1,5]benzodiazepine Ring System, and Derivatives of Potential Biological Interest", J. Heterocyclic Chem., vol. 24, pp. 733-737 (1987).

Gramatica, P. et al., "QSAR approach for the selection of congeneric compounds with a similar toxicological mode of action", Chemosphere, vol. 42, pp. 873-883 (2001).

Gschwend, D.A. et al., "Specificity in Structure-Based Drug Design: Identification of a Novel, Selective Inhibitor of Pneumocystis carinii Dihydrofolate Reductase", Proteins: Structure, Function and Genetics, vol. 29, pp. 59-67 (1997).

Hai, P.V. et al., "p-Cyclopentylacetophenone and Its Derivatives", J. Org. Chem., vol. 23, pp. 39-42 (1958).

Hamada, Y. et al., "The antimicrobial activity and syntheses of carbanilide derivatives," Yakugaku Zasshi, vol. 96, No. 5, pp. 663-668 (1976) (English abstract).

Hechler, B. et al., "MRS2500 [2-Iodo-$N^6$-methyl-(N)-methanocarba-2'-deoxyadenosine-3',5'-bisphosphate], a Potent, Selective, and Stable Antagonist of the Platelet $P2Y_1$ Receptor with Strong Antithrombotic Activity in Mice", The Journal of Pharmacology and Experimental Therapeutics, vol. 316, No. 2, pp. 556-563 (2006).

Hechler, B. et al., "The P2Y₁ receptor, necessary but not sufficient to support full ADP-induced platelet aggregation, is not the target of the drug clopidogrel", British Journal of Haematology, vol. 103, pp. 858-866 (1998).

Herr, R.J., "Product Class 5: Seven-Membered Hetarenes with Two or More Heteroatoms", Science of Synthesis, vol. 17, pp. 929-977 (2004).

Ito, Y. et al., "Syntheses of Nitrogen-containing Heterocyclic Compounds. XXIX. An Improved Method for the Preparation of 10H-Pyrido[3,2-b][1,4]benzoxazine (1-Azaphenoxazine)", Chem. Pharm. Bull., vol. 26, No. 5, pp. 1375-1383 (1978).

Janssens, R. et al., "Cloning and Tissue Distribution of the Human P2Y₁ Receptor", Biochemical and Biophysical Research Communications, vol. 221, No. 3, pp. 588-593 (1996).

Jin, J. et al., "Coactivation of two different G protein-coupled receptors is essential for ADP-induced platelet aggregation", Proc. Natl. Acad. Sci. USA, vol. 95, pp. 8070-8074 (1998).

Jin, J. et al., "Molecular Basis for ADP-induced Platelet Activation", The Journal of Biological Chemistry, vol. 273, No. 4, pp. 2030-2034 (1998).

Kakeya, N. et al., "Studies on Prodrugs of Cephalosporins. I. Synthesis and Biological Properties of Glycyloxybenzoyloxymethyl and Glycylaminobenzoyloxymethyl Esters of 7β[2-(2-Aminothiazol-4-yl)-(Z)-2-methoxyiminoacetamido]-3-methyl-3-cephem-4-carboxylic Acid", Chem. Pharm. Bull., vol. 32, No. 2, pp. 692-698 (1984).

Kane, Jr., J.L. et al., "Ureas of 5-Aminopyrazole and 2-Aminothiazole Inhibit Growth of Gram-Positive Bacteria", Bioorganic & Medicinal Chemistry Letters, vol. 13, pp. 4463-4466 (2003).

Lane, B.S. et al., "Direct Palladium-Catalyzed C-2 and C-3 Arylation of Indoles: A Mechanistic Rationale for Regioselectivity", J. Am. Chem. Soc., vol. 127, No. 22, pp. 8050-8057 (2005).

Lenain, N. et al., "Inhibition of localized thrombosis in P2Y₁-deficient mice and rodents treated with MRS2179, a P2Y₁ receptor antagonist", Journal of Thrombosis and Haemostasis, vol. 1, pp. 1144-1149 (2003).

Léon, C. et al., "Key Role of the P2Y₁ Receptor in Tissue Factor-Induced Thrombin-Dependent Acute Thromboembolism: Studies in P2Y₁-Knockout Mice and Mice Treated with a P2Y₁ Antagonist", Circulation, vol. 103, pp. 718-723 (2001).

Ley, S.V. et al., "Modern Synthetic Methods for Copper-Mediated C(aryl)-O, C(aryl)-N, and C(aryl)-S Bond Formation", Angewandte Chemie Int. Ed., vol. 42, pp. 5400-5449 (2003).

Marcincal-Lefebvre, A. et al., "2-[2-(Phenylthio)phenylamino]nicotinic acids and 2-[4-(phenylthio)phenylamino]nicotinic acids. Synthesis and antiinflammatory activity", Annales Pharmaceutiques Francaises, vol. 38, No. 3, pp. 243-252 (1980) (English abstract).

Matsuo, M. et al., "New 2-Aryliminoimidazolidines. I. Synthesis and Antihypertensive Properties of 2-(2-Phenoxyphenylimino)imidazolidines and Related Compounds", Chem. Pharm. Bull., vol. 33, No. 10, pp. 4409-4421 (1985).

Nielsen, N. M. et al., "Glycolamide Esters as Biolabile Prodrugs of Carboxylic Acid Agents: Synthesis, Stability, Bioconversion, and Physicochemical Properties", Journal of Pharmaceutical Sciences, vol. 77, No. 4, pp. 285-298 (1988).

Nörenberg, W. et al., "Characterization and possible function of adenosine 5'-triphosphate receptors in activated rat microglia", Br. J. Pharmacol., vol. 111, pp. 942-950 (1994).

Peng, C.-T. et al., "The Synthesis of Some 6-N-Substituted Amido Derivatives of 4,6-Diaminoquinaldine and a Study of their in vitro Antibacterial Activity", J. Am. Chem. Soc., vol. 78, pp. 3703-3708 (1956).

Phillips, G. et al., "Design, Synthesis, and Activity of 2,6-Diphenoxypyridine-Derived Factor Xa Inhibitors", J. Med. Chem., vol. 42, No. 10, pp. 1749-1756 (1999).

Rajanarendar, E. et al., "Synthesis of isoxazolylpyrazolo[3,4-d]thiazoles and isoxazolylthiazoles and their antibacterial and antifungal activity", Indian Journal of Chemistry, vol. 43B, pp. 168-173 (2004).

Roberts, M.E. et al., "On the Alkyl Derivatives of the Isomeric Ortho and Para-phenoxyphenyl Thiazolidones", The University of Kansas Science Bulletin, vol. 25, No. 11, pp. 213-227 (1938).

Rodig, O.R. et al., "Pyridine Chemistry. II. Further Studies on the Smiles Rearrangement of the 3-Amino-2,2'-dipyridyl Sulfide System. The Synthesis of Some 1,6-Diazaphenothiazines", Journal of Medicinal Chemistry, vol. 9, pp. 116-120 (1966).

Salter, M.W. et al., "ATP Causes Release of Intracellular $Ca^{2+}$ via the Phospholipase Cβ/IP₃ Pathway in Astrocytes from the Dorsal Spinal Cord", The Journal of Neuroscience, vol. 15, No. 4, pp. 2961-2971 (1995).

Savi, P. et al., "Role of P2Y1 purinoeceptor in ADP-induced platelet activation", FEBS Letters, vol. 422, pp. 291-295 (1998).

Still, W.C. et al., "Rapid Chromatographic Technique for Preparative Separations with Moderate Resolution", J. Org. Chem., vol. 43, No. 14, pp. 2923-2925 (1978).

Takeuchi, I. et al., "On the antimicrobial activity and syntheses of carbanilide and salicylanilide derivatives", Yakugaku Zasshi, vol. 102, No. 11, pp. 1023-1030 (1982) (English abstract).

Taylor, Jr., E.C. et al., "Pteridines. XIV. Further Studies on a New Approach to Pteridine Synthesis", J. Am. Chem. Soc., vol. 78, pp. 210-213 (1956).

Tomita, M. et al., "Synthesis of thiazole derivatives containing diphenyl ether nucleus", Yakugaku Zasshi, vol. 75, pp. 1077-1081 (1955) (English abstract).

Widder, K.J. et al., eds., Section III: "Prodrugs", Methods in Enzymology, vol. 112, Academic Press, Inc., publ., pp. 309-396 (1985).

Wisterowicz, K. et al., "Studies on Pyrazine Derivatives. XXVI. Synthesis and tuberculostatic activity of N-pyrazinylthioureas", Acta Polon. Pharm., vol. 46, No. 2, pp. 101-113 (1989), (English abstract only).

Wong, P.C. et al., "Nonpeptide Factor Xa Inhibitors: I. Studies with SF303 and SK549, a New Class of Potent Antithrombotics", The Journal of Pharmacology and Experimental Therapeutics, vol. 292, No. 1, pp. 351-357 (2000).

Wong, P.C. et al., "Nonpeptide Factor Xa Inhibitors II. Antithrombotic Evaluation in a Rabbit Model of Electrically Induced Carotid Artery Thrombosis", The Journal of Pharmacology and Experimental Therapeutics, vol. 295, No. 1, pp. 212-218 (2000).

Woźniak, K. et al., "Structural Similarities and Differences between N-Phenylureas and N-Phenylthioureas", J. Phys. Chem., vol. 99, No. 21, pp. 8888-8895 (1995).

Hak Sung Kim et al., "2-substitution of adenine nucleotide analogues containing a bicycle(3.1.0)hexane ring system locked in a northern conformation: Enhanced potency as P2Y1 receptor antagonists", Journal of Medicinal Chemistry, vol. 46, No. 23, pp. 4974-4986, 2003.

Wybo H. Dekker et al., "Structure-activity relationships of some antifungal indoles", Journal of Agricultural and Food Chemistry, vol. 23, No. 4, pp. 785-791, 1975.

* cited by examiner

# INDOLE ANTAGONISTS OF P2Y$_1$ RECEPTOR USEFUL IN THE TREATMENT OF THROMBOTIC CONDITIONS

CROSS REFERENCE TO OTHER APPLICATIONS

This application claims the benefit of priority from provisional U.S. Patent Application 60/829,681, filed on Oct. 17, 2006, the contents of which are herein incorporated by reference in its entirety.

FIELD OF THE INVENTION

The present invention provides novel indole compounds and analogues thereof, which are selective inhibitors of the human P2Y$_1$ receptor. The invention also provides for various pharmaceutical compositions of the same and methods for treating diseases responsive to modulation of P2Y$_1$ receptor activity.

BACKGROUND OF THE INVENTION

Purinoreceptors bind to and are activated by a variety of both ribosylated (nucleotide) and non-ribosylated (nucleoside) purines. This distinction has been used to classify these receptors into two broad groups: the P1 receptors (A1, A2a, A2b, and A3), which bind to and are activated by the nucleoside adenosine, and the P2 receptors, which comprise a second, more diverse class of receptors which are activated by a wide variety of nucleotides including ATP, ADP, UTP, and UDP. The P2 receptors can be further subdivided into two distinct types of receptors; the ionotropic P2X receptors that mediate cation flux across cellular membranes in response to ATP and the metabotropic P2Y family of receptors which are G-protein coupled receptors. In humans, the P2Y family of receptors is generally considered to consist of seven distantly related members; P2Y$_1$, P2Y$_2$, P2Y$_4$, P2Y$_6$, P2Y$_{11}$, P2Y$_{12}$, and P2Y$_{13}$ (Boeynaems, J. M. et al. *Drug Development Research* 2001, 52, 187-9). In addition, an eighth receptor, P2Y$_{14}$, has been considered by some to be a member of this class although it does not respond to ribosylated nucleotides and is activated by UDP-glucose (Abbracchio, M. P. et al. *Trends Pharmacol. Sci.* 2003, 24, 52-5).

Several studies have suggested that modulators of specific members of the P2Y family of receptors could have therapeutic potential for the treatment of a variety of disorders (for review see Burnstock, G. and Williams, M. *J. Pharm. Exp Ther.* 2000, 295, 862-9), including diabetes, cancer, cystic fibrosis, and the treatment of ischemia-reperfusion injury (Abbracchio M. P. and Burnstock G. *Pharmacol. Ther.* 1994, 64, 445-475). P2Y$_1$ receptors, almost ubiquitous among human organs (Janssens, R. et al. *Biochem. Biophys. Res. Comm.* 1996, 221, 588-593) have been identified on microglia (Norenberg, W. et al. *Br. J. Pharmacol.* 1994, 111, 942-950) and on astrocytes (Salter M. W. and Hicks J. L. *J. Neurosc.* 1995, 15, 2961-2971). Extracellular ATP activates microglial and/or astrocytes via P2Y receptors and leads directly to the release of inflammatory mediators. Microglia and astrocytes are believed to play a role in the progression of Alzheimer's disease and other CNS inflammatory disorders such as stroke and multiple sclerosis.

Two members of the P2Y family, P2Y$_1$ and P2Y$_{12}$, are of particular interest as they have now both been shown to act as important receptors for ADP in platelets (Jin, J. et al. *Proc. Natl. Acad. Sci.* 1998, 95, 8070-4). ADP is a key activator of platelets and platelet activation is known to play a pivotal role in thrombus formation under conditions of high shear stress such as those found in the arterial circulation. In addition, more recent data has suggested that platelet activation may also play a role in mediating thrombus formation under lower shear stress such as that found in the venous circulation. ADP activates platelets by simultaneously interacting with both P2Y$_1$ and P2Y$_{12}$ to produce two separate intracellular signals which synergize together to produce complete platelet activation (Jin, J. et al. *J. Biol. Chem.* 1998, 273, 2030-4). The first signal arises from ADP driven activation of the P2Y$_1$ receptor and can most easily be tracked by measuring the transitory increase in intracellular free Ca$^{+2}$. This signal appears to mediate the initial shape change reaction and to initiate the process of platelet activation. The second signal appears to be derived from ADP activation of the P2Y$_{12}$ receptor and serves to consolidate the process and produce an irreversible platelet aggregate. Using three structurally related but distinct inhibitors of P2Y$_1$ (A3P5P, A3P5PS, and A2P5P), Daniel, J. L. et al. (*J. Biol. Chem.* 1998, 273, 2024-9), Savi, P. et al. (*FEBS Letters* 1998, 422, 291-5), and Hechler, B. et al. (*Br. J. Haematol.* 1998, 103, 858-66) were the first to publish the observation that the inhibition of P2Y$_1$ activity alone could block ADP-driven aggregation independently of the P2Y$_{12}$ receptor. Although inhibition of platelet reactivity is often thought of as firm evidence of an anti-thrombotic activity, these antagonists lacked the necessary pharmacological properties for in vivo study. The first direct demonstration that inhibition of P2Y$_1$ activity could lead to an anti-thrombotic effect in vivo was reported by Leon, C. et al. *Circulation* 2001, 103, 718-23, in a model of thromboplastin induced thromboembolism using both a P2Y$_1$ knock-out mouse and the P2Y$_1$ antagonist MRS-2179 (Baurand, A. and Gachet, C. *Cardiovascular Drug Reviews* 2003, 21, 67-76). These results were subsequently extended to include the inhibition of both venous and arterial thrombosis in the rat (Lenain, N. et al. *J. Thromb. Haemost.* 2003, 1, 1144-9) and the confirmation of the phenotype of the P2Y$_1$ knock-out mouse in a second laboratory using an independently derived animal (Fabre, J-E. et al. *Nature Medicine* 1999, 5, 1199-1202). These studies highlighted the need for more potent and selective P2Y$_1$ antagonists and recently, using the P2Y$_1$ antagonist MRS-2500 (Hechler, B. et al. *J. Pharmacol Exp. Ther.* 2006, 316, 556-563) succeeded in demonstrating strong antithrombotic activity for a selective P2Y$_1$ antagonist in the mouse. Taken together, these data suggest that the discovery of novel P2Y$_1$ antagonists with improved pharmaceutical characteristics could have significant utility in the treatment of a variety of thrombotic or thromboembolic disorders (see Gachet, C. et al. *Blood Cell, Molecules and Disease* 2006, 36, 223-227 for a recent review).

SUMMARY OF THE INVENTION

Accordingly, the present invention provides novel indole compounds and analogues thereof, which are useful as selective inhibitors of the P2Y$_1$ receptor, including stereoisomers, tautomers, pharmaceutically acceptable salts, solvates and prodrugs thereof, particularly stereoisomers, tautomers and pharmaceutically acceptable salts.

The present invention also provides processes and intermediates for making the compounds of the present invention including stereoisomers, tautomers, pharmaceutically acceptable salts, solvates and prodrugs thereof, particularly stereoisomers, tautomers and pharmaceutically acceptable salts.

The present invention also provides pharmaceutical compositions comprising a pharmaceutically acceptable carrier and at least one of the compounds of the present invention or a stereoisomer, tautomer, pharmaceutically acceptable salt, solvate, or prodrug thereof, particularly a stereoisomer, tautomer or pharmaceutically acceptable salt thereof.

The present invention also provides a method for modulation of platelet reactivity comprising administering to a host in need of such treatment a therapeutically effective amount of at least one of the compounds of the present invention or a stereoisomer, tautomer, pharmaceutically acceptable salt, solvate, or prodrug thereof, particularly a stereoisomer, tautomer or pharmaceutically acceptable salt thereof.

The present invention also provides a method for treating thrombotic or thromboembolic disorders comprising administering to a host in need of such treatment a therapeutically effective amount of at least one of the compounds of the present invention or a stereoisomer, tautomer, pharmaceutically acceptable salt, solvate, or prodrug thereof, particularly a stereoisomer, tautomer or pharmaceutically acceptable salt thereof.

The present invention also provides the compounds of the present invention including stereoisomers, tautomers, pharmaceutically acceptable salts, solvates and prodrugs thereof, for use in therapy, particularly stereoisomers, tautomers and pharmaceutically acceptable salts.

The present invention also provides the use of the compounds of the present invention including stereoisomers, tautomers, pharmaceutically acceptable salts, solvates, or prodrugs thereof (particularly stereoisomers, tautomers and pharmaceutically acceptable salts thereof) for the manufacture of a medicament for the treatment of thrombotic or thromboembolic or other disorders.

These and other features of the invention will be set forth in the expanded form as the disclosure continues.

DETAILED DESCRIPTION OF THE INVENTION AND PREFERRED EMBODIMENTS

In a first aspect, the present invention provides, inter alia, a compound of Formula (I) or (II):

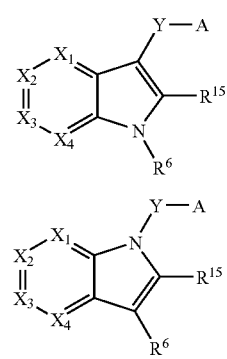

and stereoisomers, tautomers, pharmaceutically acceptable salts, solvates and prodrugs thereof (particularly stereoisomers, tautomers and pharmaceutically acceptable salts) wherein:

A (also optionally being referred to as A-1 when it is a ring) is, independently at each occurrence, selected from the group consisting of:

(a) $C_{1-8}$ alkyl substituted with 0-2 $R^1$ as $R^{1a}$ and $R^{1b}$;
(b) $C_{6-10}$ aryl substituted with 0-5 $R^1$ as $R^{1a}$, $R^{1b}$, $R^{1c}$, $R^{1d}$ and $R^{1e}$;

(c) a 5- to 10-membered heterocycle comprising: carbon atoms and 1-4 heteroatoms selected from the group consisting of N, $NR^{11}$, O and $S(O)_p$, wherein said heterocycle is substituted with 0-5 $R^1$ as $R^{1a}$, $R^{1b}$, $R^{1c}$, $R^{1d}$ and $R^{1e}$; provided that A is not a substituted or unsubstituted thiazolyl;

$X_1$, $X_2$, $X_3$ and $X_4$ are each independently selected from the group consisting of $CR^7$ and N; provided that not more than two of $X_1$, $X_2$, $X_3$ and $X_4$ are N;

Y is, independently at each occurrence, selected from the group consisting of —$(CR^{16}R^{17})_sC(O)NR^{13}(CR^{16}R^{17})_s$—, —$(CR^{16}R^{17})_sNR^{13}C(O)(CR^{16}R^{17})_s$—, —$(CR^{16}R^{17})_sSO_2NR^{10}(CR^{16}R^{17})_s$—, —$(CR^{16}R^{17})_sNR^{10}SO_2(CR^{16}R^{17})_s$—, —$C(O)(CR^{16}R^{17})_uNR^{13}$— and —$NR^{13}(CR^{16}R^{17})_uC(O)$—;

$R^1$ (as either $R^1$ or optionally referred to as $R^{1a}$, $R^{1b}$, $R^{1c}$, $R^{1d}$ and $R^{1e}$), independently at each occurrence, are each selected from the group consisting of =O, —F, —Cl, —Br, —I, —$CF_3$, —$CF_2CF_3$, —$OCF_3$, —$OCF_2CF_2H$, —$OCF_2CF_3$, —$SiMe_3$, —$(CR^fR^f)_rOR^c$, —$SR^c$, —CN, —$NO_2$, —$(CR^fR^f)_rNR^{12}R^{13}$, —$(CR^fR^f)_rC(O)R^c$, —$(CR^fR^f)_rCO_2R^c$, —$(CR^fR^f)_rC(O)NR^{12}R^{13}$, —$C(O)NR^{14}(CR^fR^f)_tNR^{12}R^{13}$, —$(CR^fR^f)_rOC(O)NR^{12}R^{13}$, —$(CR^fR^f)_rNR^{14}C(O)NR^{12}R^{13}$, —$(CR^fR^f)_rNR^{14}C(O)R^d$, —$(CR^fR^f)_rNR^{14}C(O)OR^h$, —$NR^{14}(CR^fR^f)_nC(O)R^d$, —$NR^{14}CO(CR^fR^f)_nOR^c$, —$(CH_2)_rCR^{13}$(=$NOR^c$), —$(CH_2)_r$—$C(NH_2)$(=$NOR^c$), —$S(O)_pNR^{12}R^{13}$, —$(CR^fR^f)_rNR^{14}S(O)_pNR^{12}R^{13}$, —$NR^{14}SO_2CF_3$, —$NR^{14}S(O)_pR^d$, —$S(O)_2CF_3$, —$S(O)R^d$, —$S(O)_2R^d$, —$OP(O)(OEt)_2$, —$O(CH_2)_2OP(O)(OEt)_2$, —$N(C_{1-4}$ alkyl)$_3^+Cl^-$, 4,4,5,5-tetramethyl-1,3,2-dioxaborolanyl, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —$(CR^fR^f)_r$—$C_{3-13}$ carbocycle substituted with 0-5 $R^b$, and —$(CR^fR^f)_r$-5- to 10-membered heterocycle comprising: carbon atoms and 1-4 heteroatoms selected from the group consisting of N, $NR^{11}$, O and $S(O)_p$, wherein said heterocycle is substituted with 0-5 $R^b$;

alternatively, two of $R^{1a}$, $R^{1b}$, $R^{1c}$, $R^{1d}$ and $R^{1e}$ (for example, $R^{1a}$ and $R^{1b}$; $R^{1b}$ and $R^{1c}$; $R^{1c}$ and $R^{1d}$; or $R^{1d}$ and $R^{1e}$) (which each may be the same or different) are attached to two adjacent carbon atoms and are combined with the carbon atoms to which they are attached to form a 5- to 10-membered carbocycle or heterocycle comprising: carbon atoms and either: (a) 0-3 additional heteroatoms selected from the group consisting of N, $NR^{11}$, O and $S(O)_p$ or (b) 0-2 carbonyl groups, wherein said carbocycle or heterocycle has 0-3 double bonds in the ring and is substituted with 0-5 $R^b$;

$R^6$ independently at each occurrence is selected from the group consisting of
(a) —$(CR^fR^f)_n$—$C_{3-10}$ carbocycle substituted with 0-5 $R^{6a}$; and
(b) —$(CR^fR^f)_n$-5- to 10-membered heterocycle comprising: carbon atoms and 1-4 heteroatoms selected from the group consisting of N, $NR^{11}$, O and $S(O)_p$, wherein said heterocycle is substituted with 0-5 $R^{6a}$;

$R^{6a}$ independently at each occurrence is selected from the group consisting of =O, —F, —Cl, —Br, —I, —$(CR^iR^i)_r$—$OR^c$, —$(CR^iR^i)_r$—$SR^c$, —$(CR^fR^f)_r$—CN, —$NO_2$, —$CF_3$, —$OCF_3$, —$CF_2CF_3$, —$OCF_2CF_2H$, —$OCF_2CF_3$, —$(CR^fR^f)_r$—$NR^{12}R^{13}$, —$(CR^fR^f)_r$—$C(O)R^c$, —$(CR^fR^f)_r$—$C(O)OR^c$, —$(CR^fR^f)_r$—$C(O)NR^{12}R^{13}$, —$(CR^fR^f)_r$—$NR^{14}C(O)R^d$, —$S(O)_pNR^{12}R^{13}$, —$S(O)R^d$, —$S(O)_2R^d$, —$Si(Me)_3$, —$Si(C_{1-4}$ alkyl)$_3$, $C_{1-4}$ haloalkyl, $C_{1-4}$ haloalkyloxy-, $C_{1-8}$ alkyl substituted with 0-1 $R^a$, $C_{2-8}$ alkenyl substituted with 0-1 $R^a$, $C_{2-8}$ alkynyl substituted with 0-1 $R^a$, —$(CR^fR^f)_r$—$C_{3-10}$ carbocycle substituted with 0-2 $R^e$, and —$(CR^fR^f)_r$-5- to 10-membered heterocycle comprising: carbon atoms and 1-4 heteroatoms selected from the group consisting of N, NR$^{11}$, O and S(O)$_p$, wherein said heterocycle is substituted with 0-2 R$^e$;

alternatively, when two R$^{6a}$ groups (which may be the same or different) are attached to the same carbon atom or silicon atom, together with the carbon atom or silicon atom to which they are attached, they form a 3- to 7-membered (particularly a 5- to 7-membered) carbocyclic or heterocyclic ring comprising: carbon atoms and either (a) 0-3 heteroatoms (particularly 0-2 heteroatoms) selected from the group consisting of N, NR$^{11}$, O, Si and S(O)$_p$ or (b) 0-1 carbonyl, wherein said carbocyclic or heterocyclic ring has 0-3 double bonds in the ring and is substituted with 0-4 R$^b$;

R$^7$ is, independently at each occurrence, selected from the group consisting of —H, —F, —Cl, —Br, —I, —OCF$_3$, —CF$_3$, —OR$^c$, —SR$^c$, —CN, —NO$_2$, —NR$^{12}$R$^{13}$, —C(O)R$^c$, —C(O)OR$^c$, —C(O)NR$^{12}$R$^{13}$, —NR$^{14}$C(O)R$^d$, —S(O)$_p$NR$^{12}$R$^{13}$, —S(O)R$^d$, —S(O)$_2$R$^d$, C$_{1-8}$ alkyl substituted with 0-2 R$^a$, C$_{2-8}$ alkenyl substituted with 0-2 R$^a$, C$_{2-8}$ alkynyl substituted with 0-2 R$^a$, —(CR$^f$R$^f$)$_r$—C$_{3-10}$ carbocycle substituted with 0-3 R$^b$, and —(CR$^f$R$^f$)$_r$-5- to 10-membered heterocycle comprising: carbon atoms and 1-4 heteroatoms selected from the group consisting of N, NR$^{7b}$, O and S(O)$_p$, wherein said heterocycle is substituted with 0-3 R$^b$;

alternatively, two R$^7$s on two adjacent carbon atoms, together with the carbons to which they are attached, form a 5- to 7-membered carbocyclic or heterocyclic ring comprising: carbon atoms and 0-3 ring heteroatoms selected from the group consisting of O, N, NR$^{7b}$ and S(O)$_p$, wherein said carbocyclic or heterocyclic ring is substituted with 0-2 R$^{7c}$;

R$^{7b}$ is selected from the group consisting of H, C$_{1-4}$ alkyl, —C(O)(C$_{1-4}$ alkyl), —C(O)phenyl, —C(O)benzyl and benzyl;

R$^{7c}$ is, independently at each occurrence, selected from the group consisting of —H, —F, —Cl, —Br, —I, —OCF$_3$, —CF$_3$, —OR$^c$, —SR$^c$, —CN, —NO$_2$, —NR$^{12}$R$^{13}$, —C(O)R$^c$, —C(O)OR$^c$, —C(O)NR$^{12}$R$^{13}$, —NR$^{14}$C(O)R$^d$, —S(O)$_p$NR$^{12}$R$^{13}$, —S(O)R$^d$, —S(O)$_2$R$^d$, C$_{1-4}$ alkyl, phenyl substituted with 0-3 R$^b$ and benzyl substituted with 0-3 R$^b$;

R$^{11}$ is, independently at each occurrence, selected from the group consisting of H, C$_{1-4}$ alkoxy, C$_{1-6}$ alkyl substituted with 1-5 fluorine, —(CR$^f$R$^f$)$_r$C(O)NR$^{12}$R$^{13}$, C$_{1-8}$ alkyl substituted with 0-2 R$^a$, C$_{2-4}$ alkenyl substituted with 0-1 R$^a$, C$_{2-4}$ alkynyl substituted with 0-1 R$^a$, —C(O)(C$_{1-6}$ alkyl), —C(O)(CH$_2$)$_n$(C$_{3-6}$ cycloalkyl), —C(O)(CH$_2$)$_n$(C$_{6-10}$ aryl), —C(O)(CH$_2$)$_n$(5- to 10-membered heteroaryl), —C(O)O(C$_{1-8}$ alkyl), —C(O)O(CH$_2$)$_n$(C$_{3-6}$ cycloalkyl), —C(O)O(CH$_2$)$_n$(C$_{6-10}$ aryl), —C(O)O(CH$_2$)$_n$(5- to 10-membered heteroaryl), —C(O)O(CH$_2$)$_{2-4}$(C$_{1-4}$ alkyl), —C(O)NH(C$_{1-8}$ alkyl), —C(O)NH(CH$_2$)$_n$(C$_{3-6}$ cycloalkyl), —C(O)NH(CH$_2$)$_n$(C$_{6-10}$ aryl), —C(O)NH(CH$_2$)$_n$(5- to 10-membered heteroaryl), —S(O)$_2$(C$_{1-8}$ alkyl), —S(O)$_2$(CH$_2$)$_n$(C$_{3-6}$ cycloalkyl), —S(O)$_2$(CH$_2$)$_n$(C$_{6-10}$ aryl), —S(O)$_2$(CH$_2$)$_n$(5- to 10-membered heteroaryl), —(CR$^f$R$^f$)$_r$—C$_{3-10}$ carbocycle, and —(CR$^f$R$^f$)$_r$-5- to 10-membered heterocycle; wherein (a) each of said alkyls, cycloalkyls, aryls, and carbocycles are each substituted with 0-2 R$^b$ and (b) each of said heteroaryls and heterocycles comprise: carbon atoms and 1-4 heteroatoms selected from the group consisting of N, NR$^f$, O and S(O)$_p$ and are also substituted with 0-2 R$^b$;

R$^{12}$ is independently at each occurrence selected from the group consisting of H, C$_{1-6}$ alkyl substituted with 1-5 fluorine, —(CR$^f$R$^f$)$_r$C(O)NR$^f$R$^f$, C$_{1-6}$ alkyl, —C(O)(C$_{1-6}$ alkyl), —C(O)(CH$_2$)$_n$(C$_{6-10}$ aryl), —C(O)(CH$_2$)$_n$(5- to 10-membered heteroaryl), —C(O)O(C$_{1-4}$ alkyl), —C(O)OCH$_2$(C$_{6-10}$ aryl), —(CH$_2$)$_n$C(O)OCH$_2$(5- to 10-membered heteroaryl), —(CH$_2$)$_n$OC(O)(C$_{1-4}$ alkyl), —(CH$_2$)$_n$OC(O)(C$_{6-10}$ aryl), —(CH$_2$)$_n$OC(O)(5- to 10-membered heteroaryl), —(CH$_2$)$_n$C(O)O(C$_{1-4}$ alkyl), —(CH$_2$)$_n$C(O)O(C$_{6-10}$ aryl), —(CH$_2$)$_n$C(O)O(5- to 10-membered heteroaryl), —(CH$_2$)$_n$C(O)NH(C$_{1-6}$ alkyl), —(CH$_2$)$_n$C(O)NH(C$_{6-10}$ aryl), —(CH$_2$)$_n$C(O)NH(5- to 10-membered heteroaryl), —(CH$_2$)$_r$OC(O)NH(C$_{1-6}$ alkyl), —(CH$_2$)$_r$OC(O)NH(C$_{6-10}$ aryl), —(CH$_2$)$_r$OC(O)NH(5- to 10-membered heteroaryl), —S(O)$_2$(C$_{1-6}$ alkyl), —S(O)$_2$(CH$_2$)$_n$(C$_{6-10}$ aryl), —S(O)$_2$(CH$_2$)$_n$(5- to 10-membered heteroaryl), —(CR$^f$R$^f$)$_n$—(C$_{6-10}$ aryl), and —(CR$^f$R$^f$)$_n$-5- to 10-membered heteroaryl; wherein (a) each of said alkyls and aryls are each substituted with 0-2 R$^g$ and (b) said heteroaryls comprise: carbon atoms and 1-4 heteroatoms selected from the group consisting of N, NR$^f$, O and S(O)$_p$;

R$^{13}$ is independently at each occurrence selected from the group consisting of H, C$_{1-6}$ alkyl and —(CH$_2$)$_n$-phenyl;

alternatively, R$^{12}$ and R$^{13}$, when attached to the same nitrogen, combine with the nitrogen to form a 5- to 10-membered heterocyclic ring comprising: carbon atoms and 1-2 additional heteroatoms selected from the group consisting of N, NR$^f$, O and S(O)$_p$;

R$^{14}$ is independently at each occurrence selected from the group consisting of H, C$_{1-6}$ alkyl substituted with 0-2 R$^{14a}$, C$_{2-6}$ alkenyl substituted with 0-2 R$^{14a}$, C$_{2-6}$ alkynyl substituted with 0-2 R$^{14a}$, —(CH$_2$)$_r$—C$_{3-10}$ carbocycle substituted with 0-3 R$^g$, and —(CH$_2$)$_r$-5- to 10-membered heterocycle comprising: carbon atoms and 1-4 heteroatoms selected from the group consisting of N, NR$^{11}$, O and S(O)$_p$, wherein said heterocycle is substituted with 0-3 R$^g$;

R$^{14a}$ is independently at each occurrence selected from the group consisting of —H, C$_{1-4}$ alkyl, —OR$^f$, —Cl, —F, —Br, —I, =O, —CF$_3$, —CN, —NO$_2$, —NR$^{12}$R$^{13}$, —C(O)R$^f$, —C(O)OR$^f$, —C(O)NR$^{12}$R$^{13}$ and —S(O)$_p$R$^f$;

R$^{15}$ is independently at each occurrence selected from the group consisting of —H, —OR$^f$, —SR$^f$, —F, —Cl, —Br, —I, —CN, —NO$_2$, —NR$^f$R$^f$, —C(O)R$^f$, —C(O)OR$^f$, —NR$^f$C(O)R$^f$, —C(O)NR$^f$R$^f$, —SO$_2$NR$^f$R$^f$, —NR$^f$SO$_2$CF$_3$, —S(O)$_2$CF$_3$, —S(O)$_p$—C$_{1-4}$ alkyl, —(CF$_2$)$_r$CF$_3$, C$_{1-4}$ alkyl, C$_{2-4}$ alkenyl and C$_{2-4}$ alkynyl;

R$^{16}$ and R$^{17}$ are independently at each occurrence each selected from the group consisting of —H, —F, —Cl, —OH and C$_{1-4}$ alkyl;

R$^a$ is independently at each occurrence selected from the group consisting of —H, =O, —F, —OCF$_3$, —CF$_3$, —(CR$^f$R$^f$)$_r$OR$^c$, —(CR$^f$R$^f$)$_r$SR$^c$, CN, —(CR$^f$R$^f$)$_r$NR$^{12}$R$^{13}$, —(CR$^f$R$^f$)$_r$C(O)R$^c$, —(CR$^f$R$^f$)$_r$C(O)OR$^c$, —(CR$^f$R$^f$)$_r$C(O)NR$^{12}$R$^{13}$, —(CR$^f$R$^f$)$_r$NR$^{14}$C(O)R$^d$, —(CR$^f$R$^f$)$_r$S(O)$_p$NR$^{12}$R$^{13}$, —(CR$^f$R$^f$)$_r$S(O)R$^d$, —(CR$^f$R$^f$)$_r$S(O)$_2$R$^d$, C$_{1-4}$ alkyl substituted with 1-5 fluorine, —(CH$_2$)$_r$—C$_{3-10}$ carbocycle substituted with 0-3 R$^e$ and —(CH$_2$)$_r$-5- to 10-membered heterocycle comprising: carbon atoms and 1-4 heteroatoms selected from the group consisting of N, NR$^f$, O and S(O)$_p$, wherein said heterocycle is substituted with 0-3 R$^e$;

R$^b$ is independently at each occurrence selected from the group consisting of —H, =O, —F, —Cl, —Br, —I, —(CH$_2$)$_r$—OR$^c$, —SR$^c$, —CN, —NO$_2$, —CF$_3$, —OCF$_3$, —(CR$^f$R$^f$)$_r$NR$^{12}$R$^{13}$, —C(O)R$^c$, —(CH$_2$)$_r$—C(O)OR$^c$, —(CH$_2$)$_r$—C(O)NR$^{12}$R$^{13}$, —NR$^{14}$C(O)R$^d$, —S(O)$_p$NR$^{12}$R$^{13}$, —S(O)R$^d$, —S(O)$_2$R$^d$, C$_{1-4}$ haloalkyl, C$_{1-4}$ haloalkyloxy-, C$_{1-4}$ alkyloxy-, C$_{1-4}$ alkylthio-, C$_{1-4}$ alkyl-C(O)—, C$_{1-4}$ alkyl-O—C(O)—, C$_{1-4}$ alkyl-C(O)NH—, C$_{1-8}$ alkyl substituted with 0-2 R$^a$, C$_{2-8}$ alkenyl substituted with 0-2 R$^a$, C$_{2-8}$ alkynyl substituted with 0-2 R$^a$, —(CH$_2$)$_r$—C$_{3-10}$ carbocycle substituted with 0-3 R$^e$ and —(CH$_2$)$_r$-5- to 10-membered heterocycle comprising: carbon atoms and 1-4 heteroatoms selected from the group consisting of N, NR$^f$, O and S(O)$_p$, wherein said heterocycle is substituted with 0-3 R$^e$;

$R^c$ is independently at each occurrence selected from the group consisting of H, —OP(O)(OEt)$_2$, $C_{1-8}$ alkyl substituted with 0-3 $R^e$, $C_{2-8}$ alkenyl substituted with 0-3 $R^e$, $C_{2-8}$ alkynyl substituted with 0-3 $R^e$, —(CR$^f$R$^f$)$_r$—C$_{3-8}$ cycloalkyl substituted with 0-3 $R^e$, —(CR$^f$R$^f$)$_r$—C$_{6-10}$ aryl substituted with 0-3 $R^e$ and —(CR$^f$R$^f$)$_r$-5- to 10-membered heterocycle comprising: carbon atoms and 1-4 heteroatoms selected from the group consisting of N, NR$^f$, O and S(O)$_p$, wherein said heterocycle is substituted with 0-3 $R^e$;

$R^d$ is independently at each occurrence selected from the group consisting of CF$_3$, OH, $C_{1-4}$ alkoxy, $C_{1-6}$ alkyl, —(CH$_2$)$_r$—C$_{3-10}$ carbocycle substituted with 0-3 $R^e$ and —(CH$_2$)$_r$-5- to 10-membered heterocycle comprising: carbon atoms and 1-4 heteroatoms selected from the group consisting of N, NR$^f$, O and S(O)$_p$, wherein said heterocycle is substituted with 0-3 $R^e$;

$R^e$ is independently at each occurrence selected from the group consisting of —H, =O, —(CH$_2$)$_r$—OR$^f$, —(CH$_2$)$_r$—SR$^f$, —F, —Cl, —Br, —I, —CN, —NO$_2$, —(CH$_2$)$_r$—NR$^{12}$R$^{13}$, —C(O)R$^f$, —(CH$_2$)$_r$—C(O)OR$^f$, —NR$^{14}$C(O)R$^f$, —(CH$_2$)$_r$—C(O)NR$^{12}$R$^{13}$, —SO$_2$NR$^{12}$R$^{13}$, —NR$^{14}$SO$_2$NR$^{12}$R$^{13}$, —NR$^{14}$SO$_2$—C$_{1-4}$ alkyl, —NR$^{14}$SO$_2$CF$_3$, —NR$^{14}$SO$_2$-phenyl, —S(O)$_2$CF$_3$, —S(O)$_p$—OR$^h$, —(CF$_2$)$_r$CF$_3$, Si(Me)$_3$, —Si(Me)$_2$(t-Bu), —Si(C$_{1-4}$ alkyl)$_3$, C$_{1-8}$ alkyl substituted with 0-2 R$^g$, C$_{2-8}$ alkenyl substituted with 0-2 R$^g$, C$_{2-8}$ alkynyl substituted with 0-2 R$^g$, —(CH$_2$)$_r$—C$_{3-8}$ cycloalkyl substituted with 0-2 R$^g$, —(CH$_2$)$_r$—C$_{6-10}$ aryl substituted with 0-2 R$^g$, and —(CH$_2$)$_r$-5- to 10-membered heterocycle comprising: carbon atoms and 1-4 heteroatoms selected from the group consisting of N, NR$^f$, O and S(O)$_p$, wherein said heterocycle is substituted with 0-2 R$^g$;

alternatively, two $R^e$ groups on adjacent atoms, together with the atoms to which they are attached, form a 5- to 7-membered carbocyclic or heterocyclic ring comprising: carbon atoms and either (a) 0-2 heteroatoms selected from the group consisting of N, NR$^{11}$, O and S(O)$_p$ or (b) 0-1 carbonyl, wherein said carbocyclic or heterocyclic ring has 0-3 double bonds in the ring and is substituted with 0-3 R$^g$;

$R^f$ is independently at each occurrence selected from the group consisting of H, F, C$_{1-6}$ alkyl and —(CH$_2$)$_n$-phenyl;

$R^g$ is independently at each occurrence selected from the group consisting of —H, =O, —OR$^f$, —SR$^f$, —F, —Cl, —Br, —I, —CN, —NO$_2$, —NR$^f$R$^f$, —C(O)R$^f$, —C(O)OR$^f$, —NR$^f$C(O)R$^f$, —C(O)NR$^f$R$^f$, —SO$_2$NR$^f$R$^f$, —NR$^f$SO$_2$NR$^f$R$^f$, —NR$^f$SO$_2$—C$_{1-4}$ alkyl, —NR$^f$SO$_2$CF$_3$, —NR$^f$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl and C$_{2-6}$ alkynyl;

$R^h$ is independently at each occurrence selected from the group consisting of C$_{1-6}$ alkyl substituted with 0-2 R$^g$, —(CH$_2$)$_n$-phenyl substituted with 0-2 R$^g$, and —(CH$_2$)$_n$-5- to 10-membered heterocycle comprising: carbon atoms and 1-4 heteroatoms selected from the group consisting of N, NR$^f$, O and S(O)$_p$, wherein said heterocycle is substituted with 0-2 R$^g$;

$R^i$ is independently at each occurrence selected from the group consisting of H, C$_{1-6}$ alkyl substituted with 0-2 R$^g$, —(CH$_2$)$_n$-phenyl substituted with 0-2 R$^g$, and —(CH$_2$)$_n$-5- to 10-membered heterocycle comprising: carbon atoms and 1-4 heteroatoms selected from the group consisting of N, NR$^f$, O and S(O)$_p$, wherein said heterocycle is substituted with 0-2 R$^g$;

n, at each occurrence, is selected from the group consisting of 0, 1, 2, 3 and 4;

p, at each occurrence, is selected from the group consisting of 0, 1 and 2;

r, at each occurrence, is selected from the group consisting of 0, 1, 2, 3 and 4;

s, at each occurrence, is selected from the group consisting of 0, 1, 2 and 3;

t, at each occurrence, is selected from the group consisting of 1, 2, 3 and 4; and u, at each occurrence, is selected from the group consisting of 1 and 2;

provided that:

(1) when any of $X_1$, $X_2$, $X_3$ and $X_4$ are CR$^7$, Y is —CONH—, (2) when R$^6$ is a substituted or unsubstituted benzyl, then A is other than substituted or unsubstituted pyridyl or substituted or unsubstituted pyrimidinyl;

(3) in Formula (I), $X_1$ is other than C—CH$_2$-piperidyl;

(4) in Formula (I), when Y is —CH$_2$CONH—, then R$^6$ is other than 3-Cl-5-CF$_3$-pyrid-2-yl;

(5) in Formula (I), when Y is —CH$_2$CONH—, R$^6$ is fluorine substituted phenyl, and A is other than unsubstituted pyridyl;

(6) in Formula (I), when Y is —CONH—, (a) each of $X_1$, $X_2$, $X_3$ and $X_4$ is CH or one of $X_1$, $X_2$, $X_3$ and $X_4$ is C-halo, C—OH or C-alkanoyl, (b) A or A-1 is phenyl substituted with CO$_2$H or CO$_2$alkyl and (c) R$^6$ is other than substituted or unsubstituted phenyl;

(7) in Formula (I), when each of $X_1$, $X_2$, $X_3$ and $X_4$ is CH, Y is —CONH—, R$^{15}$ is H, R$^6$ is an unsubstituted phenyl and A or A-1 is other than 1-phenylpropyl;

(8) in Formula (I), when each of $X_1$, $X_2$, $X_3$ and $X_4$ is CH, Y is —C(O)NR$^{13}$— or —C(O)NR$^{13}$CH$_2$—, R$^6$ is —(CH$_2$)$_n$—C$_{3-6}$ cycloalkyl or —(CH$_2$)$_n$-phenyl, and A or A-1 is other than substituted biphenyl;

(9) in Formula (I), when each of $X_1$, $X_2$ and $X_4$ is CH, $X_3$ is C—OMe, Y is —CONH—, R$^{15}$ is methyl, R$^6$ is ethoxy substituted phenyl, and A or A-1 is other than methyl substituted phenyl;

(10) in Formula (II), when each of $X_1$, $X_2$, $X_3$ and $X_4$ is CH, Y is —CONH—, R$^{15}$ is unsubstituted phenyl, A or A-1 is other than methyl substituted phenyl; and

(11) in Formula (II), when each of $X_1$, $X_2$, $X_3$ and $X_4$ is CH, Y is —CONH—, R$^{15}$ is H, A or A-1 is an unsubstituted phenyl or unsubstituted pyridyl, R$^6$ is other than an unsubstituted phenyl, unsubstituted pyridyl, unsubstituted tetrahydropyridinyl, or methyl substituted tetrahydropyridinyl.

In a second aspect of the invention described above is provided a particular embodiment which is a compound of Formula (I) or (II) wherein:

A (also referred to as A-1) has a more particular value (independently at each occurrence) selected from the group consisting of C$_{6-10}$ aryl substituted with 0-5 R$^1$, and a 5- to 10-membered heteroaryl comprising: carbon atoms and 1-4 heteroatoms selected from the group consisting of N, NR$^{11}$, O and S(O)$_p$, wherein said heteroaryl is substituted with 0-5 R$^1$; provided that A is not a substituted or unsubstituted thiazolyl;

$X_1$, $X_2$, $X_3$ and $X_4$ are as defined above, except that not more that one of $X_1$, $X_2$, $X_3$ and $X_4$ is N;

Y has a more particular value (independently at each occurrence) selected from the group consisting of —C(O)NR$^{13}$—, —NR$^{13}$C(O)—, —SO$_2$NR$^{10}$— and —NR$^{10}$SO$_2$—;

R$^6$ has a more particular value (independently at each occurrence) selected from the group consisting of:

(a) a more particular group for R$^6$ for Formula (I) is selected from the group consisting of:

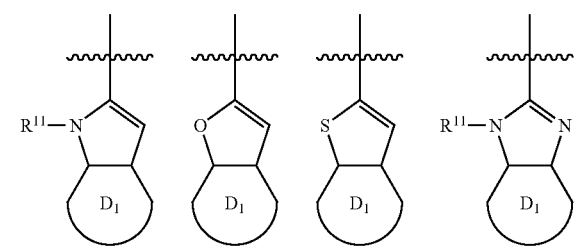

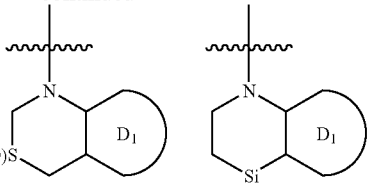

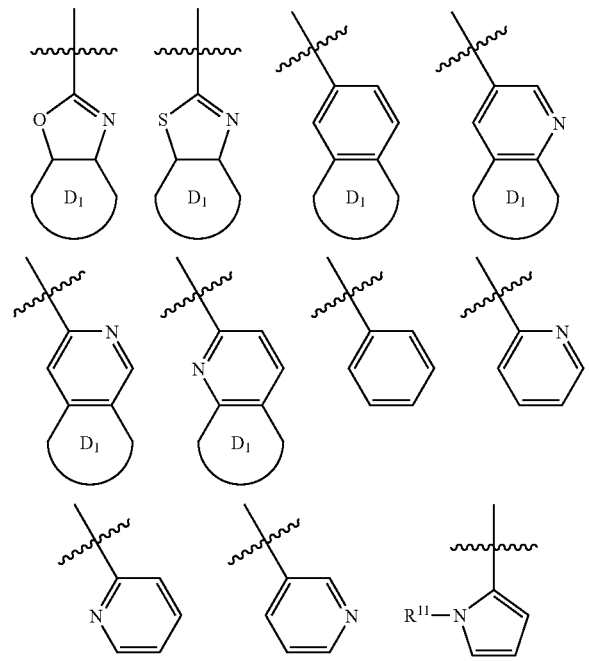

(b) a more particular group for $R^6$ for Formula (II) is selected from the group consisting of:

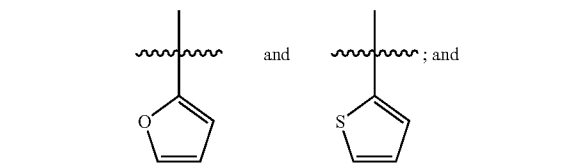

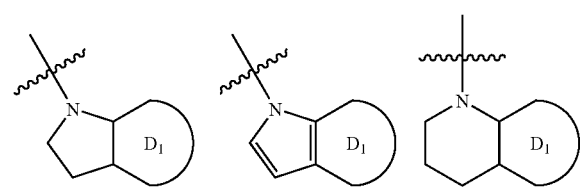

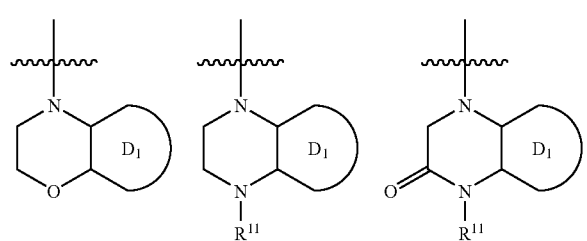

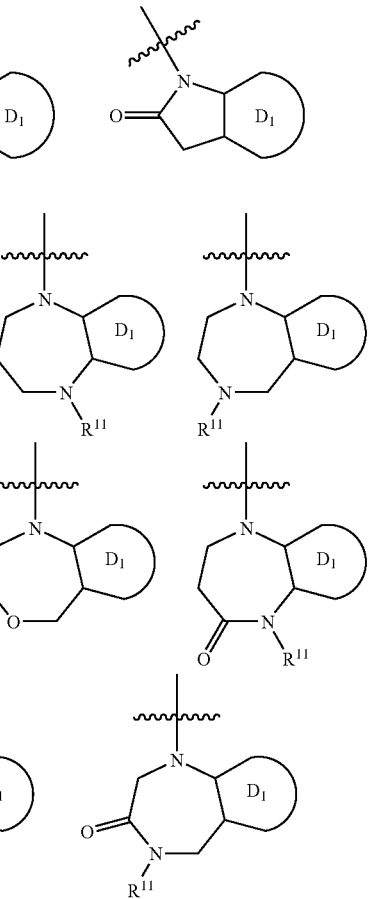

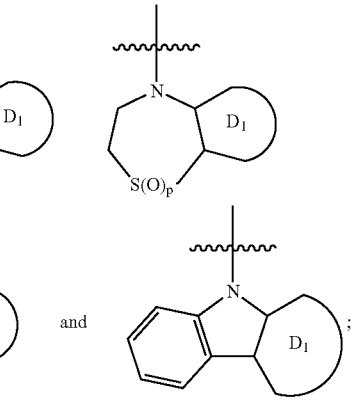

wherein for each of groups (a) and (b):

(i) $D_1$ is a 5- to 7-membered carbocycle or a 5-6-membered heterocycle comprising: carbon atoms and (a) 0-3 ring heteroatoms selected from the group consisting of (a) N, $NR^{11}$, O and $S(O)_p$ or (b) 0-2 carbonyl groups and wherein said carbocyclic or heterocyclic ring has 0-3 double bonds in the ring; and (ii) each of the rings may be substituted with 0-4 $R^{6a}$.

In a third aspect of the invention described above is provided a particular embodiment which is a compound of Formula (Ia) or (IIa),

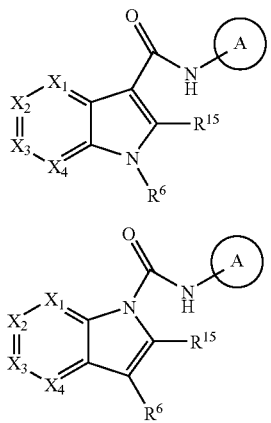

or a stereoisomer, tautomer, pharmaceutically acceptable salt, solvate, or prodrug thereof (particularly a stereoisomer, tautomer or pharmaceutically acceptable salt thereof), wherein:

ring A-1 (wherein "A-1" is optionally used throughout the application as a term to refer to "A" when A is a ring) is a particular value of A and is independently at each occurrence selected from the group consisting of $C_{6-10}$ aryl substituted with 0-5 $R^1$, or a 5- to 10-membered heteroaryl comprising: carbon atoms and 1-4 heteroatoms selected from N, $NR^{11}$, O and $S(O)_p$, wherein said heteroaryl is substituted with 0-5 $R^1$; provided that ring A is not a substituted or unsubstituted thiazolyl;

$X_1$, $X_2$, $X_3$ and $X_4$ have the values defined above under the first aspect of the invention;

$R^1$ have the values defined above under the first aspect of the invention except that for the two $R^1$s on two adjacent carbon atoms that form the carbocycle or heterocycle, the carbocycle or heterocycle is substituted with 0-4 $R^b$;

$R^6$ has the same meaning as described above under the first aspect of the invention;

alternatively, when two $R^{6a}$ groups (which may be the same or different) are attached to the same carbon atom or silicon atom, together with the carbon or silicon atom to which they are attached, they form a 3- to 7-membered (particularly a 5- to 7-membered) carbocyclic or heterocyclic ring comprising: carbon atoms and either (a) 0-3 heteroatoms (particularly 0-2 heteroatoms) selected from N, $NR^{11}$, O, Si and $S(O)_p$ or (b) 0-1 carbonyl, wherein said carbocyclic or heterocyclic ring has 0-3 double bonds in the ring and is substituted with 0-3 $R^b$;

$R^7$ has the same meaning described above for the first aspect of the invention;

$R^{7b}$ has the same meaning described above for the first aspect of the invention;

$R^{7c}$ has the same meaning described above for the first aspect of the invention;

$R^{11}$ has the same meaning described above for the first aspect of the invention;

$R^{12}$ has the same meaning described above for the first aspect of the invention;

$R^{13}$ has the same meaning described above for the first aspect of the invention;

alternatively, $R^{12}$ and $R^{13}$, when attached to the same nitrogen, combine to form a 5- to 10-membered heterocyclic ring comprising: carbon atoms and 1-2 additional heteroatoms selected from N, $NR^{11}$, O and $S(O)_p$ as defined above under the first aspect of the invention;

$R^{14}$ has the same meaning described above for the first aspect of the invention;

$R^{14a}$ has the same meaning described above for the first aspect of the invention;

$R^{15}$ has the same meaning described above for the first aspect of the invention;

$R^{16}$ has the same meaning described above for the first aspect of the invention;

$R^{17}$ has the same meaning described above for the first aspect of the invention;

$R^a$ has the same meaning described above for the first aspect of the invention;

$R^b$ has the same meaning described above for the first aspect of the invention;

$R^c$ has the same meaning described above for the first aspect of the invention;

$R^d$ has the same meaning described above for the first aspect of the invention;

$R^e$ has the same meaning described above for the first aspect of the invention;

alternatively, two $R^e$ groups, (which may be the same or different) together with the same atoms to which they are attached, form a 5- to 7-membered carbocyclic or heterocyclic ring comprising: carbon atoms and either (a) 0-2 heteroatoms selected from the group consisting of N, $NR^{11}$, O, Si and $S(O)_p$ or (b) 0-1 carbonyl, wherein said carbocyclic or heterocyclic ring has 0-3 double bonds in the ring and is substituted with 0-3 $R^g$ wherein $R^g$ has the same definition as described in the first embodiment;

$R^f$ has the same meaning described above for the first aspect of the invention;

$R^g$ has the same meaning described above for the first aspect of the invention;

$R^h$ has the same meaning described above for the first aspect of the invention;

$R^i$ has the same meaning described above for the first aspect of the invention;

n, at each occurrence has the same meaning described above for the first aspect of the invention;

p, at each occurrence has the same meaning described above for the first aspect of the invention;

r, at each occurrence has the same meaning described above for the first aspect of the invention;

s, at each occurrence has the same meaning described above for the first aspect of the invention; and t, at each occurrence has the same meaning described above for the first aspect of the invention;

provided that:

(1) when any of $X_1$, $X_2$, $X_3$ and $X_4$ is $CR^7$, and $R^6$ is a substituted or unsubstituted benzyl, then A is other than substituted or unsubstituted pyridyl or substituted or unsubstituted pyrimidinyl;

(2) in Formula (Ia), $X_1$ is other than C—CH$_2$-piperidyl;

(3) in Formula (Ia), when each of $X_1$, $X_2$, $X_3$ and $X_4$ is selected to be CH or one of $X_1$, $X_2$, $X_3$ and $X_4$ is C-halo, C—OH or C-alkanoyl, A is phenyl substituted with CO$_2$H or CO$_2$alkyl and $R^6$ is other than substituted or unsubstituted phenyl;

(4) in Formula (Ia), when each of $X_1$, $X_2$, $X_3$ and $X_4$ is selected to be CH, $R^{15}$ is H, $R^6$ is unsubstituted phenyl and A is other than 1-phenylpropyl;

(5) in Formula (Ia), when each of $X_1$, $X_2$, $X_3$ and $X_4$ is selected to be CH, $R^6$ is —$(CH_2)_n$—$C_{3-6}$ cycloalkyl or —$(CH_2)_n$-phenyl, and A is other than substituted biphenyl;

(6) in Formula (Ia), when each of $X_1$, $X_2$, and $X_4$ is selected to be CH, $X_3$ is C—OMe, $R^{15}$ is methyl, $R^6$ is ethoxy substituted phenyl, and A is other than methyl substituted phenyl;

(7) in Formula (IIa), when each of $X_1$, $X_2$, $X_3$ and $X_4$ is selected to be CH, $R^{15}$ is unsubstituted phenyl, and A is other than methyl substituted phenyl; and (8) in Formula (IIa), when each of $X_1$, $X_2$, $X_3$ and $X_4$ is selected to be CH, $R^{15}$ is H, A is an unsubstituted phenyl or unsubstituted pyridyl, and $R^6$ is other than an unsubstituted phenyl, an unsubstituted pyridyl, an unsubstituted tetrahydropyridinyl, or a methyl substituted tetrahydropyridinyl.

In a fourth aspect of the present invention is provided a compound of Formula (Ia) or (IIa), within the scope of the third aspect wherein:

$X_1$, $X_2$, $X_3$ and $X_4$ are each independently selected from the group consisting of $CR^7$ and N; provided that not more that one of $X_1$, $X_2$, $X_3$ and $X_4$ is N;

$R^6$ has more particular values selected from the group consisting of:

(a) a more particular group for $R^6$ for Formula (Ia) is selected from the group consisting of:

(b) a more particular group for $R^6$ for Formula (IIa) is selected from the group consisting of:

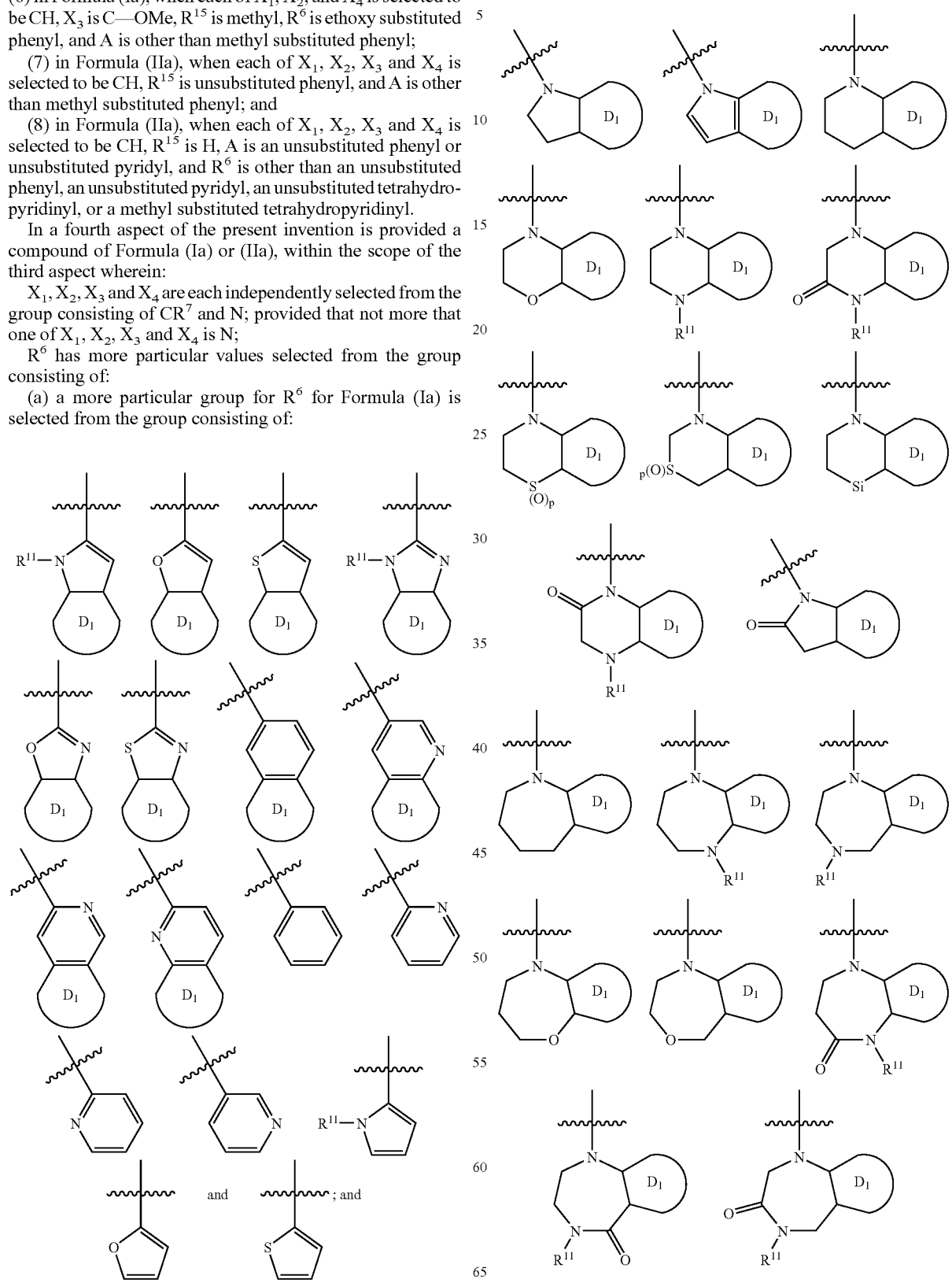

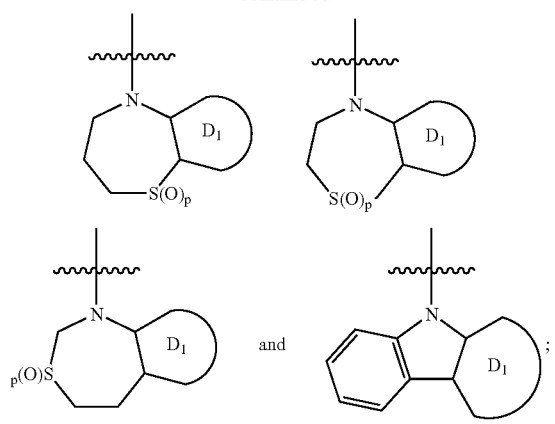

wherein for each of (a) and (b):

(i) $D_1$ is a 5- to 7-membered carbocycle or a 5-6-membered heterocycle comprising: carbon atoms and (a) 0-3 ring heteroatoms selected from the group consisting of (a) N, $NR^{11}$, O and $S(O)_p$ or (b) 0-2 carbonyl groups and wherein said carbocyclic or heterocyclic ring has 0-3 double bonds in the ring; and (ii) each of the rings may be substituted with 0-4 $R^{6a}$.

In a fifth aspect, the present invention provides a compound of Formula (Ia) or (IIa), within the scope of the third aspect wherein:

ring A (also called A-1) is, independently at each occurrence, selected from the group consisting of:

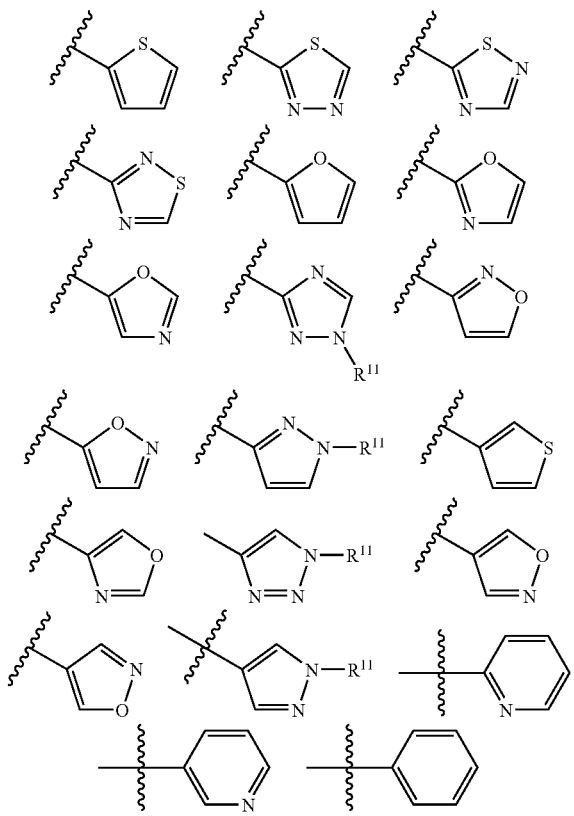

and substituted with 0-4 $R^1$;

$X_1, X_2, X_3$ and $X_4$ are each independently selected from the group consisting of $CR^7$ and N, provided that not more one of $X_1, X_2, X_3$ and $X_4$ is N;

$R^6$, independently at each occurrence, has a more particular value and is selected from the group consisting of:

(a) a more particular group for $R^6$ for Formula (Ia) is selected from the group consisting of:

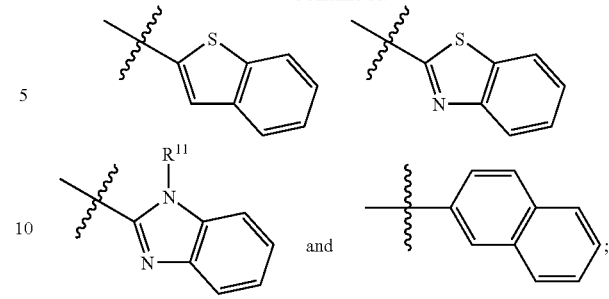

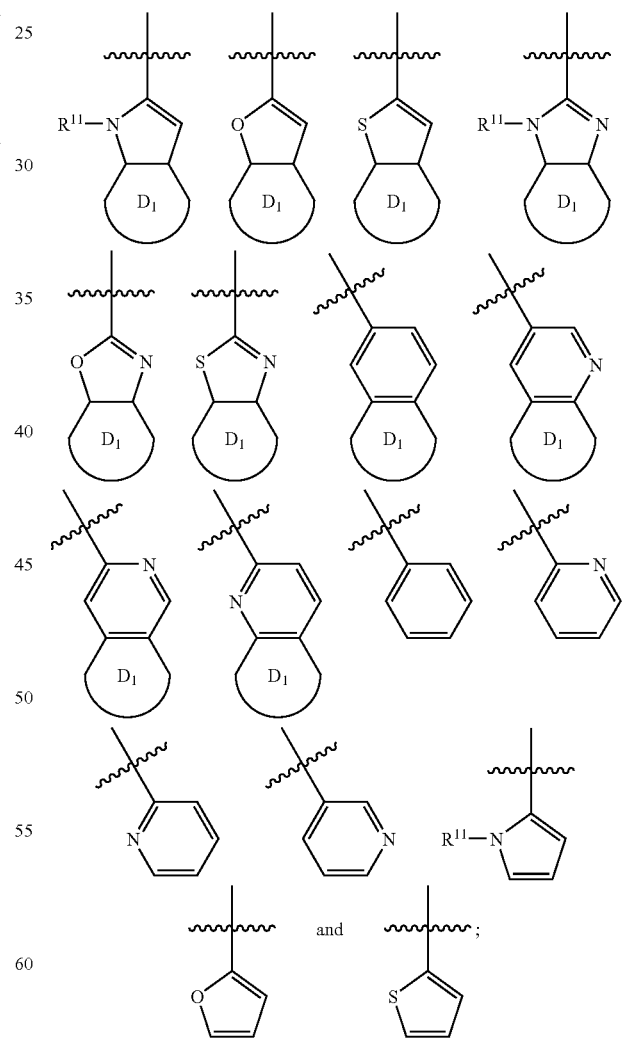

and substituted with 0-4 $R^{6a}$ and wherein $D_1$ has a more particular value and is selected from the group consisting of cyclopentyl, cyclohexyl, piperidinyl, tetrahydropyranyl, phenyl, pyridinyl, pyrimidinyl, thiophenyl, pyrrolyl, furanyl, thiazolyl, imidazolyl and oxazolyl; and (b) a more particular group for $R^6$ for Formula (IIa) is selected from the group consisting of:

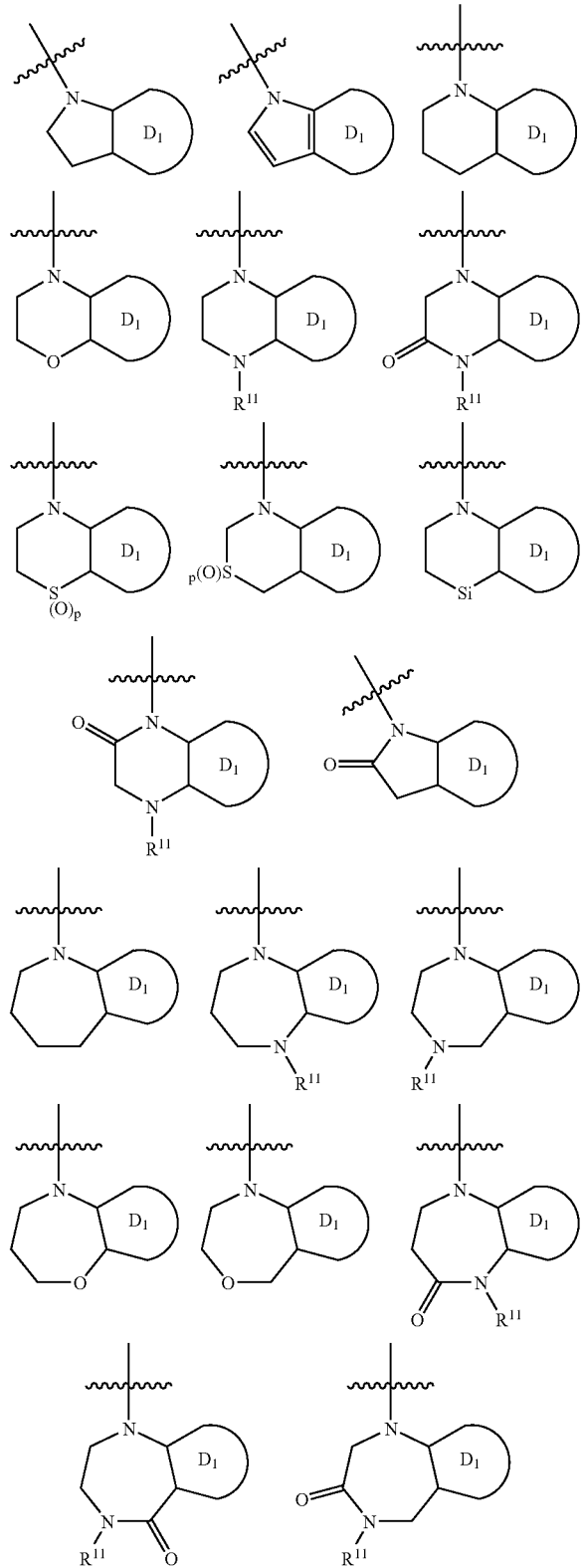

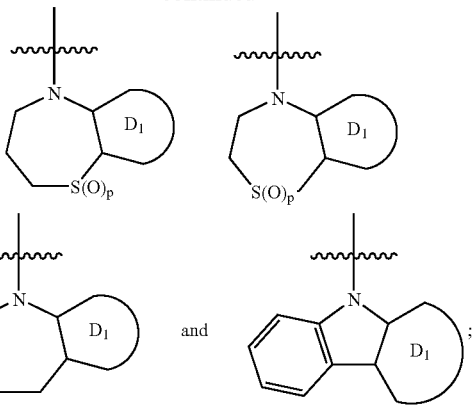

-continued wherein:

(i) for each of groups (a) and (b) $D_1$ has a more particular value and is selected from the group consisting of cyclopentyl, cyclohexyl, piperidinyl, tetrahydropyranyl, phenyl, pyridinyl, pyrimidinyl, thiophenyl, pyrrolyl, furanyl, thiazolyl, imidazolyl and oxazolyl; and (ii) the $R^6$ group in Formula (IIa) is substituted with 0-4 $R^{6a}$;

$R^1$ has a more particular value and is (independently at each occurrence) selected from the group consisting of —F, —Cl, —Br, —I, —$CF_3$, —$CF_2CF_3$, —$OCF_3$, —$OCF_2CF_2H$, —$OCF_2CF_3$, $SiMe_3$, —$(CR^fR^f)_r$—$OR^c$, —$SR^c$, —CN, —$NO_2$, —$(CR^fR^f)_r$—$NR^{12}R^{13}$, —$(CR^fR^f)_r$—$C(O)R^c$, —$(CR^fR^f)_r$—$CO_2R^c$, —$(CR^fR^f)_r$—$C(O)NR^{12}R^{13}$, —$OP(O)(OEt)_2$, 4,4,5,5-tetramethyl-1,3,2-dioxaborolanyl, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —$(CR^fR^f)_r$—$C_{3-13}$ carbocycle substituted with 0-5 $R^b$, and —$(CR^fR^f)_r$-5- to 10-membered heterocycle comprising: carbon atoms and 1-4 heteroatoms selected from the group consisting of N, $NR^{11}$, O and $S(O)_p$, wherein said heterocycle is substituted with 0-5 $R^b$;

alternatively, two of $R^{1a}$, $R^{1b}$, $R^{1c}$, $R^{1d}$ and $R^{1e}$ (for example, $R^{1a}$ and $R^{1b}$; $R^{1b}$ and $R^{1c}$; $R^{1c}$ and $R^{1d}$; or $R^{1d}$ and $R^{1e}$) (which may be the same or different) on two adjacent carbon atoms are combined with the carbon atoms to which they are attached to form a 5- to 7-membered carbocycle or heterocycle comprising: carbon atoms and either: (a) 0-3 additional heteroatoms selected from the group consisting of N, $NR^{11}$, O and $S(O)_p$ or (b) 0-2 carbonyl groups, wherein said carbocycle or heterocycle is substituted with 0-5 $R^b$;

$R^{6a}$ has a more particular value and is (independently at each occurrence) selected from the group consisting of —F, —Cl, —Br, —I, —$(CR^iR^i)_r$$OR^c$, —$SR^c$, —CN, —$CF_3$, —$OCF_3$, —$CF_2CF_3$, —$OCF_2CF_2H$, —$OCF_2CF_3$, —$(CR^fR^f)_r$ $NR^{12}R^{13}$, —$C(O)R^c$, —$(CR^fR^f)_rC(O)OR^c$, —$Si(Me)_3$, $C_{1-4}$ haloalkyl, $C_{1-4}$ haloalkyloxy-, $C_{1-4}$ alkyl-$C(O)NH$—, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —$(CR^fR^f)_r$—$C_{3-10}$ carbocycle substituted with 0-2 $R^e$, or —$(CR^fR^f)_r$-5- to 10-membered heterocycle comprising: carbon atoms and 1-4 heteroatoms selected from the group consisting of N, $NR^{11}$, O and $S(O)_p$, wherein said heterocycle is substituted with 0-2 $R^e$;

alternatively, when two $R^{6a}$ groups (which may be the same or different) are attached to the same carbon atom or silicon atom, together with the carbon atom or silicon atom to which they are attached, they form a 3- to 7-membered (particularly a 5- to 7-membered) carbocyclic or heterocyclic ring comprising: carbon atoms and either (a) 0-3 heteroatoms (particularly 0-2 heteroatoms) selected from the group consisting of N, NR$^{11}$, O, Si and S(O)$_p$ or (b) 0-1 carbonyl, wherein said carbocyclic or heterocyclic ring has 0-3 double bonds in the ring and is substituted with 0-4 R$^b$;

R$^{11}$ has a more particular value and is (independently at each occurrence) selected from the group consisting of H, C$_{1-8}$ alkyl substituted with 0-2 R$^a$, —C(O)(CH$_2$)$_n$(C$_{3-6}$ cycloalkyl), —C(O)(CH$_2$)$_n$phenyl, —C(O)O(C$_{1-8}$ alkyl), —C(O)O(CH$_2$)$_n$(C$_{3-6}$ cycloalkyl), —C(O)O(CH$_2$)$_n$phenyl, —C(O)O(CH$_2$)$_{2-4}$(C$_{1-4}$ alkyl), —C(O)NH(C$_{1-6}$ alkyl), —S(O)$_2$(C$_{1-6}$ alkyl), —S(O)$_2$(CH$_2$)$_n$phenyl, —(CR$^f$R$^f$)$_r$—C$_{3-7}$ cycloalkyl, —(CR$^f$R$^f$)$_r$-phenyl, and —(CR$^f$R$^f$)$_r$-5- to 6-membered heterocycle; wherein said alkyl, cycloalkyl, phenyl, and aryl are substituted with 0-2 R$^b$, and said heteroaryl and heterocycle are substituted with 0-2 R$^b$ and comprise: carbon atoms and 1-4 heteroatoms selected from the group consisting of N, NR$^f$, O and S(O)$_p$.

In a sixth aspect of the present is provided a more particular embodiment which is a compound of Formula (Ib) or (IIb):

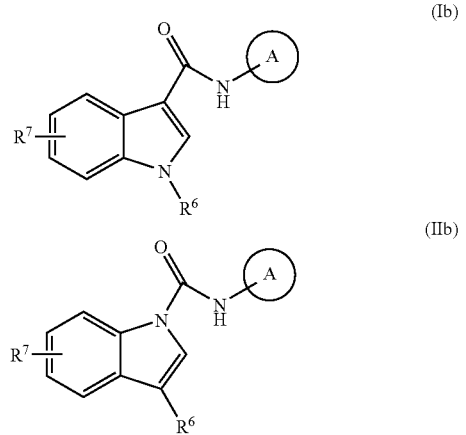

or a stereoisomer, tautomer, pharmaceutically acceptable salt, solvate, or prodrug thereof (particularly stereoisomers, tautomers and pharmaceutically acceptable salts) wherein:

ring A-1 (also called A), independently at each occurrence, has a more particular value and is selected from the group consisting of C$_{6-10}$ aryl substituted with 0-3 R$^1$, and a 5- to 10-membered heteroaryl comprising: carbon atoms and 1-4 heteroatoms selected from the group consisting of N, NR$^{11}$, O, and S(O)$_p$, wherein said heteroaryl is substituted with 0-3 R$^1$; provided that ring A-1 is not a substituted or unsubstituted thiazolyl;

R$^1$ has a more particular value and is (independently at each occurrence) selected from the group consisting of —F, —Cl, —Br, —I, —CF$_3$, —CF$_2$CF$_3$, —OCF$_3$, —OCF$_2$CF$_2$H, —OCF$_2$CF$_3$, —SiMe$_3$, —(CR$^f$R$^f$)$_r$OR$^c$, —SR$^c$, —CN, —NO$_2$, —(CR$^f$R$^f$)$_r$NR$^{12}$R$^{13}$, —(CR$^f$R$^f$)$_u$C(O)R$^c$, —(CR$^f$R$^f$)$_r$CO$_2$R$^c$, —(CR$^f$R$^f$)$_u$C(O)NR$^{12}$R$^{13}$, —OP(O)(OEt)$_2$, 4,4,5,5-tetramethyl-1,3,2-dioxaborolanyl, C$_{1-8}$ alkyl substituted with 0-2 R$^a$, —(CR$^f$R$^f$)$_u$—C$_{3-6}$ carbocycle substituted with 0-2 R$^b$, and —(CR$^f$R$^f$)$_u$-5- to 6-membered heterocycle comprising: carbon atoms and 1-4 heteroatoms selected from the group consisting of N, NR$^{11}$, O and S(O)$_p$, wherein said heterocycle is substituted with 0-2 R$^b$;

alternatively, two R$^1$s on two adjacent carbon atoms are combined with the carbon atoms to which they attached, form a 5- to 7-membered carbocycle or heterocycle comprising: carbon atoms and 0-3 additional heteroatoms selected from N, NR$^{11}$, O, and S(O)$_p$, and 0-1 carbonyl groups, wherein said carbocycle or heterocycle is substituted with 0-4 R$^b$;

R$^6$ has a more particular value and is (independently at each occurrence) is and selected from the group consisting of (a) a more particular group for R$^6$ for Formula (Ib) is selected from the group consisting of:

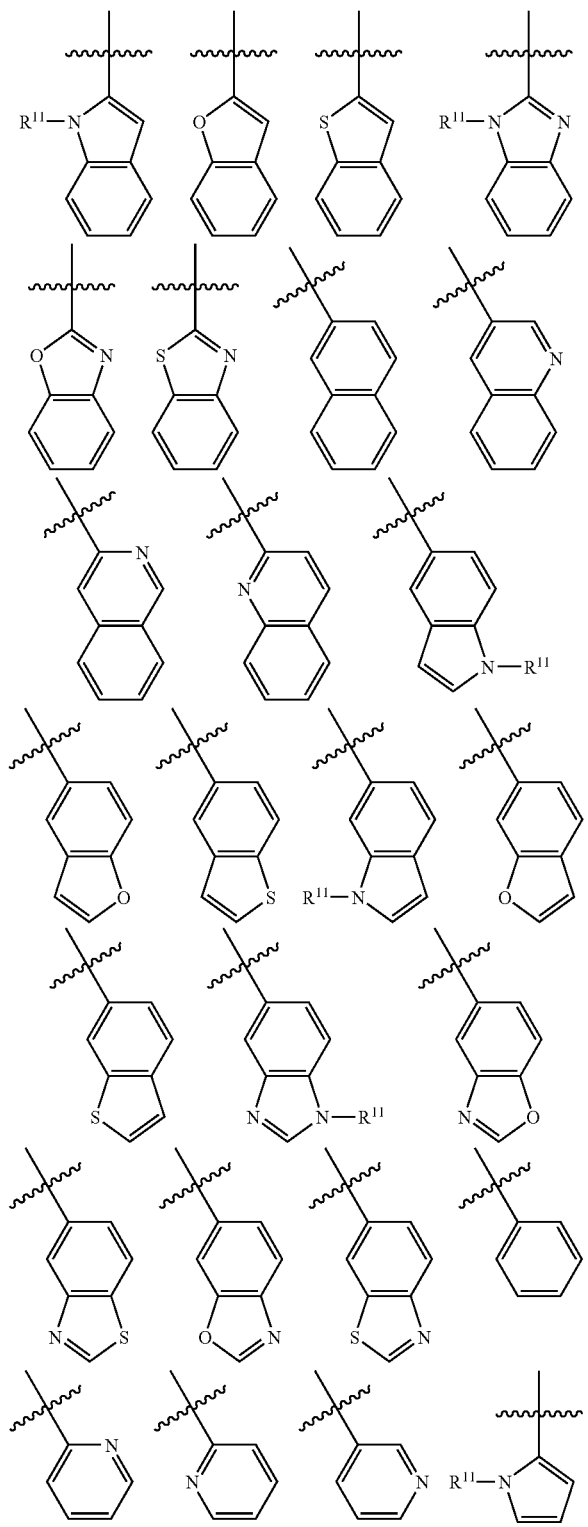

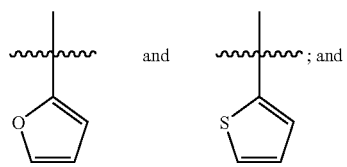
(b) a more particular group for $R^6$ for Formula (IIb) is selected from the group consisting of:
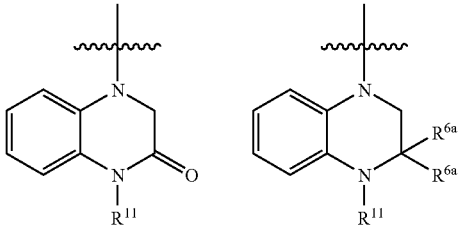
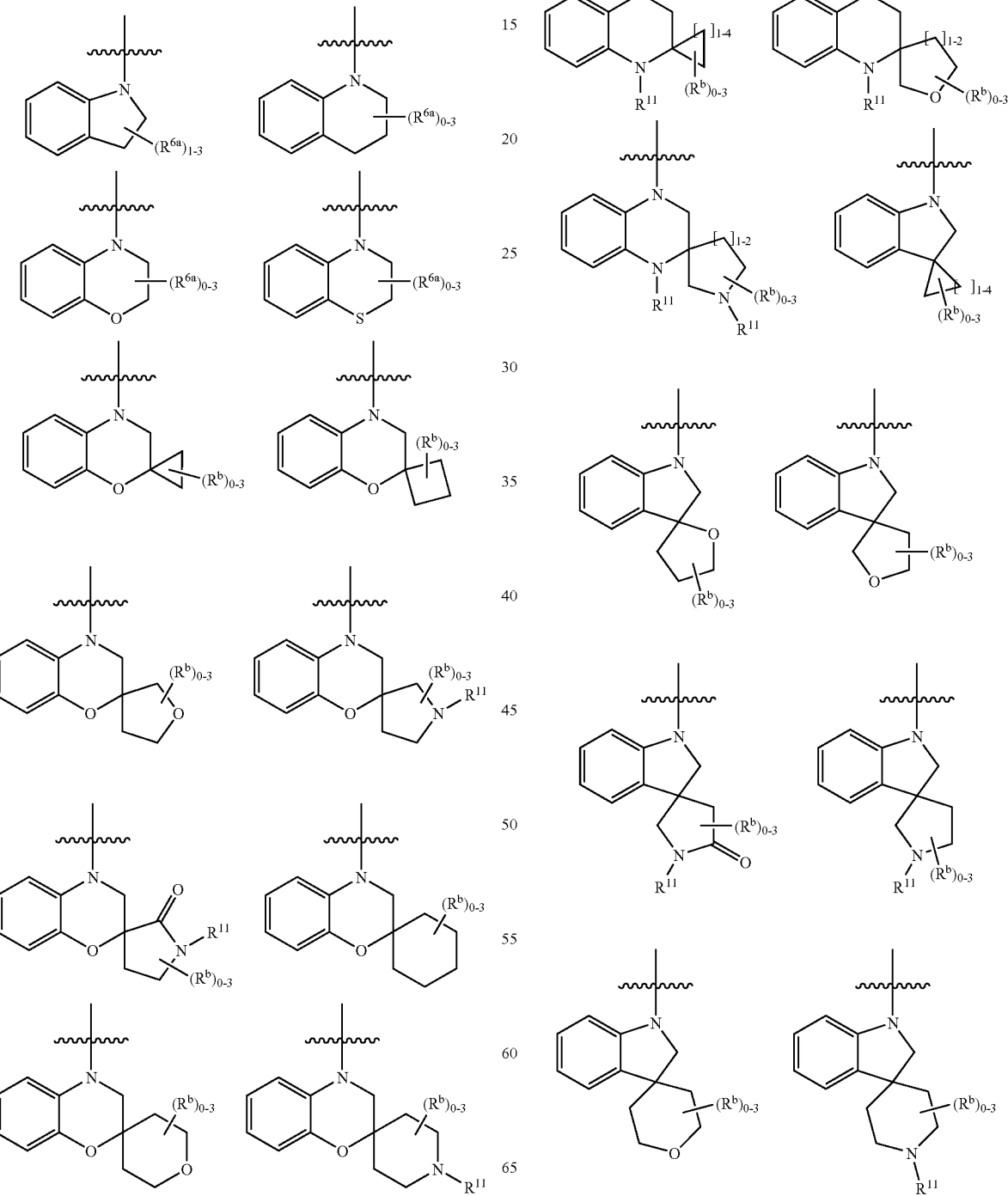

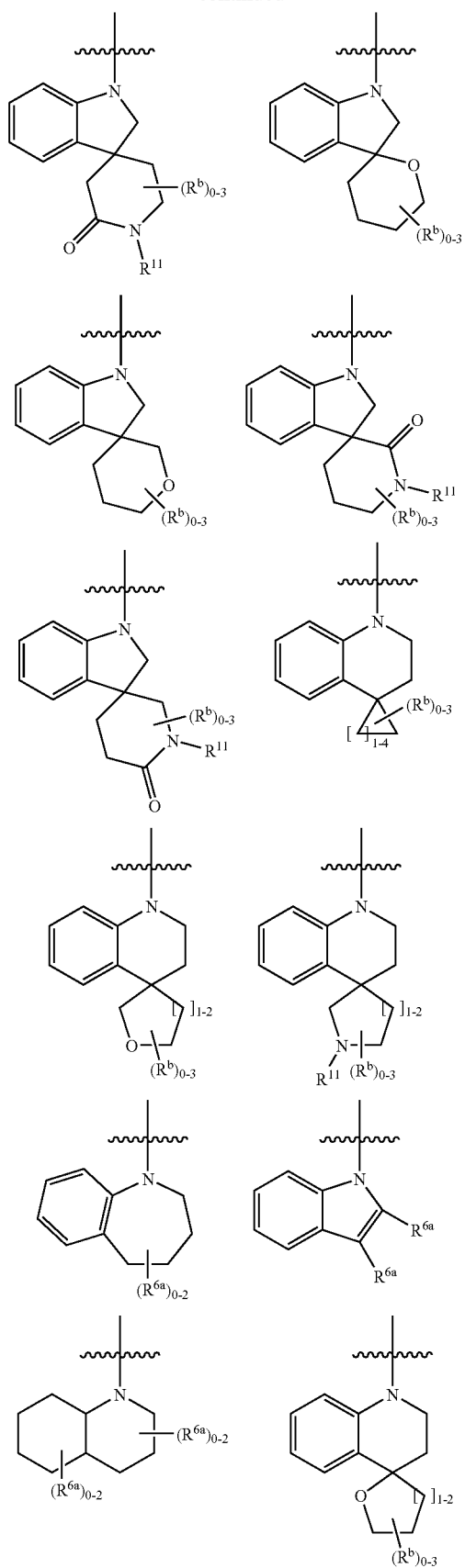
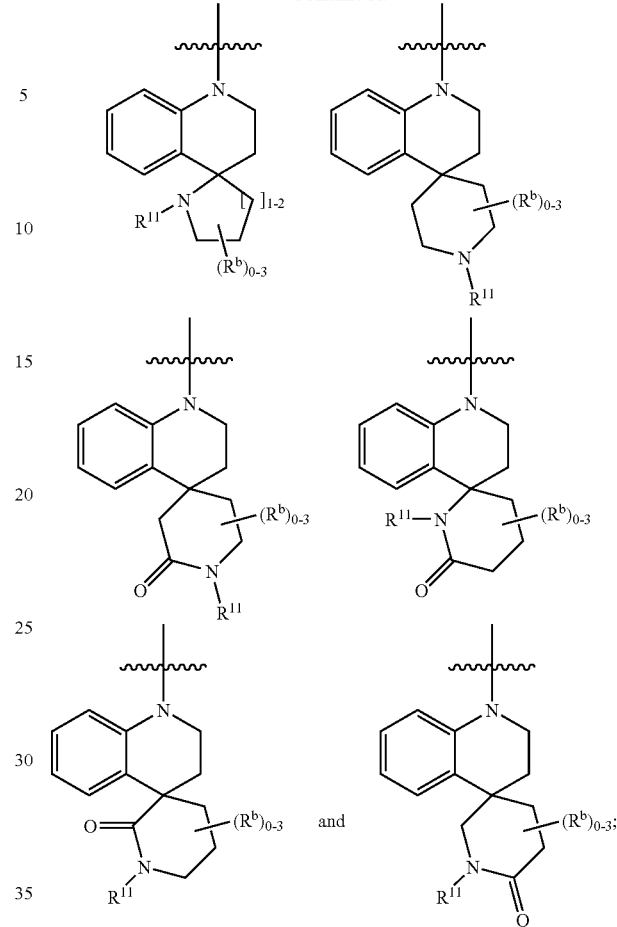

wherein for each of groups (a) and (b):
(i) $R^6$ is substituted with 0-3 $R^{6a}$; and
(ii) the phenyl ring in each of the structures is substituted with 0-2 $R^{6a}$;

$R^{6a}$ has a more particular value and is (independently at each occurrence) selected from the group consisting of —F, —Cl, —Br, —I, —$(CH_2)_r$—$OR^c$, —$(CH_2)_r$—$SR^c$, —$C(Me)_2$ OMe, —$C(Me)_2$OEt, —$C(Me)_2$OPr, —CHMeO $(CH_2)_2$OMe, —$C(Me)_2$O$(CH_2)_2$OMe, —$C(Et)_2$OMe, —$C(Et)_2$OEt, —CH=CHCO$_2$(t-Bu), —CN, —$C(Me)_2$CN, —CF$_3$, —OCF$_3$, —CF$_2$CF$_3$, —OCF$_2$CF$_2$H, —OCF$_2$CF$_3$, —$(CH_2)_r$—NR$^{12}$R$^{13}$, —C(O)R$^c$, —(CR$^f$R$^f$)$_r$—C(O)OR$^c$, —Si(Me)$_3$, C$_{1-4}$ haloalkyl, C$_{1-4}$ haloalkyloxy-, C$_{1-4}$ alkyl-C(O)NH—, C$_{1-8}$ alkyl substituted with 0-2 R$^a$, C$_{2-8}$ alkenyl substituted with 0-2 R$^a$, C$_{2-8}$ alkynyl substituted with 0-2 R$^a$, —$(CH_2)_r$—C$_{3-7}$ cycloalkyl substituted with 0-2 R$^e$, —$(CH_2)_r$-phenyl substituted with 0-2 R$^e$, and —$(CH_2)_r$-5- to 10-membered heterocycle comprising: carbon atoms and 1-4 heteroatoms selected from the group consisting of N, NR$^{11}$, O and S(O)$_p$, wherein said heterocycle is substituted with 0-2 R$^e$;

alternatively, when two R$^{6a}$ groups (which may be the same or different) are attached to the same carbon atom or silicon atom, together with the carbon atom or silicon atom to which they are attached, they form a 3- to 7-membered (particularly a 5- to 7-membered) carbocyclic or heterocyclic ring comprising: carbon atoms and either (a) 0-3 heteroatoms (particularly 0-2 heteroatoms) selected from the group consisting of N, NR$^{11}$, O, Si and S(O)$_p$ or (b) 0-1 carbonyl, wherein said carbocyclic or heterocyclic ring has 0-3 double bonds in the ring and is substituted with 0-4 R$^b$;

R⁷ has a more particular value and is (independently at each occurrence) selected from the group consisting of —H, —CH₃, —Cl, —Br, —CN, —OCH₃, —SCH₃ and NHCH₃;

R¹¹ has a more particular value and is (independently at each occurrence) selected from the group consisting of $C_{1-6}$ alkyl, —CH₂CH₂OH, —CH₂CH₂OCH₃, —C(O)($C_{1-6}$ alkyl), —C(O)phenyl, —C(O)benzyl, —C(O)O($C_{1-6}$ alkyl), —C(O)Obenzyl, —CH₂CO₂H, —CH₂CO₂($C_{1-6}$ alkyl), —C(O)NH($C_{1-6}$ alkyl), —C(O)NHbenzyl, —S(O)₂($C_{1-6}$ alkyl), —S(O)₂phenyl, —S(O)₂benzyl, phenyl and benzyl;

R¹² has a more particular value and is (independently at each occurrence) selected from the group consisting of H, $C_{1-6}$ alkyl, —C(O)($C_{1-6}$ alkyl), —C(O)(CH₂)$_n$phenyl, —C(O)(CH₂)$_n$(5- to 6-membered heteroaryl), —(CH₂)$_n$C(O)NH($C_{1-6}$ alkyl), —(CH₂)$_n$C(O)NHphenyl, —(CH₂)$_n$C(O)NH(5- to 6-membered heteroaryl), —(CH₂)$_t$OC(O)NH($C_{1-6}$ alkyl), —S(O)₂($C_{1-6}$ alkyl), —S(O)₂(CH₂)$_n$phenyl, —S(O)₂(CH₂)$_n$(5- to 6-membered heteroaryl), —(CH₂)$_n$-phenyl and —(CH₂)$_n$-5- to 6-membered heteroaryl; wherein said heteroaryl comprises: carbon atoms and 1-4 heteroatoms selected from the group consisting of N, $NR^f$, O and $S(O)_p$;

R¹³ has a more particular value and is (independently at each occurrence) selected from the group consisting of H, $C_{1-6}$ alkyl, or —(CH₂)$_n$-phenyl;

alternatively, R¹² and R¹³, when attached to the same nitrogen, combine to form a 5- to 10-membered heterocyclic ring comprising: carbon atoms and 1-2 additional heteroatoms selected from the group consisting of N, $NR^f$, O and $S(O)_p$;

$R^a$ has a more particular value and is (independently at each occurrence) selected from the group consisting of —H, =O, —F, —OCF₃, —CF₃, —$OR^c$, —$SR^c$, —CN, —NR¹²R¹³, —C(O)$R^c$, —C(O)O$R^c$, —C(O)NR¹²R¹³, —NR¹⁴C(O)$R^d$, —S(O)$_p$NR¹²R¹³, —S(O)$R^d$, —S(O)₂$R^d$, —(CH₂)$_u$—$C_{3-6}$ cycloalkyl substituted with 0-2 $R^e$, —(CH₂)$_u$-phenyl substituted with 0-2 $R^e$, and —(CH₂)$_u$-5- to 6-membered heterocycle comprising: carbon atoms and 1-4 heteroatoms selected from the group consisting of N, $NR^f$, O and $S(O)_p$, wherein said heterocycle is substituted with 0-2 $R^e$;

$R^b$ has a more particular value and is (independently at each occurrence) selected from the group consisting of —H, —F, —Cl, —Br, $C_{1-4}$ alkyl, —OH, —CO₂H, —NH₂, —CF₃, —OCF₃, $C_{1-4}$ alkyloxy, $C_{3-7}$ cycloalkyl, phenyl and benzyl;

$R^c$ has a more particular value and is (independently at each occurrence) selected from the group consisting of H, —OP(O)(OEt)₂, $C_{1-8}$ alkyl substituted with 0-3 $R^e$, $C_{2-4}$ alkenyl substituted with 0-3 $R^e$, $C_{2-4}$ alkynyl substituted with 0-3 $R^e$, —(CH₂)$_u$—$C_{3-6}$ cycloalkyl substituted with 0-3 $R^e$, —(CH₂)$_u$-phenyl substituted with 0-3 $R^e$, and —(CH₂)$_u$-5- to 6-membered heterocycle comprising: carbon atoms and 1-4 heteroatoms selected from the group consisting of N, $NR^f$, O and $S(O)_p$, wherein said heterocycle is substituted with 0-3 $R^e$;

$R^d$ has a more particular value and is (independently at each occurrence) selected from the group consisting of —CF₃, —OH, $C_{1-4}$ alkoxy, $C_{1-6}$ alkyl, —(CH₂)$_u$—$C_{3-6}$ cycloalkyl substituted with 0-3 $R^e$, —(CH₂)$_u$-phenyl substituted with 0-3 $R^e$, and —(CH₂)$_u$-5- to 6-membered heterocycle comprising: carbon atoms and 1-4 heteroatoms selected from the group consisting of N, $NH^f$, O and $S(O)_p$, wherein said heterocycle is substituted with 0-3 $R^e$;

$R^e$ has a more particular value and is (independently at each occurrence) selected from the group consisting of —H, —F, —Cl, $C_{1-4}$ alkyl, —OH, —CO₂H, —NH₂, —CF₃, —OCF₃ and $C_{1-4}$ alkyloxy;

$R^f$ has a more particular value and is (independently at each occurrence) selected from the group consisting of H and $C_{1-4}$ alkyl;

n has a more particular value and is (independently at each occurrence) selected from the group consisting of 0, 1 and 2;

p has a more particular value and is (independently at each occurrence) selected from the group consisting of 0, 1 and 2;

r has a more particular value and is (independently at each occurrence) selected from the group consisting of 0, 1, 2, 3 and 4; and u has a more particular value and is (independently at each occurrence) selected from the group consisting of 0, 1 and 2;

provided that:

(1) in Formula (Ib), if R⁶ is —(CH₂)$_n$—$C_{3-6}$ cycloalkyl or —(CH₂)$_n$-phenyl, then A-1 is other than substituted biphenyl;

(2) in Formula (IIb), when A-1 is an unsubstituted phenyl or unsubstituted pyridyl, then R⁶ is other than an unsubstituted phenyl or unsubstituted pyridyl.

In a seventh aspect of the present invention is provided a compound of Formula (Ib) or (IIb), within the scope of the sixth aspect wherein:

ring A-1 has a more particular value and is (independently at each occurrence) substituted with 0-3 R¹ and selected from the group consisting of phenyl, pyridyl, imidazolyl and oxazolyl;

R⁶ is, independently at each occurrence selected from the group consisting of:

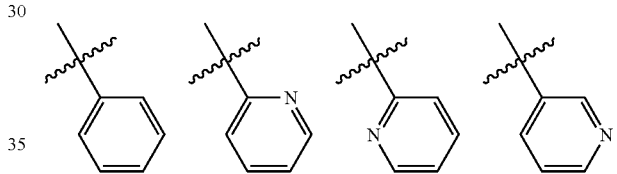

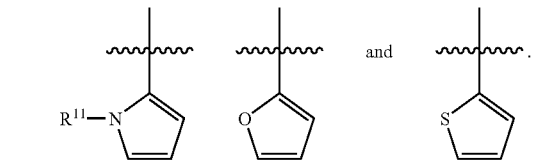

and substituted with 0-3 $R^{6a}$.

In an eighth aspect of the present invention is provided a compound of Formula (Ib) or (IIb), within the scope of the sixth aspect of the invention wherein:

ring A-1 has an even more particular value and is selected from the group consisting of is phenyl, 2-F-phenyl, 4-F-phenyl, 4-I-phenyl, 4-methyl-phenyl, 4-ethyl-phenyl, 4-isopropylphenyl, 4-n-butylphenyl, 4-sec-butylphenyl, 4-tert-butylphenyl, 4-CF₃-phenyl, 4-methoxyphenyl, 4-ethoxyphenyl, 4-n-butoxyphenyl, 4-n-heptoxyphenyl, 4-methylthiophenyl, 4-acetylphenyl, 4-difluoromethoxyphenyl, 4-trifluoromethoxy-phenyl, 4-trifluoromethylthiophenyl, 4-NMe₂-phenyl, 4-NO₂-phenyl, 4-cyanomethylphenyl, 2-methylcarbonyl-phenyl, 4-CO₂Et-phenyl, 4-(1-(diethylamino)-2-methylpropan-2-yl)-phenyl, 2,4-difluorophenyl, 2,5-difluorophenyl, 4-Cl-2-F-phenyl, 4-I-2-F-phenyl, biphenyl-4-yl, 4-benzylphenyl, 4-phenoxyphenyl, 4-phenylcarbonylphenyl, and

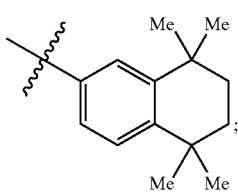

R⁶ has an even more particular value and is (independently at each occurrence) selected from the group consisting of phenyl, 2-ethyl-phenyl, 2-isopropylphenyl, 2-vinyl-phenyl, 2-trifluoromethyl-phenyl, 2-(methoxymethyl)-phenyl, 2-(t-butoxymethyl)-phenyl, 2-formyl-phenyl, 2-acetylphenyl, 4-NMe₂-phenyl, and biphenyl-2-yl; and R⁷ is H.

In a ninth aspect, the present invention is provided a compound selected from the exemplified examples of the present invention or a stereoisomer or pharmaceutically acceptable salt, solvate, or prodrug thereof, particularly a stereoisomer or pharmaceutically acceptable salt thereof.

In a tenth embodiment (aspect) of the invention, is provided a compound for any of the embodiments described as embodiments or aspects 1-9, wherein: ring A-1 is selected from the group consisting of 2-F-phenyl, 4-F-phenyl, 4-1-phenyl, 4-methyl-phenyl, 4-ethyl-phenyl, 4-isopropylphenyl, 4-n-butylphenyl, 4-sec-butylphenyl, 4-tert-butylphenyl, 4-CF₃-phenyl, 4-methoxyphenyl, 4-ethoxy-phenyl, 4-n-butoxyphenyl, 4-n-heptoxyphenyl, 4-methylthiophenyl, 4-acetylphenyl, 4-difluoromethoxy-phenyl, 4-trifluoromethoxy-phenyl, 4-trifluoromethylthio-phenyl, 4-NMe₂-phenyl, 4-NO₂-phenyl, 4-cyanomethylphenyl, 2-methylcarbonyl-phenyl, 4-CO₂Et-phenyl, 4-(1-(diethylamino)-2-methylpropan-2-yl)-phenyl, 2,4-difluorophenyl, 2,5-difluorophenyl, 4-Cl-2-F-phenyl, 4-I-2-F-phenyl, 4-benzylphenyl, 4-phenoxyphenyl, 4-phenylcarbonylphenyl, and

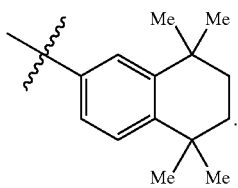

In an eleventh embodiment (aspect) of the invention is provided a compound for any of the embodiments described as embodiments or aspects 1-9, wherein: R⁶ is, independently at each occurrence, selected from the group consisting of phenyl, 2-ethyl-phenyl, 2-isopropylphenyl, 2-vinyl-phenyl, 2-trifluoromethyl-phenyl, 2-(methoxymethyl)-phenyl, 2-(t-butoxymethyl)-phenyl, 2-formyl-phenyl, 2-acetylphenyl, 4-NMe₂-phenyl, and biphenyl-2-yl.

In a twelfth embodiment (aspect) of the invention is provided a compound for any of the embodiments described as embodiments or aspects 1-9, as a pharmaceutical composition comprising a pharmaceutically acceptable carrier and at least one of the compounds of the present invention or a stereoisomer, tautomer, pharmaceutically acceptable salt, solvate, or prodrug thereof (particularly a stereoisomer, tautomer or pharmaceutically acceptable salt).

In a thirteenth embodiment (aspect) of the invention is provided a compound for any of the embodiments described as embodiments or aspects 1-9, as a pharmaceutical composition comprising a pharmaceutically acceptable carrier and a therapeutically effective amount of at least one of the compounds of the present invention or a stereoisomer, tautomer, pharmaceutically acceptable salt, solvate, or prodrug thereof (particularly a stereoisomer, tautomer or pharmaceutically acceptable salt).

In a fourteenth embodiment (aspect) of the invention is provided a novel process for making a compound of the present invention or a stereoisomer, tautomer, pharmaceutically acceptable salt, solvate or prodrug thereof (particularly a stereoisomer, tautomer or pharmaceutically acceptable salt).

In a fifteenth embodiment (aspect) of the invention is provided a novel intermediate for making a compound of the present invention or a stereoisomer, tautomer, pharmaceutically acceptable salt, solvate or prodrug thereof (particularly a stereoisomer, tautomer or pharmaceutically acceptable salt).

In a sixteenth embodiment (aspect) of the invention is provided a pharmaceutical composition further comprising at least one additional therapeutic agent selected from potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In a seventeenth embodiment (aspect) of the invention is provided a pharmaceutical composition wherein the additional therapeutic agent(s) is an antihypertensive agent selected from ACE inhibitors, AT-1 receptor antagonists, beta-adrenergic receptor antagonists, ETA receptor antagonists, dual ETA/AT-1 receptor antagonists, and vasopeptidase inhibitors, an antiarrythmic agent selected from IKur inhibitors, an anticoagulants selected from thrombin inhibitors, antithrombin-III activators, heparin co-factor II activators, factor VIIa inhibitors, factor Xa inhibitors, factor XIa inhibitors and kallikrein inhibitors, or antiplatelet agents selected from GPIIb/IIIa blockers, protease activated receptor (PAR-1) antagonists, phosphodiesterase-III inhibitors, other $P2Y_1$ antagonists, $P2Y_{12}$ antagonists, thromboxane receptor antagonists, cyclooxygense-1 inhibitors, and aspirin, or a combination thereof.

In an eighteenth embodiment (aspect) of the invention is provided a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In a nineteenth embodiment (aspect) of the invention is provided a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In a preferred embodiment, the present invention provides pharmaceutical composition, wherein the additional therapeutic agent(s) are an anti-platelet agent or a combination thereof.

In another preferred embodiment, the present invention provides a pharmaceutical composition, wherein the additional therapeutic agent is the anti-platelet agent selected from clopidogrel and aspirin, or a combination thereof.

In yet another preferred embodiment, the present invention provides a pharmaceutical composition, wherein the additional therapeutic agent is the anti-platelet agent clopidogrel.

In a particular embodiment, the present invention provides a method for modulation of platelet reactivity comprising administering to a patient in need of such treatment a therapeutically effective amount of at least one of the compounds of the present invention or a stereoisomer, tautomer, pharmaceutically acceptable salt, solvate, or prodrug thereof.

In another particular embodiment, the present invention provides a method for treating thrombotic or thromboembolic disorders comprising: administering to a patient in need of such treatment a therapeutically effective amount of at least one of the compounds of the present invention or a stereoisomer, tautomer, pharmaceutically acceptable salt, solvate, or prodrug thereof.

In still another particular embodiment, the thromboembolic disorder is selected from the group consisting of arterial cardiovascular thromboembolic disorders, venous cardiovascular thromboembolic disorders, arterial cerebrovascular thromboembolic disorders, venous cerebrovascular thromboembolic disorders, and thromboembolic disorders in the chambers of the heart.

In another particular embodiment, the thromboembolic disorder is selected from the group consisting of unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In yet another embodiment, the present invention provides a method of treating a patient in need of thromboembolic disorder treatment, comprising: administering a compound of the present invention or a stereoisomer, tautomer, pharmaceutically acceptable salt, solvate, or prodrug form thereof in an amount effective to treat a thromboembolic disorder.

In still another embodiment, the present invention provides a method, comprising: administering a compound of the present invention or a stereoisomer, tautomer, pharmaceutically acceptable salt, solvate, or prodrug thereof in an amount effective to treat a thrombotic or thromboembolic disorder.

In still another embodiment, the present invention provides a compound of the present invention for use in therapy for treating a thrombotic and thromboembolic disorder.

In still another embodiment, the present invention also provides the use of a compound of the present invention for the manufacture of a medicament for the treatment of a thrombotic or thromboembolic disorder.

In a further embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used for the treatment of a thrombotic or thromboembolic disorder.

In yet another preferred embodiment, the present invention provides a novel article of manufacture, further comprising: (d) a second container; wherein components (a) and (b) are located within the second container and component (c) is located within or outside of the second container.

In still another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used in combination with a second therapeutic agent to treat a thrombotic or thromboembolic disorder.

In a final preferred embodiment, the present invention provides a novel article of manufacture, further comprising: (d) a second container; wherein components (a) and (b) are located within the second container and component (c) is located within or outside of the second container.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials or optically active catalysts. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention. The inventive compounds may be in the free or hydrate form.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. When a ring system (e.g., carbocyclic or heterocyclic) is said to be substituted with a carbonyl group or a double bond, it is intended that the carbon atom of the carbonyl group or one carbon atom of the double bond be part of (i.e., within) the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative. In cases wherein there are quaternary carbon atoms on compounds of the present invention, these can be replaced by silicone atoms, provided they do not form Si—N or Si—O bond.

When any variable occurs more than one time in any constituent or formula for a compound, its definition at each occurrence is independent of its definition at every other occurrence unless stated otherwise. Thus, for example, if a group is shown to be substituted with 0-3 $R^1$, then said group may optionally be substituted with up to three $R^1$ groups and $R^1$ at each occurrence is selected independently from the definition of $R^1$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

Bonds are understood to have their normal and customary valences unless otherwise shown. For convenience, substituents may be represented with or without the bonds being shown. Thus, for example, hydrogen may be represented as "H" or as "—H", etc.

As used herein, "alkyl" or "alkylene" is intended to include both branched and straight-chain saturated aliphatic hydrocarbon groups having the specified number of carbon atoms. For example, "$C_1$-$C_{10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

"Alkenyl" or "alkenylene" is intended to include hydrocarbon chains of either a straight or branched configuration having the specified number of carbon atoms and one or more unsaturated carbon-carbon bonds which may occur in any stable point along the chain. For example, "$C_2$-$C_6$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration and one or more carbon-carbon triple bonds which may occur in any stable point along the chain. For example, "$C_2$-$C_6$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like.

"Alkoxy" or "alkyloxy" represents an alkyl group as defined above with the indicated number of carbon atoms attached through an oxygen bridge. For example, "$C_1$-$C_6$ alkoxy" (or alkyloxy), is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group as defined above with the indicated number of carbon atoms attached through a sulphur bridge; for example methyl-S—, ethyl-S—, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$-$C_6$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluoroethoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

As used herein, "carbocycle" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred carbocycles, unless otherwise specified, are cyclopropyl, cyclobutyl, cyclopentyl, cyclohexyl, phenyl, naphthyl, and indanyl. When the term "carbocycle" is used, it is intended to include "aryl".

As used herein, the term "bicyclic carbocycle" or "bicyclic carbocyclic group" is intended to mean a stable 9- or 10-membered carbocyclic ring system which contains two fused rings and consists of carbon atoms. Of the two fused rings, one ring is a benzo ring fused to a second ring; and the second ring is a 5 or 6 membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

As used herein, the term "aryl", "$C_6$-$C_{10}$ aryl" or "aromatic residue", is intended to mean an aromatic moiety containing, if specified, the specified number of carbon atoms; for example phenyl or naphthyl. Unless otherwise specified, "aryl", "$C_6$-$C_{10}$ aryl" or "aromatic residue" may be unsubstituted or substituted with 0 to 3 groups selected from H, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle" or "heterocyclic group" is intended to mean a stable 3, 4, 5, 6, or 7-membered monocyclic or bicyclic or 7, 8, 9, 10, 11, 12, 13, or 14-membered bicyclic or tricyclic heterocyclic ring which is saturated, partially unsaturated or fully unsaturated, and which consists of carbon atoms and 1, 2, 3 or 4 heteroatoms independently selected from the group consisting of N, O and S; and including any bicyclic group in which any of the above-defined heterocyclic rings is fused to a benzene ring. The nitrogen and sulfur heteroatoms may optionally be oxidized to —NO—, —SO—, or —$SO_2$—. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen atom in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5 or 6-membered monocyclic aromatic ring comprising a 5 membered heteroaryl ring, a 6-membered heteroaryl ring or a benzo ring, each fused to a second ring. The second ring is a 5 or 6 membered monocyclic ring which is saturated, partially unsaturated, or unsaturated, and comprises a 5 membered heterocycle, a 6 membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinoline, 2,3-dihydro-benzofuranyl, chromanyl, 1,2,3,4-tetrahydro-quinoxaline, and 1,2,3,4-tetrahydro-quinazoline.

Also included are fused ring and spiro compounds containing, for example, the above carbocycles or heterocycles.

Bridged rings are also included in the definition of carbocycle or heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Greene and Wuts, "Protective Groups in Organic Synthesis" John Wiley & Sons, New York (1991) and "The Peptides: Analysis, Synthesis, Biology, Vol. 3, Academic Press, New York (1981), the disclosure of which is hereby incorporated by reference. Examples of amine protecting groups include, but are not limited to, the following: (Fmoc); (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, the disclosure of which is hereby incorporated by reference.

Isotopically labeled compounds of the present invention, i.e., wherein one or more of the atoms described are replaced by an isotope of that atom (e.g., C replaced by $^{13}$C or by $^{14}$C; and isotopes of hydrogen include tritium and deuterium), are also provided herein. Such compounds have a variety of potential uses, e.g., as standards and reagents in determining the ability of a potential pharmaceutical to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 99% compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, S(O)$_2$H, or S(O)H group.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs*, edited by H. Bundgaard, (Elsevier, 1985), and *Methods in Enzymology*, Vol. 112, at pp. 309-396, edited by K. Widder, et. al. (Academic Press, 1985);

b) *A Textbook of Drug Design and Development*, edited by Krosgaard-Larsen and H. Bundgaard, Chapter 5, "Design and Application of Prodrugs," by H. Bundgaard, at pp. 113-191 (1991);

c) H. Bundgaard, *Advanced Drug Delivery Reviews*, Vol. 8, p. 1-38 (1992);

d) H. Bundgaard, et al., *Journal of Pharmaceutical Sciences*, Vol. 77, p. 285 (1988); and e) N. Kakeya, et. al., *Chem Phar Bull.*, Vol. 32, p. 692 (1984).

Compounds containing a carboxy group can form physiologically hydrolyzable esters which serve as prodrugs by being hydrolyzed in the body to yield compounds of the present invention per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$ alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl, and other well known physiologically hydrolyzable esters used, for example, in the penicillin and cephalosporin arts. Such esters may be prepared by conventional techniques known in the art.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates and the like. Methods of solvation are generally known in the art.

As used herein, the term "patient" encompasses all mammalian species.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination with other active ingredients to inhibit $P2Y_1$ or to treat the conditions or disorders listed herein. When applied to a combination, the term refers to combined amounts of the active ingredients that result in the therapeutic effect, whether administered in combination, serially or simultaneously. The combination of compounds is preferably a synergistic combination. Synergy, as described, for example, by Chou and Talalay, *Adv. Enzyme Regul.* 1984, 22:27-55, occurs when the effect (in this case, inhibition of $P2Y_1$) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

The term "pharmaceutical composition" means a composition comprising a compound of the invention in combination with at least one additional pharmaceutical carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 18th ed., 1990, which is incorporated herein by reference in its entirety.

Abbreviations as used herein, are defined as follows: "1×" for once, "2×" for twice, "3×" for thrice or three times, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "M" for molar, "mmol" for millimole or millimoles, "min" for minute or minutes, "h" for hour or hours, "rt" for room temperature, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "LC-MS" for liquid chromatography mass spectrometry, "HPLC" for high pressure liquid chromatography, "RP HPLC" for reverse phase HPLC, "TLC" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, "tlc" for thin layer chromatography, and "α", "β", "R", "S", "E", and "Z" are stereochemical designations familiar to one skilled in the art.

| | |
|---|---|
| Me | methyl |
| Et | ethyl |
| MeOH | methanol |
| EtOH | ethanol |
| i-PrOH | isopropanol |
| Ph | phenyl |
| Bn | benzyl |
| Bu | butyl |
| iBu or i-Bu | isobutyl |
| Pr | propyl |
| iPr or i-Pr | isopropyl |
| t-Bu | tertiary butyl |
| AcOH | acetic acid |
| BINAP | 2,2'-bis(diphenylphosphino)-1,1'-binaphthyl |
| EtOAc | ethyl acetate |
| ADP | adenosine diphosphate |
| 2MeS-ADP | 2 methylthio adenosine diphosphate |
| cDNA | complimentary DNA |
| DCC | dicyclohexylcarbodiimide |
| DCE | 1,2 dichloroethane |
| DCM | dichloromethane |
| DEAD | diethyl azodicarboxylate |
| DIC or DIPCDI | diisopropylcarbodiimide |
| DIEA | diethylpropyl amine |
| DMAP | 4-dimethylaminopyridine |
| DMEM | Dulbecco's modified Eagle media |
| DMF | dimethyl formamide |
| DMSO | dimethyl sulfoxide |
| EDC (or EDC•HCl) or EDCI (or EDCI•HCl) | 3-ethyl-3'-(dimethylamino)propyl-carbodiimide hydrochloride (or 1-(3-dimethylaminopropyl)- |

| | |
|---|---|
| or EDAC | 3-ethylcarbodiimide hydrochloride) |
| EDTA | ethylenediaminetetraacetic acid |
| FBS | Fetal Bovine Serum |
| HEPES | 4-(2-hydroxyethyl)piperaxine-1-ethanesulfonic acid |
| LDA | lithium diisopropylamide |
| mCPBA or MCPBA | meta-chloroperbenzoic acid |
| OAc | acetate |
| OMs | mesylate, methanesulfoate |
| OTf | triflate, trifluoromethanesulfonate |
| OTs | tosylate, para-toluenesulfonate |
| D-PBS | Dulbecco's Phosphate Buffered Saline |
| Pd/C | palladium on carbon |
| SCX | Strong Cation Exchanger |
| THF | tetrahydrofuran |
| TFA | trifluoroacetic acid |
| TRIS | tris (hydroxymethyl) aminomethane |

Solution ratios express a volume relationship, unless stated otherwise. NMR chemical shifts (δ) are reported in parts per million. Flash chromatography was carried out on silica gel according to Still's method (Still, W. C. et al. *J. Org. Chem.* 1978, 43, 2923). Alternatively, flash chromatography was carried out on an ISCO CombiFlash™ System Sq16x using prepacked $SiO_2$ cartridges eluted with gradients of hexanes and ethyl acetate.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C. *Comprehensive Organic Transformations*, VCH: New York, 1989. Preferred methods include, but are not limited to, those described below. All references cited herein are hereby incorporated in their entirety by reference.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety by reference.

U.S. Published Patent Application No. US 2005/0261244 A1 and U.S. Published Patent Application No. US 2005/0203146 A1, disclose preparations of starting materials and intermediates which can be utilized in making compounds of the present invention and are incorporated herein by reference as to those preparations.

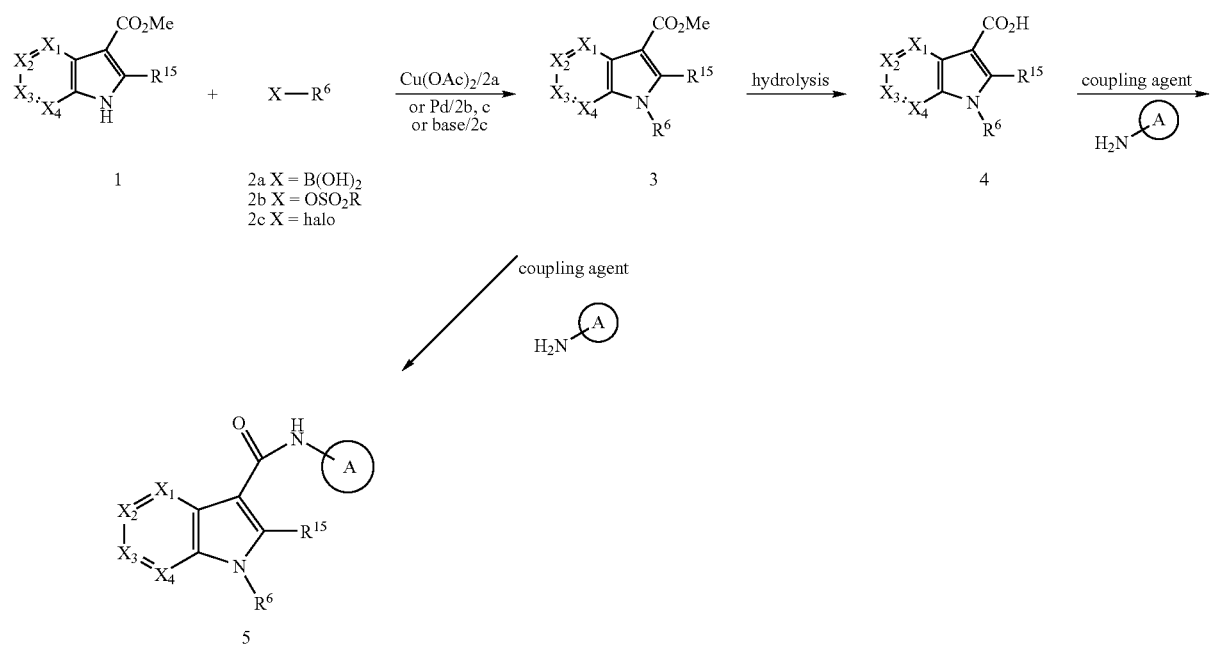

Compounds of Formula I where Y=—C(O)—NH may be made by methods known to those skilled in the art. One example of such a method where "5" is a compound of Formula I where Y=—C(O)—NH is shown in Scheme 1.

Compounds of formula 5 may be synthesized according to Scheme 1 with the use of materials accessed from commercial sources or synthesized using known methodology found in public literature or a contemporary reference (for example, Sundberg, R. J. *Indoles*; Academic Press; San Diego, 1996.). Known methods for indole N-arylation for conversion of 1 to 3 include the Chan-Lam Cu catalyzed N-arylation utilizing boronic acids 2a, Pd catalyzed coupling using aryl sulfonates 2b or halides 2c, or via Cu$^{+1}$ catalyzed coupling (Ullmann rxn) with aryl halides. Indole 1 may also be alkylated using alkyl halides and treatment with appropriate base. Hydrolysis yields 4 followed by coupling with nitrogen substrate gives compound 5. Alternatively 3 may be converted directly to 5 with the aid of a coupling agent such as Me$_3$Al.

Compounds of Formula I where Y=—C(O)—NH may also be made by other methods such as the method shown in Scheme 2.

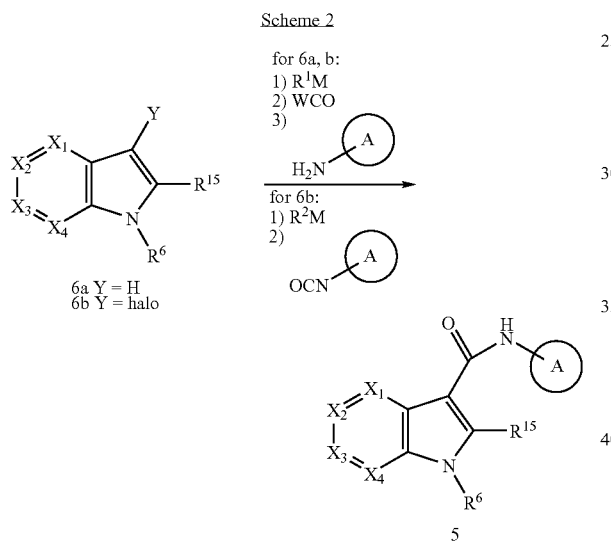

According to Scheme 2, 6a may be treated with an organometallic reagent (R$^1$M; R$^1$=Et$_2$; M=AlCl) and acyl halide equivalent (W=Cl$_2$) followed by nitrogen substrate to yield 5. 6b may be treated with an organometallic reagent (R$^1$M=Pd (Ph$_3$P)$_4$) and acyl halide equivalent (W=null) followed by nitrogen substrate to yield 5. 6b may be treated with an organometallic reagent (R$^1$M=BuLi or alkyl-Mg-halide) followed by isocyantate substrate to yield 5 Formula I with Y=—C(O)—NH.

Compounds of the present invention of Formula I where Y is other than —C(O)—NH can be prepared by methods known to those skilled in the art such as by using Scheme 1 or 2 with appropriate substitutions of raw materials (for example, suitable choices for R$^{6a}$). Such methods can be observed, for example, in one of the methods described in articles for copper-mediated C(aryl)-O; C(aryl)-N and C(aryl)-S bond formation by Ley, S. V. and Thomas, A. W. in *Angew. Chem. Int. Ed.* 2003, 42, 5400-5449 or Chan, D. M. and Lam, P. Y. S. in *Boronic Acids*, Ed Hall, D. G. p 205-240, Wiley-VCH 2005. Alternatively other organometalloides such as siloxanes, stannanes or organobismuth reagents can be employed in place of boronic acid derivatives. Additionally, some of the starting materials are available through commercial sources such as Aldrich (Milwaukee, Wis.).

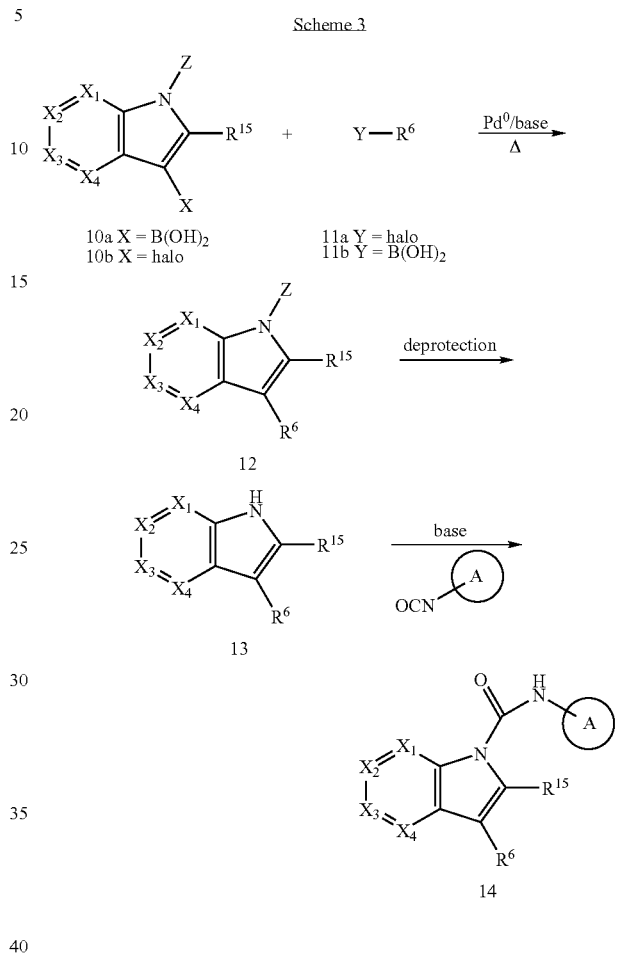

Compounds of formula 14 (Formula II where Y=—C(O)—NH) may be synthesized according to Scheme 3. 3-Boronylated (10a) or 3-halogenated (10b) indoles may be coupled with the appropriate reactant (11b or 11a, respectively) in the presence of activating metal such as palladium(0) to afford compound 12. After removal of any indole protecting group (Z) generation of indole salt with appropriate base and coupling with isocyante or other urea forming reagent (Gallou, I. et al. *Journal of Organic Chemistry* 2005, 70, 6960-6963) will yield compound 14.

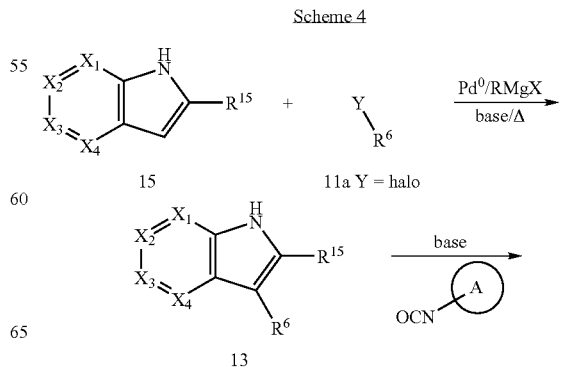

-continued

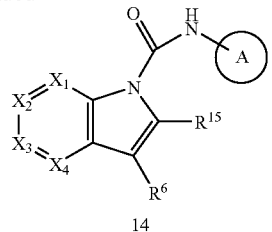

14

Alternatively, compounds of formula 14 may also be synthesized according to Scheme 4. Indoles 15 may be coupled with the appropriate reactant (11a) in the presence of activating metal such as palladium(0) and Grignard reagents (Lane, B. S. et al. *J. Am. Chem. Soc.* 2005, 127, 8050-8057) to afford compound 13. As before generation of indole salt with appropriate base and coupling with isocyante or other urea forming reagent will yield compound 14.

Compounds of the present invention of Formula II where Y is other than —C(O)—NH can be prepared by methods known to those skilled in the art such as by using Scheme 3 or 4 with appropritate substitutions of raw materials (for example, suitable choices for $R^{6a}$).

In the following experimental procedures, solution ratios express a volume relationship, unless stated otherwise. NMR chemical shifts (δ) are reported in parts per million.

Products were analyzed by reverse phase analytical HPLC carried out on a Shimadzu Analytical HPLC system running DiscoveryVP software using one of the methods outlined below:

Method A: Phenomenex Gemini 4.6×50 mm 5 um C18 column, Gradient solvent system: from 100% A: 0% B to 0% A: 100% B (A=98% $H_2O$/2% Acetonitrile+10 mM $NH_4OAc$); (B=90% Acetonitrile/10% $H_2O$+10 mM $NH_4OAc$) for 4 min; with 4.0 mL/min flow rate and a 1 min. hold, an ultra violet (UV) detector set at 220 nm.

Method B: Zorbax SB C18 4.6×75 mm column, Gradient solvent system: from 100% A: 0% B to 0% A: 100% B (A=90% $H_2O$/10% MeOH+0.2% $H_3PO_4$); (B=90% MeOH/10% $H_2O$+0.2% $H_3PO_4$) for 8 min; with 2.5 mL/min flow rate and a 3 min. hold, an ultra violet (UV) detector set at 220 nm.

Method C: Sunfire 4.6×150 mm 3.5 um column, Gradient solvent system: from 90% A: 10% B to 0% A: 100% B (A=95% $H_2O$/5% Acetonitrile+0.05% TFA); (B=95% Acetonitrile/5% $H_2O$+0.05% TFA) for 10 min, with 2.0 mL/min flow rate and a 5 min. hold, an ultra violet (UV) detector set at 220 nm and 254 nm.

Method D: Phenomenex Luna 4.6×50 mm C18 column, Gradient solvent system: from 100% A: 0% B to 0% A: 100% B (A=90% $H_2O$/10% Acetonitrile+10 mM $NH_4OAc$); (B=90% Acetonitrile/10% $H_2O$+10 mM $NH_4OAc$) for 4 min; with 4.0 mL/min flow rate and a 1 min. hold, an ultra violet (UV) detector set at 220 nm.

Method E: Phenomenex Luna 4.6×30 mm C18 column, Gradient solvent system: from 100% A: 0% B to 0% A: 100% B (A=90% $H_2O$/10% Acetonitrile+5 mM $NH_4OAc$); (B=90% Acetonitrile/10% $H_2O$+5 mM $NH_4OAc$) for 2 min; with 4.0 mL/min flow rate and a 1 min. hold, an ultra violet (UV) detector set at 220 nm.

Purification of intermediates and final products was carried out via either normal or reverse phase chromatography. Normal phase chromatography was carried out on an ISCO CombiFlash™ System Sq16x using prepacked $SiO_2$ cartridges eluted with gradients of hexanes and ethyl acetate. Reverse phase preparative HPLC was carried out using a Shimadzu Preparative HPLC system running DiscoveryVP software on a Shim-PackVP-ODS column (50L×20 mm) at 20 mL/min, 6 min gradient 100% A to 100% B with the solvent system used for the analytical. LCMS were obtained on a Shimadzu HPLC system running DiscoveryVP software, coupled with a Waters Model PlatformLC mass spectrometer running MassLynx version 3.5 software using the same column and conditions as utilized for analytical described above.

EXAMPLES

The following Examples are offered as illustrative as a partial scope of the invention and are not meant to be limiting of the scope of the invention. Unless otherwise indicated, they have been prepared, isolated and characterized using the methods disclosed herein. The abbreviations used herein are defined above. Structures and data for Examples 1-48 are given in Table 1. The LC method used is listed in the Tables and is selected from the methods described above under Methods A-E. Structures and data for the other Examples are contained in the text of the description for those Examples.

Example 1

3-(2-isopropylphenyl)-N-phenyl-1H-indole-1-carboxamide

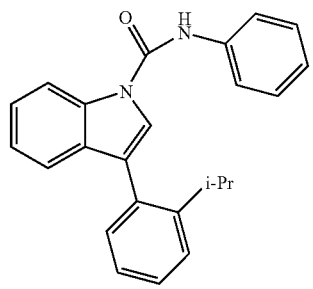

3-Bromo-1-(phenylsulfonyl)-1H-indole (7.45 g, 22.2 mmol), 2-isopropylbenzene boronic acid (4.00 g, 24.4 mmol), tetrakis(triphenylphosphine)palladium (0) (769 mg, 0.67 mmol) and sodium carbonate (7.05 g, 66.5 mmol) were combined in a round bottomed flask and placed under an argon atmosphere. Degassed solvent (3:1:1 toluene/ethanol/water) (100 mL) was added and the contents were heated to 80° C. for 14 h. Upon completion of the reaction, as determined by TLC, the phases were separated, the aqueous phase was extracted three times with 20 mL ethyl acetate and all the organic phases were combined, washed once with water (20 mL) and once with brine (20 mL). The organic phase was dried over $Na_2SO_4$, filtered, and the solvent was evaporated under reduced pressure to yield a dark residue which was purified by silica gel chromatography eluting with a gradient of ethyl acetate/hexanes to yield 3-(2-isopropylphenyl)-1-(phenylsulfonyl)-1H-indole (6.79 g, 82%) as a glassine solid. LC/MS (ESI+) 376.2 (M+H)⁺. 3-(2-Isopropylphenyl)-1-(phenylsulfonyl)-1H-indole (119 mg, 0.317 mmol) was combined with anhydrous tetrahydrofuran (2 mL) and tetra-n-butylammonium fluoride (1 M in THF, 1.3 mL) and heated to reflux for 14 h. Upon completion as observed by analysis by LC/MS the reaction was diluted with methanol (1 mL) and the solvent was evaporated under reduced pressure to yield a residue which was purified by silica gel chromatography eluting with a gradient of ethyl acetate/hexanes to yield 3-(2-isopropylphenyl)-1H-indole (67 mg, 90%) as a colorless glassine solid. LC/MS (ESI+) 236.23 (M+H)+. To 3-(2-isopropylphenyl)-1H-indole (23 mg, 0.10 mmol) in anhydrous tetrahydrofuran (1 mL) was added sodium bis(trimethylsilyl) amide solution (0.1 mL, 0.1 mmol, 1 M in tetrahydrofuran) and stirred for 15 min at ambient temperature. Isocyanatobenzene (0.1 mmol, 1.0 eq.) in THF (1 mL) was added and the reaction was stirred at ambient temperature. Upon completion as observed by analysis by LC/MS the reaction was diluted with methanol (1 mL) and the solvent was evaporated under reduced pressure to yield a residue which was purified by reverse phase HPLC chromatography eluting with a gradient of methanol/water to yield Example 1 (7.8 mg, 22%) as a colorless solid. LC/MS (ESI+) 355.23 (M+H)+.

The compounds in Table 1 were prepared according to the General Procedure A (targeted to compounds of Formula II) described below and duplicated in Scheme 5 substituting the appropriate aryl boronic acid ($Ar^1B(OH)_2$) and aryl isocyanate ($Ar^2NCO$) to achieve the named compound. $Ar^1$ is for the $R^6$ group and $Ar^2$ is for the A group (optionally referred to as A-1 since it is a ring in Scheme 5).

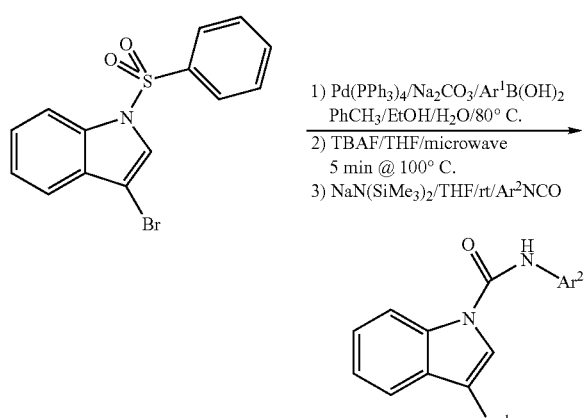

Scheme 5

1) Pd(PPh$_3$)$_4$/Na$_2$CO$_3$/Ar$^1$B(OH)$_2$
   PhCH$_3$/EtOH/H$_2$O/80° C.
2) TBAF/THF/microwave
   5 min @ 100° C.
3) NaN(SiMe$_3$)$_2$/THF/rt/Ar$^2$NCO General Procedure A: 3-Bromo-1-(phenylsulfonyl)-1H-indole (176 mg, 0.50 mmol), aryl boronic acid ($Ar^1B(OH)_2$) (0.55 mmol), tetrakis(triphenylphosphine)palladium (0) (59 mg, 0.050 mmol) and sodium carbonate (159 mg, 1.50 mmol) are combined in a screw capped test tube equipped with a septa closure and a stir bar and placed under an argon atmosphere. Degassed solvent (3:1:1 toluene/ethanol/water 2.5 mL total volume) is added via syringe and the contents are heated to 80° C. for 14 h. Upon completion of the reaction, as determined by LC, the reactions are diluted with 3 mL each of ethyl acetate and water and phases are separated, the aqueous extracted once with 3 mL ethyl acetate the organic phases are combined, washed once with water (3 mL) and once with brine (3 mL). The organic phase is dried over Na$_2$SO$_4$, filtered, and the solvent is evaporated under reduced pressure to yield a dark residue which is purified by silica gel chromatography eluting with a gradient of ethyl acetate/hexanes to yield the 3-Ar$^1$-1-(phenylsulfonyl)-1H-indole. 3-Ar$^1$-1-(phenylsulfonyl)-1H-indole is combined with anhydrous tetrahydrofuran (1 mL) and tetra-n-butylammonium fluoride (1 M in THF, 6.0 eq) in a septum capped microwave vial and heated to 100° C. for 8 min. Upon completion as observed by analysis by LC/MS the reaction is diluted with methanol (2 mL) and the solvent is evaporated under reduced pressure to yield a residue which is purified by silica gel chromatography eluting with a gradient of ethyl acetate/hexanes to yield 3-Ar$^1$-1H-indoles. To 3-Ar$^1$-1H-indoles (0.10 mmol) in anhydrous tetrahydrofuran (1 mL) is added sodium bis(trimethylsilyl) amide solution (0.1 mL, 0.1 mmol, 1 M in THF) and stirred for 15 min at ambient temperature. Aryl isocyante (Ar$^2$NCO) (0.1 mmol, 1.0 eq.) in THF (1 mL) is added and the reaction stirred at ambient temperature. Upon completion as observed by analysis by LC/MS the reaction is diluted with methanol (1 mL) and the solvent is evaporated under reduced pressure to yield a residue which is purified by either silica gel flash chromatography eluting with a gradient of ethyl acetate/hexanes or by reverse phase HPLC chromatography eluting with a gradient of methanol/water or acetonitrile/water to yield the title compound.

TABLE 1

| Example | Structure | Name | Observed MS ion | LC Retention Time (minutes) | LC Analysis Method |
|---------|-----------|------|-----------------|-----------------------------|--------------------|
| 1 | 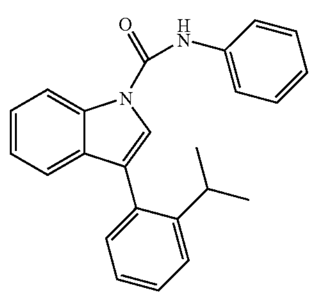 | 3-(2-isopropylphenyl)-N-phenyl-1H-indole-1-carboxamide | 355.23 | 3.98 | A |

TABLE 1-continued

| Example | Structure | Name | Observed MS ion | LC Retention Time (minutes) | LC Analysis Method |
|---|---|---|---|---|---|
| 2 | 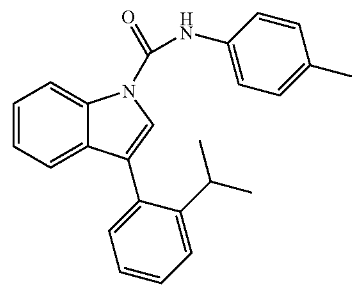 | 3-(2-isopropylphenyl)-N-p-tolyl-1H-indole-1-carboxamide | 369.25 | 4.11 | A |
| 3 | 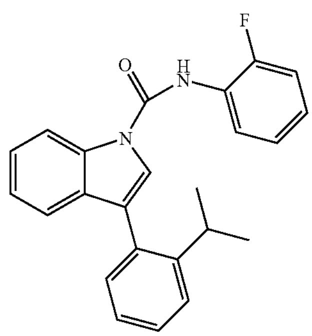 | N-(2-fluorophenyl)-3-(2-isopropylphenyl)-1H-indole-1-carboxamide | 373.21 | 3.95 | A |
| 4 | 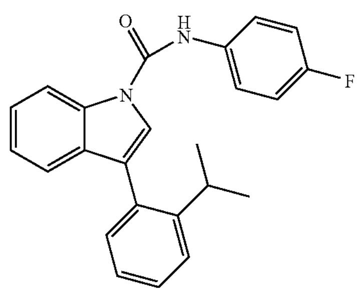 | N-(4-fluorophenyl)-3-(2-isopropylphenyl)-1H-indole-1-carboxamide | 373.23 | 4.01 | A |
| 5 | 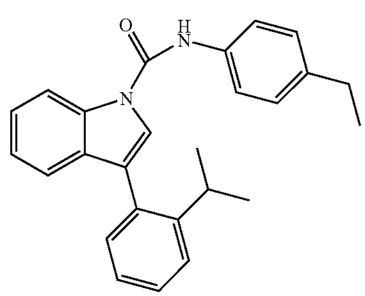 | N-(4-ethylphenyl)-3-(2-isopropylphenyl)-1H-indole-1-carboxamide | 383.26 | 4.24 | A |
| 6 | 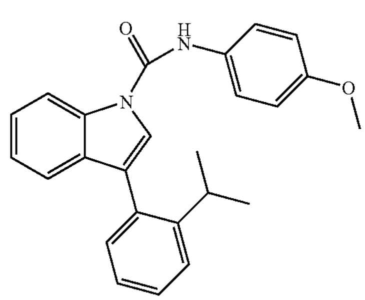 | 3-(2-isopropylphenyl)-N-(4-methoxyphenyl)-1H-indole-1-carboxamide | 385.25 | 3.93 | A |

TABLE 1-continued

| Example | Structure | Name | Observed MS ion | LC Retention Time (minutes) | LC Analysis Method |
|---|---|---|---|---|---|
| 7 | 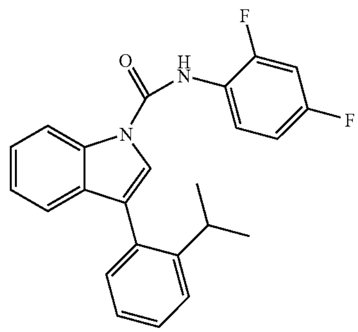 | N-(2,4-difluorophenyl)-3-(2-isopropylphenyl)-1H-indole-1-carboxamide | 391.24 | 3.95 | A |
| 8 | 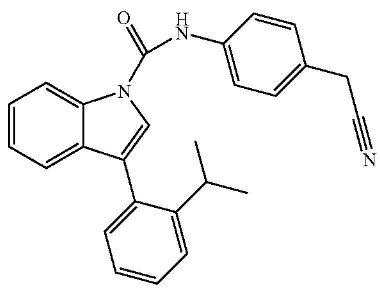 | N-(4-(cyanomethyl)phenyl)-3-(2-isopropylphenyl)-1H-indole-1-carboxamide | 394.24 | 3.82 | A |
| 9 | 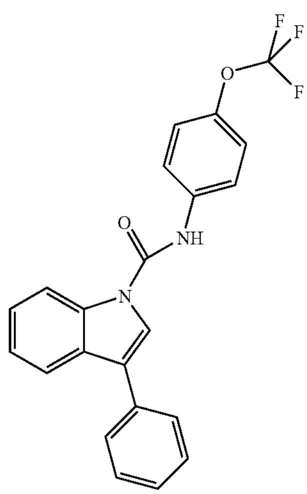 | 3-phenyl-N-(4-(trifluoromethoxy)phenyl)-1H-indole-1-carboxamide | 397.10 | 9.433 | B |
| 10 | 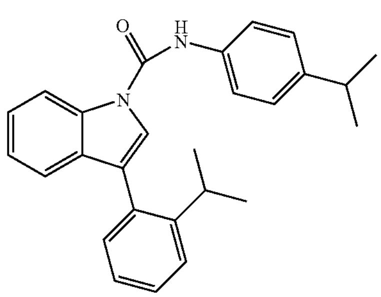 | 3-(2-isopropylphenyl)-N-(4-isopropylphenyl)-1H-indole-1-carboxamide | 397.30 | 4.35 | A |

TABLE 1-continued

| Example | Structure | Name | Observed MS ion | LC Retention Time (minutes) | LC Analysis Method |
|---|---|---|---|---|---|
| 11 | 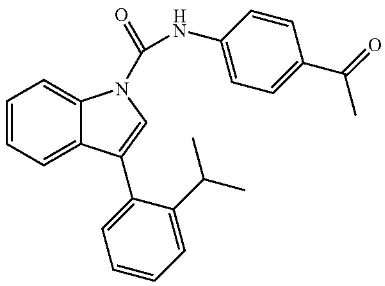 | N-(4-acetylphenyl)-3-(2-isopropylphenyl)-1H-indole-1-carboxamide | 397.24 | 3.88 | A |
| 12 | 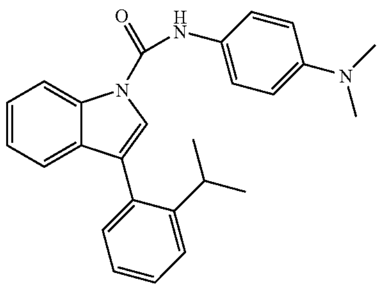 | N-(4-(dimethylamino)phenyl)-3-(2-isopropylphenyl)-1H-indole-1-carboxamide 2,2,2-trifluoroacetic acid salt | 398.26 | 4.03 | A |
| 13 | 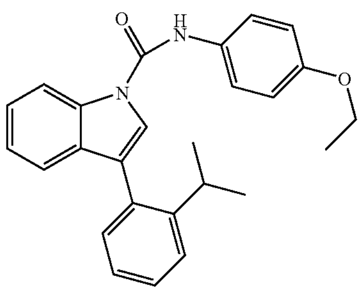 | N-(4-ethoxyphenyl)-3-(2-isopropylphenyl)-1H-indole-1-carboxamide | 399.27 | 4.08 | A |
| 14 | 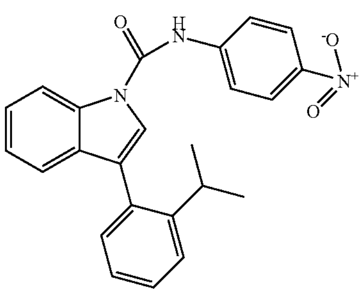 | 3-(2-isopropylphenyl)-N-(4-nitrophenyl)-1H-indole-1-carboxamide | 400.25 | 4.10 | A |
| 15 | 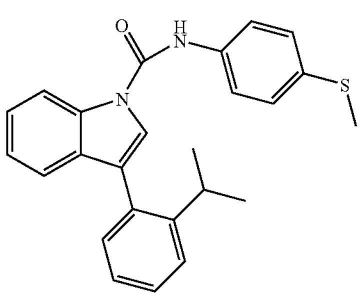 | 3-(2-isopropylphenyl)-N-(4-(methylthio)phenyl)-1H-indole-1-carboxamide | 401.22 | 4.16 | A |

TABLE 1-continued

| Example | Structure | Name | Observed MS ion | LC Retention Time (minutes) | LC Analysis Method |
|---|---|---|---|---|---|
| 16 | 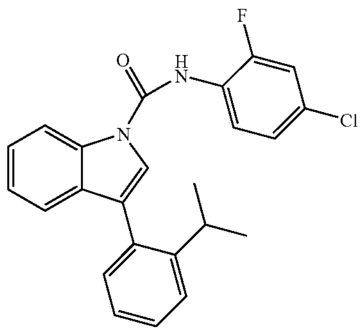 | N-(4-chloro-2-fluorophenyl)-3-(2-isopropylphenyl)-1H-indole 1-carboxamide | 407.16 | 4.15 | A |
| 17 | 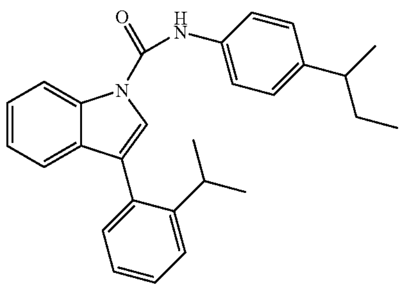 | N-(4-sec-butylphenyl)-3-(2-isopropylphenyl)-1H-indole-1-carboxamide | 411.32 | 4.49 | A |
| 18 | 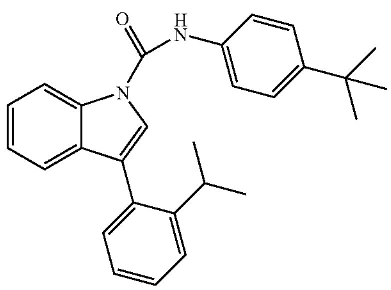 | N-(4-tert-butylphenyl)-3-(2-isopropylphenyl)-1H-indole-1-carboxamide | 411.31 | 4.45 | A |
| 19 | 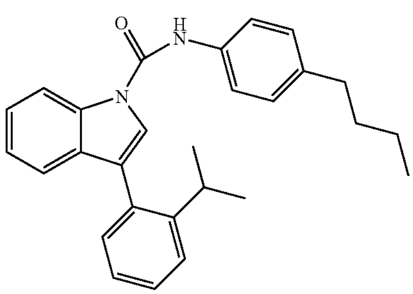 | N-(4-butylphenyl)-3-(2-isopropylphenyl)-1H-indole-1-carboxamide | 411.29 | 4.56 | A |
| 20 | 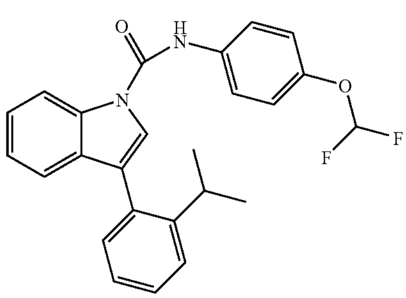 | N-(4-(difluoromethoxy)phenyl)-3-(2-isopropylphenyl)-1H-indole-1-carboxamide | 421.22 | 4.05 | A |

TABLE 1-continued

| Example | Structure | Name | Observed MS ion | LC Retention Time (minutes) | LC Analysis Method |
|---|---|---|---|---|---|
| 21 | 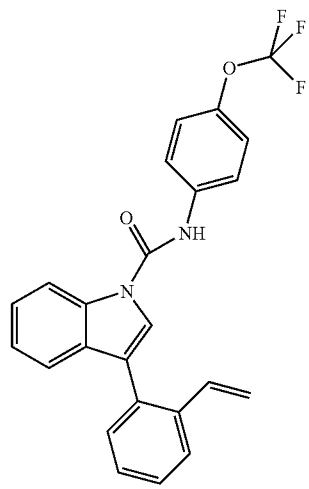 | N-(4-(trifluoromethoxy)phenyl)-3-(2-vinylphenyl)-1H-indole-1-carboxamide | 423.10 | 9.671 | B |
| 22 | 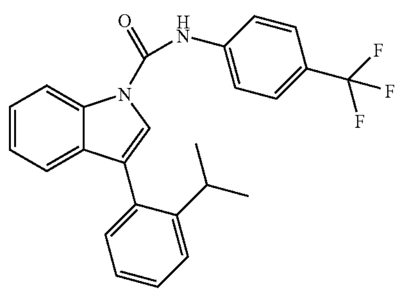 | 3-(2-isopropylphenyl)-N-(4-(trifluoromethyl)phenyl)-1H-indole-1-carboxamide | 423.26 | 4.26 | A |
| 23 | 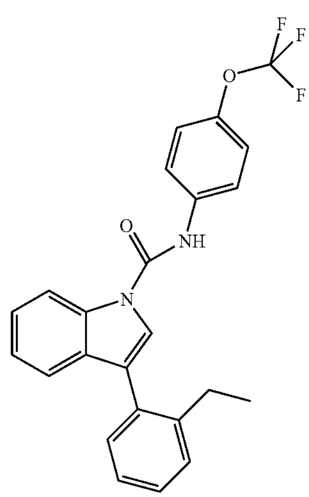 | 3-(2-ethylphenyl)-N-(4-(trifluoromethoxy)phenyl)-1H-indole-1-carboxamide | 425.10 | 9.753 | B |

TABLE 1-continued

| Example | Structure | Name | Observed MS ion | LC Retention Time (minutes) | LC Analysis Method |
|---|---|---|---|---|---|
| 24 | 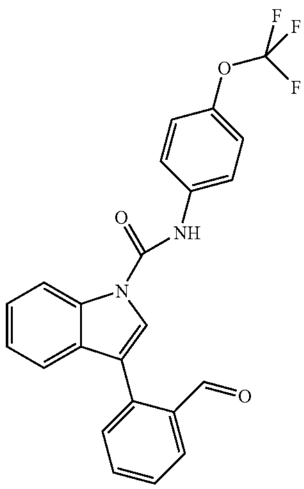 | 3-(2-formylphenyl)-N-(4-(trifluoromethoxy)phenyl)-1H-indole-1-carboxamide | 425.10 | 9.174 | B |
| 25 | 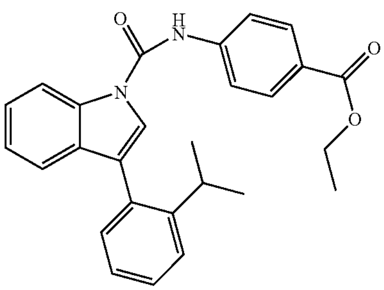 | ethyl 4-(3-(2-isopropylphenyl)-1H-indole-1-carboxamido)benzoate | 427.25 | 4.20 | A |
| 26 | 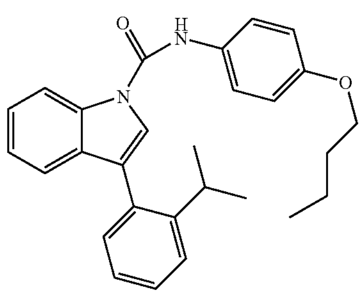 | N-(4-butoxyphenyl)-3-(2-isopropylphenyl)-1H-indole-1-carboxamide | 427.31 | 4.38 | A |
| 27 | 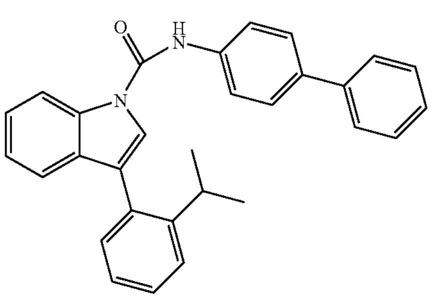 | N-(biphenyl-4-yl)-3-(2-isopropylphenyl)-1H-indole-1-carboxamide | 431.26 | 4.40 | A |

TABLE 1-continued

| Example | Structure | Name | Observed MS ion | LC Retention Time (minutes) | LC Analysis Method |
|---|---|---|---|---|---|
| 28 | 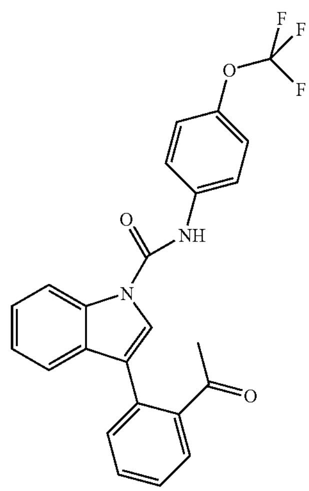 | 3-(2-acetylphenyl)-N-(4-(trifluoromethoxy)phenyl)-1H-indole-1-carboxamide | 439.10 | 8.989 | B |
| 29 | 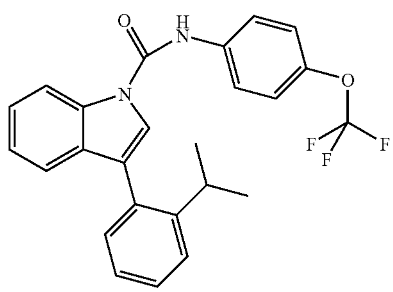 | 3-(2-isopropylphenyl)-N-(4-(trifluoromethoxy)phenyl)-1H-indole-1-carboxamide | 439.28 | 10.001 | B |
| 30 | 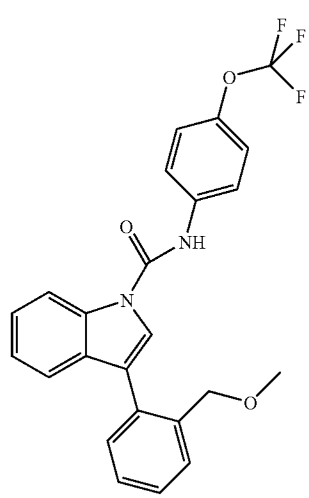 | 3-(2-(methoxymethyl)phenyl)-N-(4-(trifluoromethoxy)phenyl)-1H-indole-1-carboxamide | 439.10 | 9.376 | B |
| 31 | 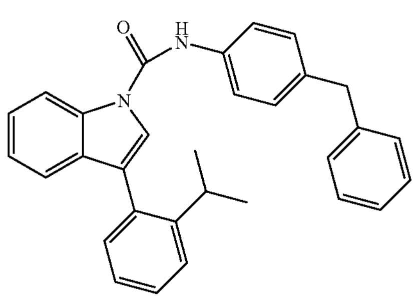 | N-(4-benzylphenyl)-3-(2-isopropylphenyl)-1H-indole-1-carboxamide | 445.26 | 4.37 | A |

TABLE 1-continued

| Example | Structure | Name | Observed MS ion | LC Retention Time (minutes) | LC Analysis Method |
|---|---|---|---|---|---|
| 32 | 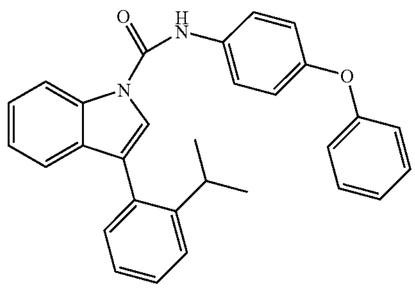 | 3-(2-isopropylphenyl)-N-(4-phenoxyphenyl)-1H-indole-1-carboxamide | 447.25 | 4.36 | A |
| 33 | 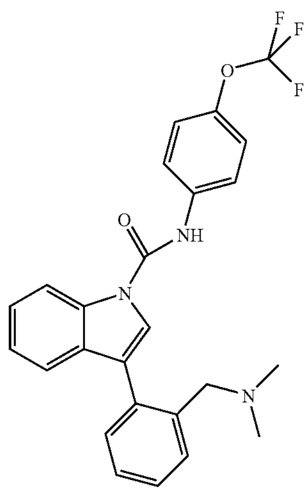 | 3-(2-((dimethylamino)methyl)phenyl)-N-(4-(trifluoromethoxy)phenyl)-1H-indole-1-carboxamide bis(2,2,2-trifluoroacetic acid) salt | 454.10 | 7.810 | B |
| 34 | 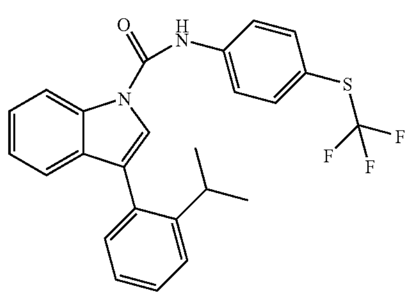 | 3-(2-isopropylphenyl)-N-(4-(trifluoromethylthio)phenyl)-1H-indole-1-carboxamide | 455.16 | 4.44 | A |
| 35 | 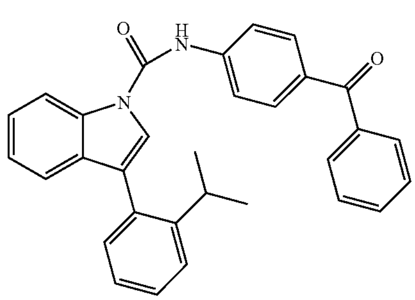 | N-(4-benzoylphenyl)-3-(2-isopropylphenyl)-1H-indole-1-carboxamide | 459.21 | 4.27 | A |

TABLE 1-continued

| Example | Structure | Name | Observed MS ion | LC Retention Time (minutes) | LC Analysis Method |
|---------|-----------|------|-----------------|------------------------------|---------------------|
| 36 | 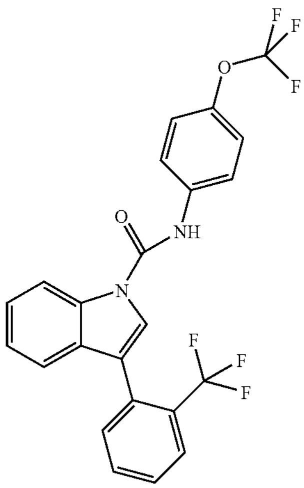 | N-(4-(trifluoromethoxy)phenyl)-3-(2-(trifluoromethyl)phenyl)-1H-indole-1-carboxamide | 465.00 | 9.268 | B |
| 37 | 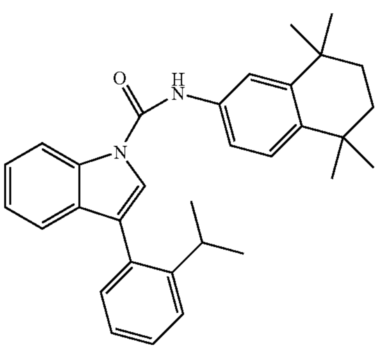 | 3-(2-isopropylphenyl)-N-(5,5,8,8-tetramethyl-5,6,7,8-tetrahydronaphthalen-2-yl)-1H-indole-1-carboxamide | 465.31 | 4.90 | A |
| 38 | 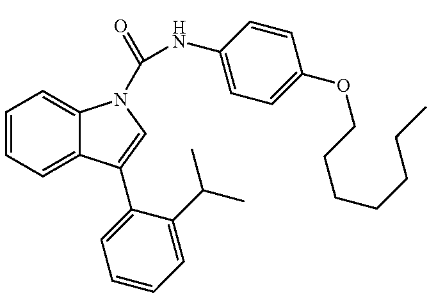 | N-(4-(heptyloxy)phenyl)-3-(2-isopropylphenyl)-1H-indole-1-carboxamide | 469.28 | 4.95 | A |

TABLE 1-continued

| Example | Structure | Name | Observed MS ion | LC Retention Time (minutes) | LC Analysis Method |
|---|---|---|---|---|---|
| 39 | 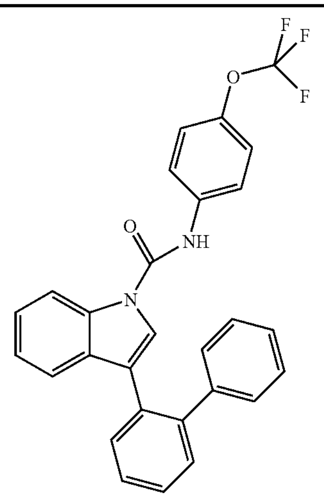 | 3-(biphenyl-2-yl)-N-(4-(trifluoromethoxy)phenyl)-1H-indole-1-carboxamide | 473.10 | 9.689 | B |
| 40 | 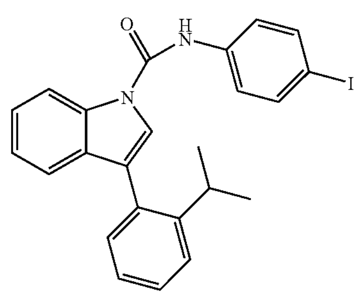 | N-(4-iodophenyl)-3-(2-isopropylphenyl)-1H-indole-1-carboxamide | 481.08 | 4.34 | A |
| 41 | 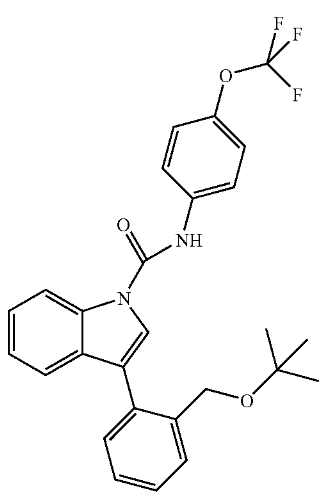 | 3-(2-(tert-butoxymethyl)phenyl)-N-(4-(trifluoromethoxy)phenyl)-1H-indole-1-carboxamide | 481.20 | 9.831 | B |
| 42 | 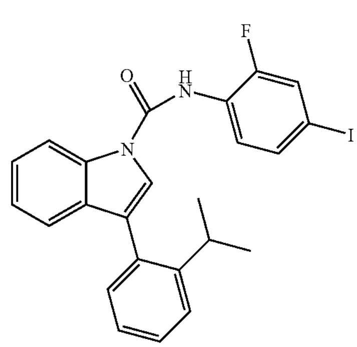 | N-(2-fluoro-4-iodophenyl)-3-(2-isopropylphenyl)-1H-indole-1-carboxamide | 499.05 | 4.28 | A |

TABLE 1-continued

| Example | Structure | Name | Observed MS ion | LC Retention Time (minutes) | LC Analysis Method |
|---|---|---|---|---|---|
| 43 | 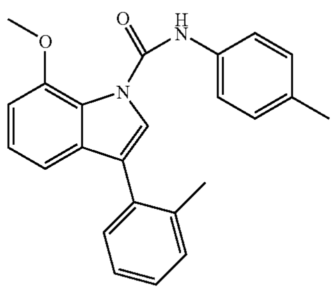 | 7-methoxy-3-o-tolyl-N-p-tolyl-1H-indole-1-carboxamide | 371.4 | 10.663 | C |
| 44 | 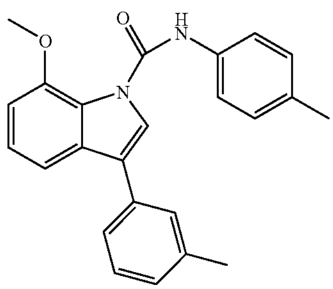 | 7-methoxy-3-m-tolyl-N-p-tolyl-1H-indole-1-carboxamide | 371.4 | 10.649 | C |
| 45 | 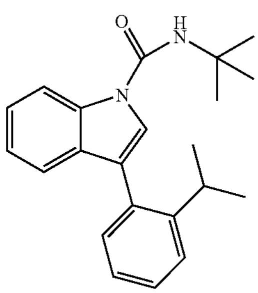 | N-tert-butyl-3-(2-isopropylphenyl)-1H-indole-1-carboxamide | 335.2 | 12.27 | C |
| 46 | 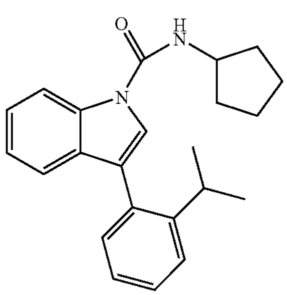 | N-cyclopentyl-3-(2-isopropylphenyl)-1H-indole-1-carboxamide | 347.2 | 12.27 | C |
| 47 | 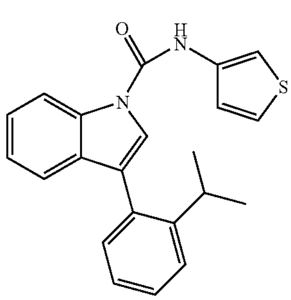 | 3-(2-isopropylphenyl)-N-(thiophen-3-yl)-1H-indole-1-carboxamide | 361.1 | 12.11 | C |

TABLE 1-continued

| Example | Structure | Name | Observed MS ion | LC Retention Time (minutes) | LC Analysis Method |
|---|---|---|---|---|---|
| 48 | 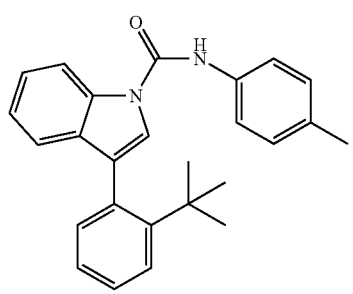 | 3-(2-isopropylphenyl)-N-m-tolyl-1H-indole-1-carboxamide | 369.1 | 12.52 | C |

Example 49

3-(2-tert-butylphenyl)-N-p-tolyl-1H-indole-1-carboxamide 1-(Phenylsulfonyl)-1H-indol-3-ylboronic acid (150.9 mg, 0.501 mmol), 2-tert-butylphenyl trifluoromethanesulfonate (255 mg, 0.902 mmol) and tetrakis(triphenylphosphine)palladium (0) (58 mg, 0.050 mmol) are combined in a septa capped microwave vial and placed under an argon atmosphere. Degassed solutions of 2 M sodium carbonate (0.75 mL, 1.50 mmol) and of dioxane (2.5 mL) were introduced and the vial heated to 150° C. for 15 minutes in a microwave reactor. The cooled reaction mixture was diluted with water and ethyl acetate, the phases separated and the aqueous extracted twice more with ethyl acetate. The combined extracts were washed with water, brine, dried over sodium sulfate, filtered and evaporated. The residue was purified by silica gel chromatography eluting with a gradient of ethyl acetate and hexanes to give 3-(2-tert-butylphenyl)-1-(phenylsulfonyl)-1H-indole (175.8 mg, 92%) as a colorless gummy solid.

3-(2-tert-Butylphenyl)-1-(phenylsulfonyl)-1H-indole (172.6 mg, 0.443 mmol) was combined with tetrahydrofuran (2.0 mL) and 1 M tetrabutylammonium fluoride solution (2.21 mL) and heated to 100° C. for 20 minutes. The cooled reaction is charged to a silica gel column and purified by eluting with a gradient of ethyl acetate and hexanes to give 3-(2-tert-butylphenyl)-1H-indole (26.8 mg, 26%) as a colorless solid.

3-(2-tert-Butylphenyl)-1H-indole (24.1 mg, 0.0967 mmol) in 0.5 mL anhydrous tetrahydrofuran was treated with 1M NaN(TMS)$_2$ in THF (0.2 mL) and stirred for 5 minutes at ambient temperature. 1-Isocyanato-4-methylbenzene (15 µL, 0.116 mmol) in 0.5 mL anhydrous tetrahydrofuran was added and stirred for 5 minutes at ambient temperature. 50 µL acetic acid and 200 µL methanol are added and the reaction mixture charged to a silica gel column and purified by eluting with a gradient of ethyl acetate and hexanes to give 3-(2-tert-butylphenyl)-N-p-tolyl-1H-indole-1-carboxamide which was further purified by reverse phase HPLC to give Example 49 (19.1 mg, 52%) as a colorless solid and 99.5% purity. LC/MS (ESI+) 383.4.

Example 50

1-(2-isopropylphenyl)-N-(4-(trifluoromethoxy)phenyl)-1H-indole-3-carboxamide

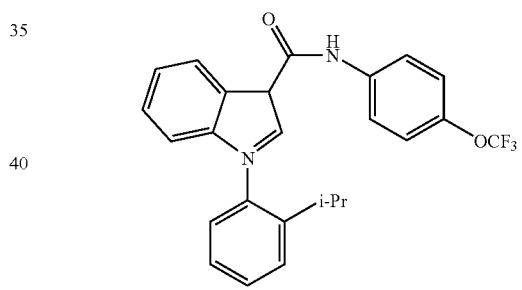

To a screw capped vial was added methyl 1H-indole-3-carboxylate (17 mg, 0.1 mmol), 2-isopropylbenzene boronic acid (33 mg, 0.20 mmol), and activated 3 Å molecular sieves (100 mg). Anhydrous dichloromethane (1.0 mL), anhydrous pyridine (16 µL, 0.2 mmol) and anhydrous triethylamine (28 µL, 0.2 mmol) were added, the vial capped and the reaction was stirred under air for 15 min. Anhydrous copper(II) acetate was added, the vial capped, and the reaction was stirred overnight under air at 45° C. The reaction was quenched with 20 drops of methanolic ammonium hydroxide (concentrated aqueous ammonia and methanol 1:1), filtered with the aid of additional dichloromethane in order to remove the molecular sieves and the solution applied to a silica gel column for chromatography. Elution with a gradient of ethyl acetate and hexanes furnished methyl 1-(2-isopropylphenyl)-1H-indole-3-carboxylate (10 mg, 35%) as a colorless solid. To methyl 1-(2-isopropylphenyl)-1H-indole-3-carboxylate (43 mg, 0.15 mmol) was added isopropanol (2 mL) and 1 N sodium hydroxide (1 mL) and heated to 50° C. for 2 days. The solvent was removed under reduced pressure and the residue was taken up in ethyl acetate and 1 N hydrochloric acid (1:1), the phases were separated and the aqueous was extracted twice more with ethyl acetate. The combined organics were dried over sodium sulfate, filtered, and evaporated to give 1-(2-isopropylphenyl)-1H-indole-3-carboxylic acid as a straw colored solid of sufficient purity for the next step (>95% LC purity). To 1-(2-isopropylphenyl)-1H-indole-3-carboxylic acid in anhydrous dimethylformamide (2.0 mL) was added anhydrous triethylamine (104 µL, 0.75 mmol), N,N-dimethylaminopyridine (9 mg, 0.075 mmol), 4-(trifluoromethoxy) aniline (32 mg, 0.18 mmol) and stirred for 5 min followed by the addition of PyBroP® (bromotris(pyrrolidino)phosphonium hexafluorophosphate) (105 mg, 0.225 mmol). The reaction was stirred for 14 h at 40° C. The reaction was quenched into water and ethyl acetate, the phases were separated and the aqueous phase was extracted twice more with ethyl acetate. The combined organics were washed successively five times with water, once with brine, dried over sodium sulfate and evaporated to yield a residue which was purified by silica gel column chromatography eluting with a gradient of ethyl acetate and hexanes to furnish Example 50 (14 mg, 20%) as a colorless solid. LC/MS (ESI+) 439.1 (M+H)+; (ESI−) 437.2 (M−H)−. 1H NMR (400 MHz, CD3OD) δ ppm 1.08 (d, J=7.03 Hz, 3H) 1.16 (d, J=6.59 Hz, 3H) 2.51-2.63 (m, 1H) 6.93-6.97 (m, 1H) 7.19-7.32 (m, 5H) 7.37-7.42 (m, 1H) 7.53-7.62 (m, 2H) 7.78-7.82 (m, 2H) 8.12 (s, 1H) 8.28-8.32 (m, 1H).

Example 51

N-(4-(1-(diethylamino)-2-methylpropan-2-yl)phenyl)-1-(2-isopropylphenyl)-1H-indole-3-carboxamide 2,2,2-trifluoroacetic acid salt

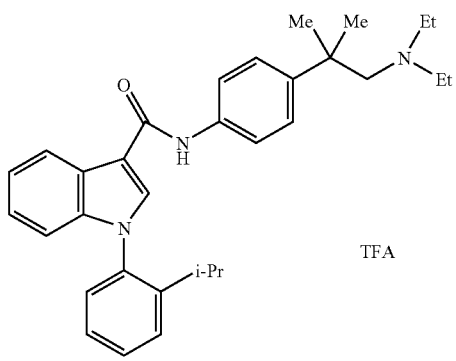

A 250 mL oven-dried flask capped with a rubber septum was evacuated and backfilled with argon. The flask was charged with NaH (7.26 g, 181 mmol, 60% dispersion in oil) anhydrous dimethylformamide (50 mL) and the flask was cooled to 0° C. Ethyl 2-chloropropionate (10.0 g, 73.2 mmol) and nitrobenzene (9.92 g, 80.5 mmol) were dissolved in anhydrous dimethylformamide (50 mL) and added dropwise to the sodium hydride slurry. The reaction was stirred for 30 min at 0° C., the cooling bath removed and the reaction was allowed to reach ambient temperature. After 1 h iodomethane (10.4 g, 73.2 mmol) was added and the mixture was stirred for an additional 30 min. The contents of the flask were poured into a mixture of ice and 1N HCl followed by three extractions with dichloromethane. The combined organic layers was washed five times with water, three times with saturated aqueous sodium bicarbonate solution, dried over sodium sulfate, filtered and concentrated in vacuo. Purification was performed by silica gel flash chromatography eluting with a gradient of hexanes and dichloromethane (30% hexanes in dichloromethane to 100% dichloromethane) to yield ethyl 2-methyl-2-(4-nitrophenyl)propanoate (7.32 g, 42.2%).

In a 250 mL oven-dried flask capped with a rubber septum and placed under a nitrogen atmosphere was charged ethyl 2-methyl-2-(4-nitrophenyl)propanoate (5.0 g, 21 mmol), anhydrous tetrahydrofuran (42 mL) and the flask was cooled to 0° C. To this was added via an addition funnel diisobutylaluminum hydride solution (63 mL, 1M in tetrahydrofuran) and the flask was allowed to warm to ambient temperature and stirred for 16 h. The reaction was quenched with Rochelle's salt, stirred for 30 min and filtered over Celite®. The solution was extracted three times with ethyl acetate and the combined organics were washed once each with Rochelle's salt, water, and brine. The organics were dried over sodium sulfate, filtered and concentrated in vacuo to give 2-methyl-2-(4-nitrophenyl)propan-1-ol (4.1 g, 99%).

In a 250 mL round bottom flask was charged 2-methyl-2-(4-nitrophenyl)propan-1-ol (3.86 g, 19.8 mmol), anhydrous dichloromethane (75 mL), 4-methylmorpholine N-oxide (3.47 g, 29.7 mmol), and 4 Å molecular sieves (9.8 g). TPAP (tetrapropylammonium perruthenate) (346 mg, 0.98 mmol) was added in one portion and the reaction was stirred at ambient temperature for 16 h. Upon completion of the reaction the material was filtered through a pad of silica and concentrated in vacuo. The material was purified by flash chromatography eluting with a gradient of 20% ethyl actetate/hexanes to 30% ethyl actetate/hexanes to give 2-methyl-2-(4-nitrophenyl)propanal (2.11 g, 55.1%).

In a 250 mL round bottom flask was charged 2-methyl-2-(4-nitrophenyl)propanal (2.00 g, 10.4 mmol), absolute ethanol (30 mL), ethyl amine solution (20.7 mL, 1M in THF). Titanium isopropoxide (6.2 mL, 20.7 mmol) was added and the mixture was stirred at ambient temperature for 1 h. Sodium borohydride (1.17 g, 31 mmol) was added and the reaction stirred for an additional 1 h. The reaction was quenched by pouring into 10% ammonium hydroxide solution (25 mL), ethyl acetate was added and the solids were removed by filtration, the pad was washed once with ethyl acetate and the solvent was concentrated in vacuo to give N-ethyl-2-methyl-2-(4-nitrophenyl)propan-1-amine (2.25 g, 98%). LC/MS (ESI+) 223 (M+H)+.

In a 100 mL round bottom flask was charged N-ethyl-2-methyl-2-(4-nitrophenyl)propan-1-amine (1.50 g, 6.75 mmol), anhydrous acetonitrile (22 mL), ethyl iodide (1.16 mL, 7.43 mmol), and potassium carbonate (1.87 g, 13.5 mmol). The reaction was brought to reflux for 4 h. The reaction mixture was filtered and concentrated in vacuo. The residue was diluted with water and ethyl acetate and layers were separated. The organic layer was washed with once each with water, and then with brine, dried over sodium sulfate, filtered and concentrated in vacuo to give N,N-diethyl-2-methyl-2-(4-nitrophenyl)propan-1-amine (1.45 g, 86.1%). LC/MS (ESI+) 251 (M+H)+.

In a 100 mL round bottomed flask was charged N,N-diethyl-2-methyl-2-(4-nitrophenyl)propan-1-amine (1.45 g, 5.79 mmol), ethyl acetate (29 mL) and a nitrogen atmosphere was introduced to the flask. 10% Palladium on activated carbon was carefully introduced and the flask contents were purged (evacuate—backfill) twice with nitrogen and lastly with hydrogen dispensed from a balloon. The reaction was stirred for 16 h under the hydrogen atmosphere. The hydrogen was removed and the solution was filtered over Celite®, rinsed with methanol and the filtrate was concentrated in vacuo to give 4-(1-(diethylamino)-2-methylpropan-2-yl) aniline (1.19 g, 93.5%) as a light yellow oil. LC/MS (ESI+) 221 (M+H)+.

To 1-(2-isopropylphenyl)-1H-indole-3-carboxylic acid (9 mg, 0.03 mmol) and N-ethyl-N-isopropylpropan-2-amine (14 μL, 0.08 mmol) in anhydrous dimethylformamide (0.5 mL) was added O-(7-Azabenzotriazol-1-yl)-N,N,N',N'-tetramethyluronium hexafluorophosphate (13 mg, 0.04 mmol and stirred for 5 min. 4-(1-(Diethylamino)-2-methylpropan-2-yl)aniline (11 mg, 0.05 mmol) was added and stirred overnight at ambient temperature. Water was added and the reaction was purified directly by preparative HPLC to give Example 51 (5 mg, 28%) as a white solid. LC/MS (ESI+) 482.4 (M+H)+.

Example 52

1-(2-isopropylphenyl)-N-p-tolyl-1H-indole-3-carboxamide

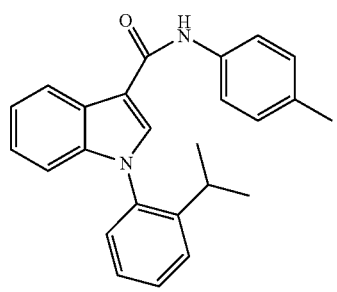

To an ice cooled solution of 1-(2-isopropylphenyl)-1H-indole (117 mg, 0.50 mmol) and pyridine (42.5 μL, 0.0524 mmol) in dichloromethane (anhydrous) (3.0 mL) under a nitrogen atmosphere is added triphosgene (146 mg, 0.50 mmol) and the reaction allowed to stir with warming to ambient temperature for overnight. An aliquot of the reaction solution (600 μL, 0.1 mmol) is removed and added to a solution of triethylamine (28 μL, 0.1 mmol), N,N-dimethylaminopyridine (2.4 mg, 0.2 mmol), and p-toluidine (12 mg, 0.11 mmol) in dichloromethane (anhydrous) (1.0 mL) and stirred at ambient temperature for 14 hours. The reaction mixture was concentrated and the residue purified by RP HPLC to give Example 51. LC/MS (ESI+) 369.5 (M+H)+.

Examples 53 and 54

The compounds for Examples 53 and 54 as described in the following Table 2 were prepared according to the procedure used for Example 52 substituting the appropriate amine to achieve the named compound.

TABLE 2

EXAMPLES 53 AND 54

| Example | Structure | Name | Observed MS ion | LC Retention Time (minutes) | LC Analysis Method |
|---|---|---|---|---|---|
| 53 | 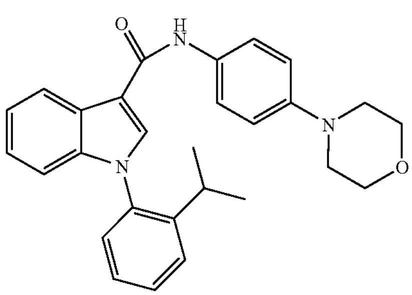 | 1-(2-isopropylphenyl)-N-(4-morpholinophenyl)-1H-indole-3-carboxamide 2,2,2-trifluoroacetic acid salt | 440.5 | 8.371 | B |
| 54 | 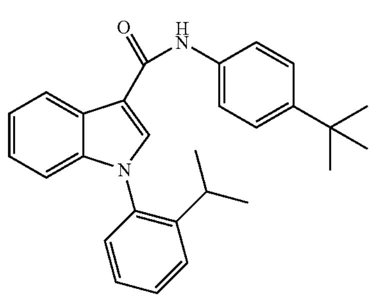 | N-(4-tert-butylphenyl)-1-(2-isopropylphenyl)-1H-indole-3-carboxamide | 411.5 | 9.578 | B |

Utility

The compounds of the present invention are anti-platelet agents and thus are useful to maintain the fluidity of blood. Additionally, compounds of the present invention are useful for the treatment or prophylaxis of platelet-associated disorders. As used herein, the term "platelet-associated disorder" refers to any disorder which may be prevented, partially alleviated, or cured by the administration of an anti-platelet agent.

The term anti-platelet agents (or platelet inhibitory agents), as used herein, denotes agents that inhibit platelet function, for example, by inhibiting the aggregation, adhesion or granule content secretion of platelets.

The term "thrombosis", as used herein, refers to formation or presence of a thrombus (pl. thrombi); clotting within a blood vessel which may cause ischemia or infarction of tissues supplied by the vessel. The term "embolism", as used herein, refers to sudden blocking of an artery by a clot or foreign material which has been brought to its site of lodgment by the blood current. The term "thromboembolism", as used herein, refers to obstruction of a blood vessel with thrombotic material carried by the blood stream from the site of origin to plug another vessel.

In general, a thromboembolic disorder is a circulatory disease caused by blood clots (i.e., diseases involving fibrin formation, platelet activation, and/or platelet aggregation). The term "thromboembolic disorders (or conditions)" as used herein also includes arterial or venous cardiovascular or cerebrovascular thromboembolic disorders, and thromboembolic disorders in the chambers of the heart or in the peripheral circulation.

Thus, the compounds of the present invention are useful in the treatment or prevention of various platelet associated disorders including: thrombotic or thromboembolic conditions; acute coronary syndromes (such as coronary artery disease, myocardial infarction (MI), unstable angina, and non-Q Wave MI); thromboembolic stroke (such as that resulting from atrial fibrillation or from ventricular mural thrombus (low ejection fraction)); venous thrombosis (including deep vein thrombosis); arterial thrombosis; cerebral thrombosis; pulmonary embolism; cerebral embolism; kidney embolisms; peripheral occlusive arterial disease (e.g., peripheral arterial disease, intermittent claudication, critical leg ischemia, prevention of amputation, prevention of cardiovascular morbidity such as MI, transient ischemic attack, stroke, or ischemic sudden death); thromboembolic consequences of surgery, interventional cardiology or immobility; thromboembolic consequences of medication (such as oral contraceptives, hormone replacement, and heparin); thrombotic consequences of atherosclerotic vascular disease and atherosclerotic plaque rupture leading to tissue ischemia; prevention of atherosclerotic plaque formation; transplant atherosclerosis; thromboembolic complications of pregnancy including fetal loss; thromboembolic consequences of thrombophilia (e.g., Factor V Leiden, and homocystinenimia); prothrombotic consequences and/or complications of cancer; coagulopathies (e.g., disseminated intravascular coagulation (DIC)); coagulation syndromes; vascular remodeling atherosclerosis, restenosis and systemic infection; prevention of metastasis and tumor implantation; diabetic complications including retinopathy, nephropathy and neuropathy; inflammation (e.g., thrombophlebitis); ischemia (such as that resulting from vascular occlusion, cerebral infarction, transient ischemic attack, stroke and related cerebral vascular diseases); Kasabach-Merritt syndrome; atrial fibrillation; ventricular enlargement (including dilated cardiac myopathy and heart failure); restenosis (e.g., following arterial injury-induced either endogenously or exogenously); thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, and vessel grafts. The procedures include, but are not limited to: cardiopulmonary bypass, percutaneous coronary intervention, and hemodialysis.

In addition to acting as anti-platelet agents, the compounds of the present invention may also find utility in a variety of other settings including as inhibitors of bone resorption such as encountered in various osteoporotic conditions, as inhibitors of insulin secretion in conditions of hyperinsulinemia, as vasoconstrictive agents such as those used in cases of septic or hypovolemic shock, as inhibitors of smooth muscle relaxation such for the treatment of incontinence or in other cases where inhibition of sympathetic nerve transmission would be of therapeutic benefit such as nociception or neuronal tissue regeneration. These and many other potential utilities for $P2Y_1$ antagonists have been recently reviewed (Burnstock, G. and Williams, M. *J. Pharm. Exp Ther.* 2000, 295, 862-9) and are suggested therein.

Compounds of the present invention may additionally be useful as diagnostic agents and adjuncts. For example, the present compounds may be useful in maintaining the reactivity of fractionated whole blood containing platelets such as required for analytical and biological testing or transfusions. In addition, the compounds of the present invention may be useful for maintaining blood vessel patency in conjunction with vascular surgery including bypass grafting, arterial reconstruction, atherectomy, vascular graft and stent patency, organ, tissue and cell implantation and transplantation. In addition, the compounds of the present invention may be useful for maintaining blood vessel patency in conjunction with interventional cardiology or vascular surgery including bypass grafting, arterial reconstruction, atherectomy, vascular graft and stent patency, organ, tissue and cell implantation and transplantation.

$P2Y_1$ Assays

A. Binding Assay—A

A membrane binding assay was used to identify inhibitors of $[^{33}P]$ 2MeS-ADP binding to cloned human $P2Y_1$ receptors. The cDNA clone for human $P2Y_1$ was obtained from Incyte Pharmaceuticals and its sequence confirmed by established techniques (for a compendium of techniques used see Ausubel, F. et al. *Current Protocols in Molecular Biology* 1995 John Wiley and Sons, NY, N.Y.). The essential coding sequences were subcloned into pcDNA 3.1 (Invitrogen) to produce a $P2Y_1$ expression construct. This construct was then transfected into the human embryonic kidney cell line HEK-293 and stable transfectants selected in Genetcin® (G418 sulfate; Life Technologies). Several lines were screened for binding activity and one (HEK293 #49) selected for further characterization. Membranes were prepared by growing HEK293 #49 in 150 mm dishes in DMEM/10% FBS in the presence of 1 mg/ml G418 until cells were 80-90% confluent. Plates were then washed with cold (4° C.) D-PBS twice and cells harvested by scraping into 10 mL D-PBS. Cells were pelleted by centrifugation (1,000 g, 10 min, 4° C.) and the resulting pellet resuspended in Lysis Buffer (10 mM Tris (7.4), 5 mM $MgCl_2$ containing Complete® protease inhibitor cocktail (Roche Cat #1873580) as recommended by the manufacturer). The suspension was then homogenized in a Dounce homogenizer (10-15 strokes; B pestle, on ice) and the homogenate spun at 1,000 g, 4° C., 5 min to pellet large debris. The supernatant was centrifuged at 150,000 g, 4° C., for 1 hour and the resulting membrane pellet resuspended in 0.5-1 mL of Buffer B (15 mM HEPES (7.4), 145 mM NaCl, 0.1 mM MgCl$_2$, 5 mM EDTA, 5 mM KCl) and stored at −70° C. until used.

Binding reactions were performed in WGA FlashPlates (PerkinElmer Life Sciences, Cat # SMP105A) in a volume of 200 μL containing ~45 fmol of P2Y$_1$ receptor (5 μg of total protein), 0.5 nM [$^{33}$P] 2MeS-ADP (PerkinElmer; 2,000 Ci/mmol), and various concentrations of the test compound (usually between 50 μM and 10 pM) in Buffer B containing 1% DMSO. Reactions were allowed to proceed to completion at room temperature for 1 hour and then the aqueous solution aspirated. Plates were sealed and the residual [$^{33}$P] bound to the plate determined by scintillation counting. Dose-response curves (IC$_{50}$) were fit by non-linear regression (XLFit, ID Business Solutions Ltd.) and binding constants (K$_i$) calculated using the Cheng-Prusoff relationship (K$_i$=IC$_{50}$/(1+L/K$_d$) in which a K$_d$ for 2MeS-ADP to the P2Y$_1$ receptor was determined to be 1.4 nM.

B. Binding Assay B—Scintillation Proximity Assay (SPA) for P2Y1 Binding:

A SPA membrane binding assay was used to identify inhibitors of [$^{33}$P] 2MeS-ADP binding to cloned human P2Y$_1$ receptors. (The P2Y1 receptor membranes were provided by Biology and the cloning of the receptor and P2Y1 receptor membrane preparation is same as described by Biology). Binding reactions were performed in 384-well Opti plates (PerkinElmer Life Sciences, Cat # 6007299) in a volume of 50 μL containing ~15 fmol of P2Y$_1$ receptor (1.7 μg of total protein), 0.3 nM [$^{33}$P] 2MeS-ADP (PerkinElmer; 2,000 Ci/mmol), various concentrations of the test compound (usually between 10 μM and 160 pM) in Buffer B containing 1% DMSO in assay buffer (15 mM, HEPES, 145 mM potassium chloride, 5 mM sodium Chloride, 5 mM EDTA, 0.1 mM MgCl$_2$, pH 7.4) and 100 μg of SPA bead (WGA polystyrene Image beads, #RPNQ 0260V, Amersham). Reactions were allowed to proceed to completion at room temperature for 1 hour followed by centrifugation of the plate for 5 min. About 40 μL of the aqueous solution was aspirated. Plates were sealed and the [$^{33}$P] 2MeS-ADP bound to the P2Y1 receptor membranes that were bound to the SPA bead were determined in a Gen 4 Leadseeker (Amersham) Image Reader. Dose-response curves (IC$_{50}$) were fit by non-linear regression (Toolset an in house data processing program) and binding constants (K$_i$) calculated using the Cheng-Prusoff relationship (K$_i$=IC$_{50}$/(1+L/K$_d$) in which a K$_d$ for 2MeS-ADP to the P2Y$_1$ receptor was determined to be 1.4 nM.

In general, preferred compounds of the present invention, such as the particular compounds disclosed in the above examples, have been identified to exhibit K$_i$'s of equal to or less than 10 μM in at least one of the P2Y$_1$ binding assays, thereby demonstrating these preferred compounds of the present invention as especially effective modulators of P2Y$_1$ activity. More preferred compounds have K$_i$'s of equal to or less than 5 μM, preferably equal to or less than 1 μM, more preferably equal to or less than 0.5 μM.

Data for some of the compounds obtained by Assay A is found in Table 3:

TABLE 3

| Example No. | P2Y1 KI nM |
|---|---|
| 1 | 75 |
| 12 | 117 |
| 27 | 144 |

TABLE 3-continued

| Example No. | P2Y1 KI nM |
|---|---|
| 33 | 1300 |
| 40 | 96 |
| 53 | 1208 |

The effectiveness of compounds of the present invention as antithrombotic agents can be determined using relevant in vivo thrombosis models, including In Vivo Electrically-induced Carotid Artery Thrombosis Models and In Vivo Rabbit Arterio-venous Shunt Thrombosis Models.

In Vivo Electrically-Induced Carotid Artery Thrombosis (ECAT) Model:

The rabbit ECAT model, described by Wong et al. (*J Pharmacol Exp Ther* 2000, 295, 212-218), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to the initiation of thrombosis. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by trapezoidal rule. Average carotid flow over 90 min is then determined by converting total carotid blood flow over 90 min to percent of total control carotid blood flow, which would result if control blood flow had been maintained continuously for 90 min. The ED$_{50}$ (dose that increased average carotid blood flow over 90 min to 50% of the control) of compounds are estimated by a nonlinear least square regression program using the Hill sigmoid E$_{max}$ equation (DeltaGraph; SPSS Inc., Chicago, Ill.).

In Vivo Rabbit Arterio-Venous (AV) Shunt Thrombosis Model:

The rabbit AV shunt model, described by Wong et al. (Wong, P. C. et al. *J Pharmacol Exp Ther* 2000, 292, 351-357), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm). The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The ID$_{50}$ values (dose which produces 50% inhibition of thrombus formation) are estimated by a nonlinear least square regression program using the Hill sigmoid E$_{max}$ equation (DeltaGraph; SPSS Inc., Chicago, Ill.).

The compounds of the present invention can be administered alone or in combination with one or more additional therapeutic agents. These other agents include, but are not limited to, anticoagulant or coagulation inhibitory agents, other antiplatelet or platelet inhibitory agents, or thrombolytic or fibrinolytic agents.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Examples of suitable anti-arrhythmic agents for use in combination with the present compounds include: Class I agents (such as propafenone); Class II agents (such as carvadiol and propranolol); Class III agents (such as sotalol, dofetilide, amiodarone, azimilide, and ibutilide); Class IV agents (such as ditiazem and verapamil); K$^+$ channel openers such as $I_{Ach}$ inhibitors, and $I_{Kur}$ inhibitors (e.g., compounds such as those disclosed in WO01/40231).

Examples of suitable antihypertensive agents for use in combination with the compounds of the present invention include: alpha adrenergic blockers; beta adrenergic blockers; calcium channel blockers (e.g. diltiazem, verapamil, nifedipine, amlodipine, and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; angiotensin-converting enzyme (ACE) inhibitors (e.g., captopril, zofenopril, fosinopril, enalapril, ceranopril, cilazopril, delapril, pentopril, quinapril, ramipril, lisinopril); angiotensin AT-1 receptor antagonists (e.g., losartan, irbesartan, valsartan); ET-A receptor antagonists (e.g., sitaxsentan, atrsentan, and compounds disclosed in U.S. Pat. Nos. 5,612,359 and 6,043,265); Dual ET-A/AT-1 antagonist (e.g., compounds disclosed in WO 00/01389); neutral endopeptidase (NEP) inhibitors; vasopepsidase inhibitors (dual NEP-ACE inhibitors) (e.g., omapatrilat, gemopatrilat, and nitrates); and β-blockers (e.g., propanolol, nadolo, or carvedilol).

Examples of other suitable anti-platelet agents for use in combination with the compounds of the present invention, include, but are not limited to, the various known non-steroidal anti-inflammatory drugs (NSAIDS) such as acetaminophen, aspirin, codeine, diclofenac, droxicam, fentaynl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDS, aspirin (acetylsalicyclic acid or ASA) and piroxicam are preferred. Other suitable platelet inhibitory agents include glycoprotein IIb/IIIa blockers (e.g., abciximab, eptifibatide, tirofiban, integrelin), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), protease-activated receptor 1 (PAR-1) antagonists (e.g., SCH-530348, SCH-203099, SCH-529153, and SCH-205831), and pharmaceutically acceptable salts or prodrugs thereof.

Other examples of suitable anti-platelet agents for use in combination with the compounds of the present invention, with or without aspirin, include: ADP (adenosine diphosphate) receptor antagonists including P2Y$_{12}$ antagonists and other P2Y$_1$ antagonists. Preferred P2Y$_{12}$ receptor antagonists, but are not limited to, clopidogrel, ticlopidine, prasugrel, and AZD-6140, including pharmaceutically acceptable salts or prodrugs thereof. Ticlopidine and clopidogrel are also preferred compounds since they are known to be more gentle than aspirin on the gastrointestinal tract in use. Clopidogrel is an even more preferred agent.

Examples of suitable anticoagulants for use in combination with the compounds of the present invention include warfarin and heparin (either unfractionated heparin such as enoxaparin and dalteparin or any commercially available low molecular weight heparin, for example LOVENOX™), synthetic pentasaccharide, direct acting thrombin inhibitors including hirudin and argatroban, factor VIIa inhibitors, factor IXa inhibitors, factor Xa inhibitors (e.g., Arixtra™, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, thrombin inhibitors, inhibitors of factors IXa, Xa, and XIa, PAI-1 inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable calcium channel blockers (L-type or T-type) for use in combination with the compounds of the present invention include diltiazem, verapamil, nifedipine, amlodipine and mybefradil.

Examples of suitable cardiac glycosides for use in combination with the compounds of the present invention include digitalis and ouabain.

Examples of suitable diruetics for use in combination with the compounds of the present invention include: chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone.

Examples of suitable mineralocorticoid receptor antagonists for use in combination with the compounds of the present invention include sprionolactone and eplirinone.

Examples of suitable cholesterol/lipid lowering agents and lipid profile therapies for use in combination with the compounds of the present invention include: HMG-CoA reductase inhibitors (e.g., pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; nicotonic acid; fenofibric acid derivatives (e.g., gemfibrozil, clofibrat, fenofibrate and benzafibrate); probucol; choesterol absorption inhibitors; and cholesterol ester transfer protein inhibitors (e.g., CP-529414).

Examples of suitable anti-diabetic agents for use in combination with the compounds of the present invention include: biguanides (e.g. metformin); glucosidase inhibitors (e.g. acarbose); insulins (including insulin secretagogues or insulin sensitizers); meglitinides (e.g. repaglinide); sulfonylureas (e.g., glimepiride, glyburide and glipizide); biguanide/glyburide combinations (e.g., glucovance), thiozolidinediones (e.g. troglitazone, rosiglitazone, and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DPP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protein tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-obesity agents for use in combination with the compounds of the present invention include orlistat, aP2 inhibitors (such as those disclosed in WO00/59506), and cannabinoid receptor CB1 antagonists (e.g., rimonabant, AVE-1625, SR-147778, and CP-945598).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each. A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of platelet ADP receptor. Such compounds may be provided in a commercial kit, for example, for use in pharmaceutical research involving platelet ADP receptor. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving platelet ADP receptor. For example, the presence of $P2Y_1$ in an unknown sample could be determined by addition of the relevant radiolabled compound to the sample and measuring the extend of binding to the $P2Y_1$ receptor.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 0.1 to 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to 100 milligrams of the compound of the present invention and about 0.1 to 7.5 milligrams of the second anticoagulant, per kilogram of patient body weight. For a tablet dosage form, the compounds of this invention generally may be present in an amount of about 5 to 100 milligrams per dosage unit, and the second anti-coagulant in an amount of about 1 to 50 milligrams per dosage unit.

Where the compounds of the present invention are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of antiplatelet agents, per kilogram of patient body weight.

Where the compounds of the present invention are administered in combination with thrombolytic agent, typically a daily dosage may be about 0.1 to 1 milligrams of the compound of the present invention, per kilogram of patient body weight and, in the case of the thrombolytic agents, the usual dosage of the thrombolytic agent when administered alone may be reduced by about 50-80% when administered with a compound of the present invention.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

What is claimed is:

1. A compound of Formula (IIb):

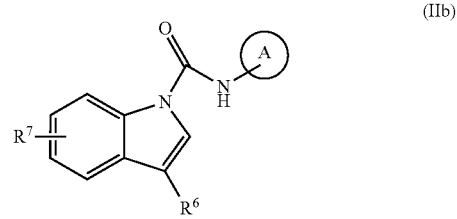

or pharmaceutically acceptable salts thereof, wherein:

A is selected from the group consisting of phenyl, 2-F-phenyl, 4-F-phenyl, 4-l-phenyl, 4-methyl-phenyl, 4-ethyl-phenyl, 4-isopropylphenyl, 4-n-butylphenyl, 4-sec-butylphenyl, 4-tert-butylphenyl, 4-$CF_3$-phenyl, 4-methoxyphenyl, 4-ethoxy-phenyl, 4-n-butoxyphenyl, 4-n-heptoxyphenyl, 4-methylthiophenyl, 4-acetylphenyl, 4-difluoromethoxy-phenyl, 4-trifluoromethoxy-phenyl, 4-trifluoromethylthio-phenyl, 4-$NMe_2$-phenyl, 4-$NO_2$-phenyl, 4-cyanomethylphenyl, 2-methylcarbonyl-phenyl, 4-$CO_2$Et-phenyl, 4-(1-(diethylamino)-2-methylpropan-2-yl)-phenyl, 2,4-difluorophenyl, 2,5-difluorophenyl, 4-Cl-2-F-phenyl, 4-l-2-F-phenyl, biphenyl-4-yl, 4-benzylphenyl, 4-phenoxyphenyl, 4-phenylcarbonylphenyl, and

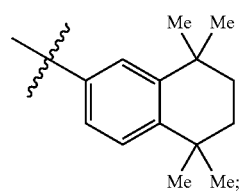

$R^6$ is selected from the group consisting of phenyl, 2-ethyl-phenyl, 2-isopropylphenyl, 2-vinyl-phenyl, 2-trifluoromethyl-phenyl, 2-(methoxymethyl)-phenyl, 2-(t-butoxymethyl)-phenyl, 2-formyl-phenyl, 2-acetylphenyl, 4-$NMe_2$-phenyl, and biphenyl-2-yl; and $R^7$ is H;

provided that:

when A is phenyl, then $R^6$ is other than phenyl.

2. A compound selected from the group consisting of:
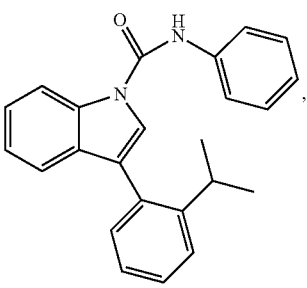,
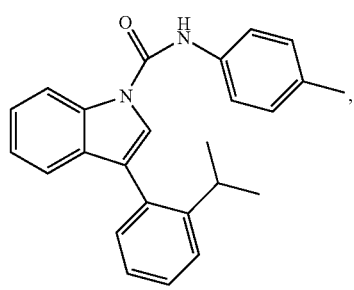,
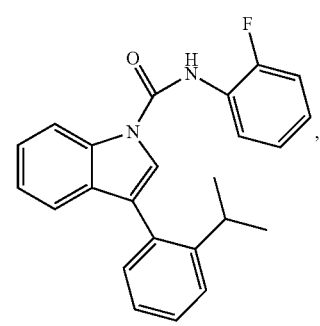,
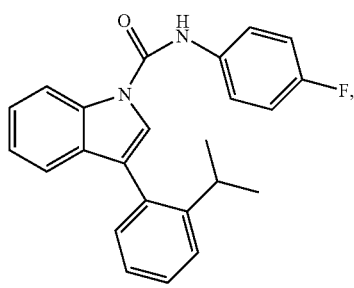,
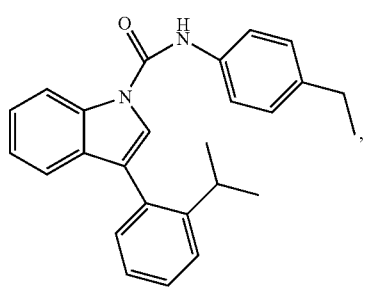,
-continued
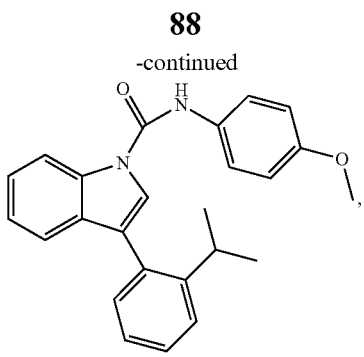,
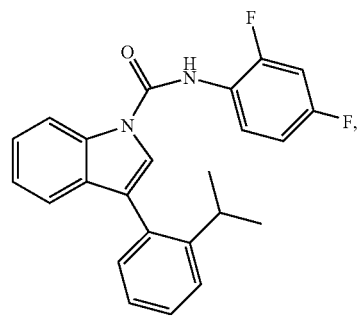,
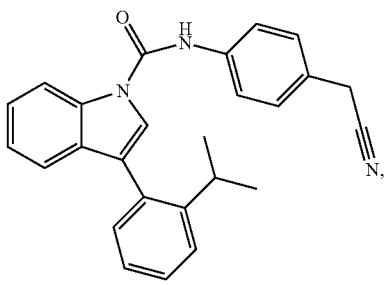,
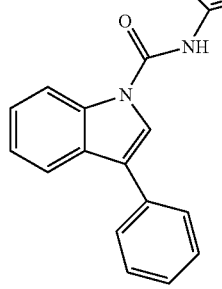,
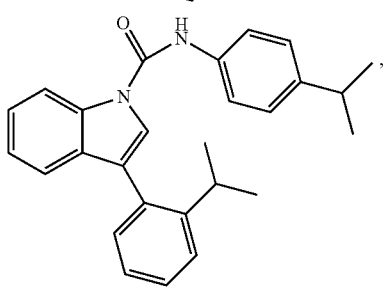,

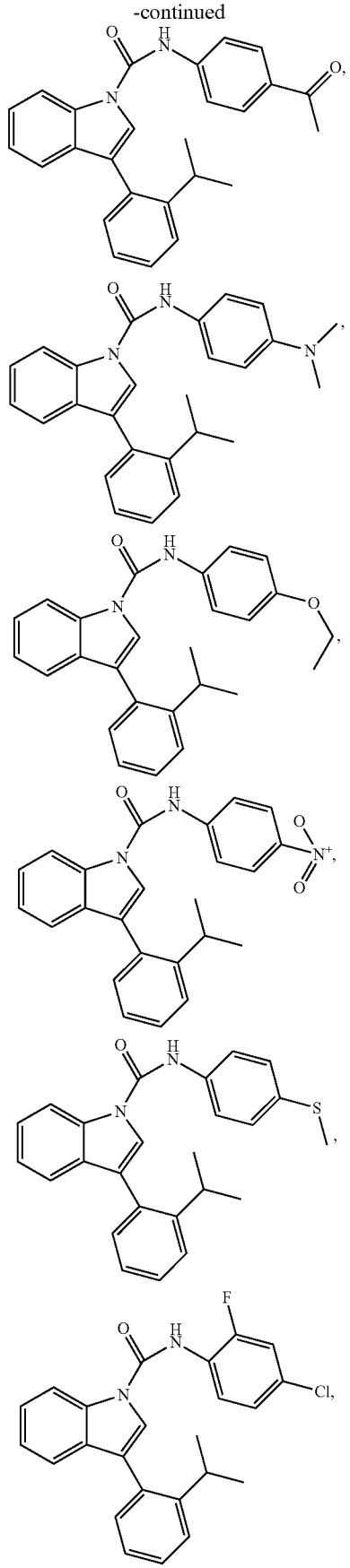
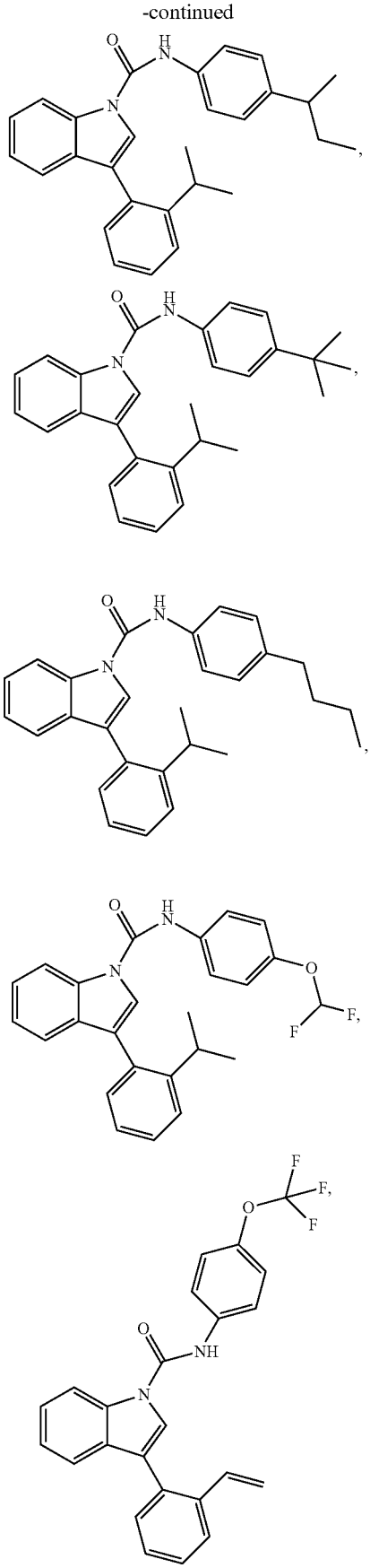

91
-continued
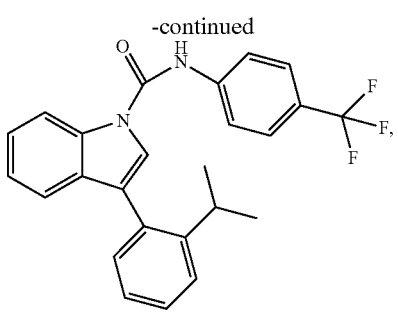
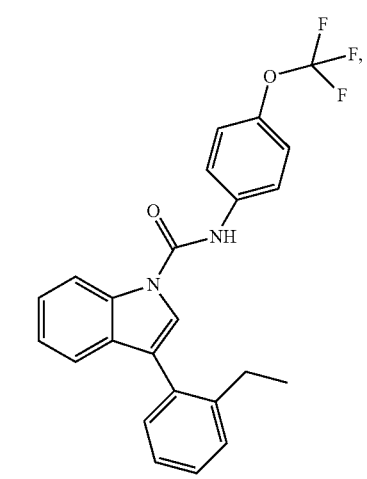
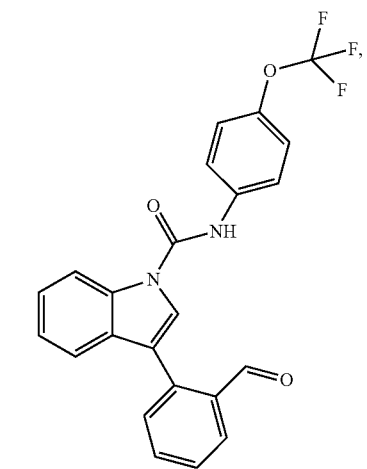
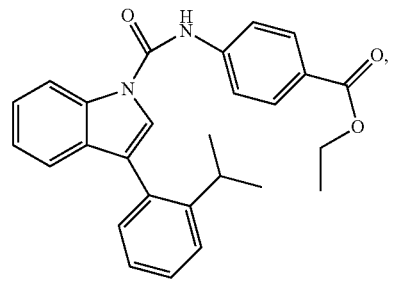
92
-continued
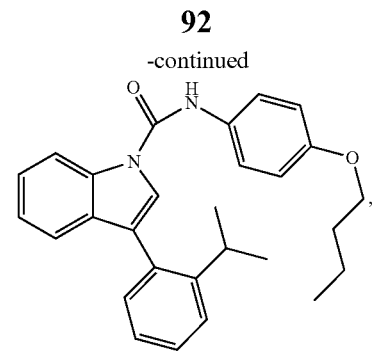
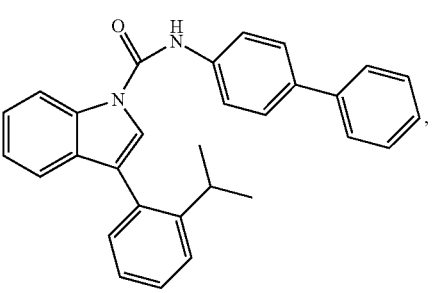
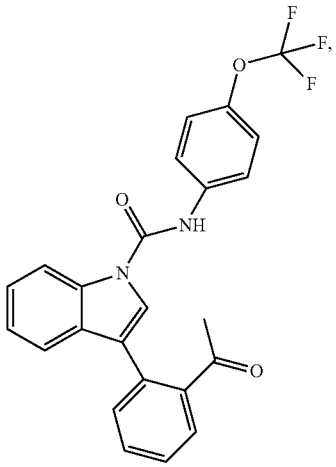
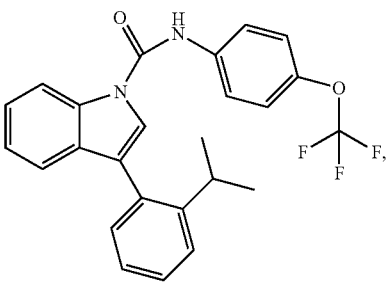

93
-continued
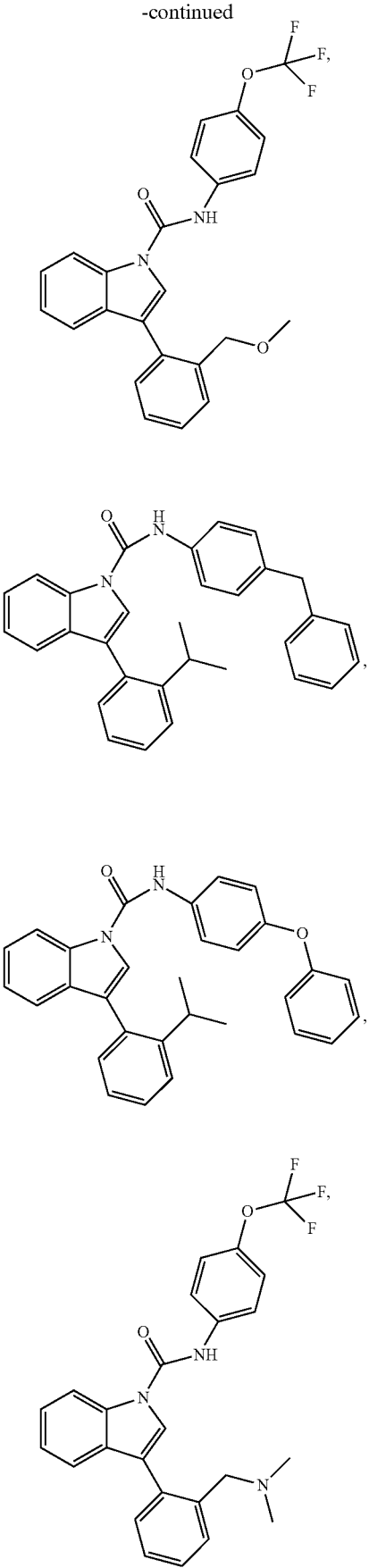
94
-continued
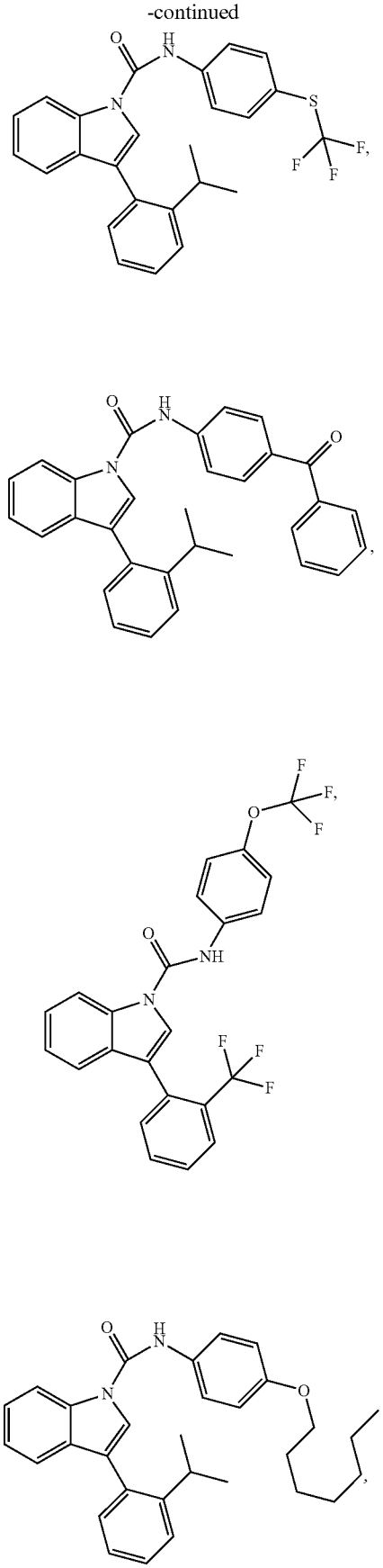

-continued
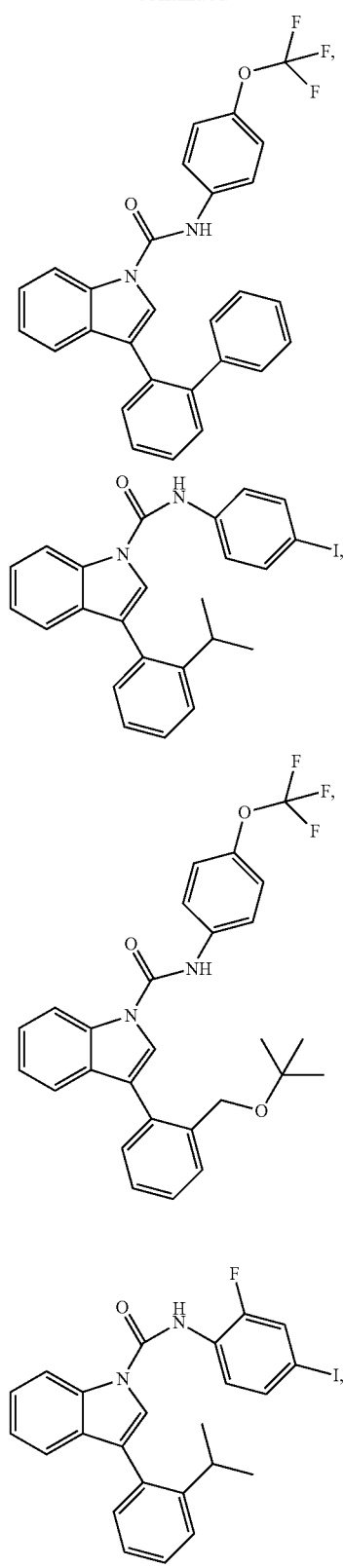
-continued
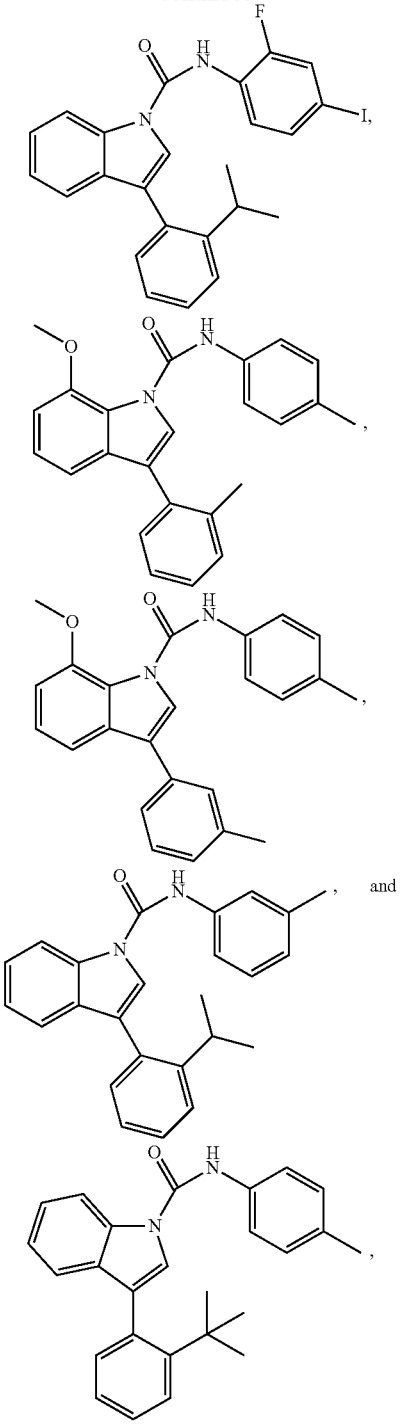
or pharmaceutically acceptable salts thereof.
3. A pharmaceutical composition, comprising: a pharmaceutically acceptable carrier and a compound of claim 1.
4. A pharmaceutical composition, comprising: a pharmaceutically acceptable carrier and a compound of claim 2.
* * * * *

UNITED STATES PATENT AND TRADEMARK OFFICE
CERTIFICATE OF CORRECTION

PATENT NO. : 7,960,569 B2
APPLICATION NO. : 11/872816
DATED : June 14, 2011
INVENTOR(S) : Patrick Y. S. Lam and Charles G. Clark Page 1 of 2

It is certified that error appears in the above-identified patent and that said Letters Patent is hereby corrected as shown below:

Column 94
Line 53 above " 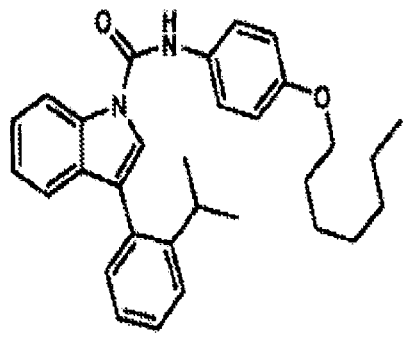 , "

insert -- 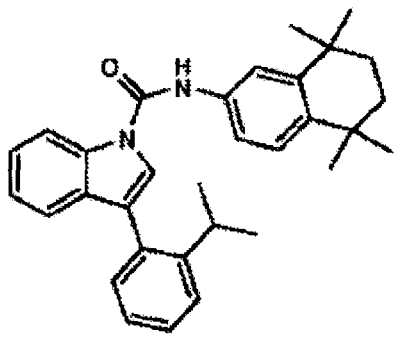 , --

Signed and Sealed this
Twenty-second Day of November, 2011

David J. Kappos
Director of the United States Patent and Trademark Office

CERTIFICATE OF CORRECTION (continued)
U.S. Pat. No. 7,960,569 B2

Column 96
Line 1-13

In Claim 2, above " 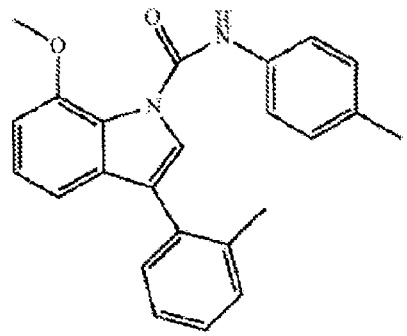 "

delete " 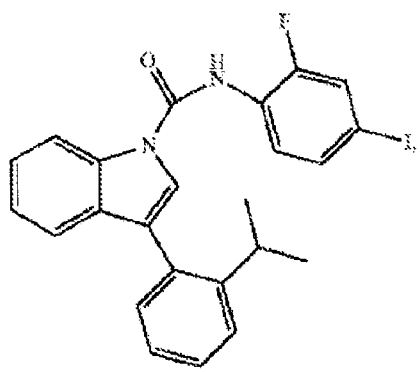 "